US009675751B2

(12) United States Patent
Hwang et al.

(10) Patent No.: US 9,675,751 B2
(45) Date of Patent: Jun. 13, 2017

(54) INFUSION RESERVOIR WITH PUSH-ON CONNECTOR FEATURES AND/OR ATTACHMENTS THEREFOR

(75) Inventors: Charles Hwang, Wellesley, MA (US); Gary Searle, Norfolk, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 997 days.

(21) Appl. No.: 13/190,400

(22) Filed: Jul. 25, 2011

(65) Prior Publication Data
US 2012/0029431 A1 Feb. 2, 2012

Related U.S. Application Data

(60) Provisional application No. 61/369,706, filed on Jul. 31, 2010.

(51) Int. Cl.
| A61M 1/00 | (2006.01) |
| A61M 5/142 | (2006.01) |
| A61M 5/38 | (2006.01) |
| A61M 5/145 | (2006.01) |
| A61M 39/10 | (2006.01) |

(52) U.S. Cl.
CPC ........ A61M 5/14248 (2013.01); A61M 5/385 (2013.01); *A61M 2005/14573* (2013.01); *A61M 2039/1027* (2013.01); *Y10T 29/49826* (2015.01)

(58) Field of Classification Search
CPC ...... A61M 2005/2492; A61M 5/14248; A61M 1/0072; A61M 5/385; A61M 2039/1027; A61M 2005/14573
USPC ................................................ 604/151–155
See application file for complete search history.

(56) References Cited

U.S. PATENT DOCUMENTS

| 2,468,849 A | 5/1949 | Trainor |
| 3,128,009 A | 4/1964 | Norton |
| 4,372,584 A | 2/1983 | Miller |

(Continued)

FOREIGN PATENT DOCUMENTS

| JP | 2005-527335 A | 9/2005 |
| JP | 2009-233388 A | 10/2009 |

OTHER PUBLICATIONS

Wigner et al., "Use of Expanded PTFE Membranes in Medical Filtration", Medical Design Technology, Sep. 2009, pp. 1-5.

*Primary Examiner* — Edelmira Bosques
(74) *Attorney, Agent, or Firm* — Dickinson Wright PLLC

(57) ABSTRACT

A reservoir and straight-line, push-on connector assembly is provided for connecting the reservoir and one of a standard Luer line set and a custom Luer line set to any number of infusion pump configurations using a simple straight-line, push-on motion, wherein the push-on connector assembly is provided and configured to secure the line set and reservoir with the infusion pump. One simple straight-line, push-on motion, preferably performed by gripping an expander sleeve, places and secures the reservoir (i.e., locates the reservoir on the x, y, and z axes) in the pump reservoir cavity, and one simple straight-line, pull-off motion releases and removes the reservoir from the pump reservoir cavity. Rotational orientation is not required for connection, pump engagement, or pump function, and any pulling of the tube set will not release the reservoir as the expansion sleeve through which the tube set is routed is not moved from the securing position by tension on the tube set or Luer fitting.

31 Claims, 48 Drawing Sheets

(56) References Cited

U.S. PATENT DOCUMENTS

| | | | |
|---|---|---|---|
| 4,813,937 | A | 3/1989 | Vaillancourt |
| D303,013 | S | 8/1989 | Konopka |
| 5,002,537 | A | 3/1991 | Hoffman et al. |
| 5,334,179 | A | 8/1994 | Poli et al. |
| 5,334,188 | A | 8/1994 | Inoue et al. |
| 5,514,090 | A | 5/1996 | Kriesel et al. |
| 5,545,152 | A | 8/1996 | Funderburk et al. |
| 5,618,268 | A | 4/1997 | Raines et al. |
| D380,262 | S | 6/1997 | Van Funderburk et al. |
| 5,947,935 | A | 9/1999 | Rhinehart et al. |
| 6,106,498 | A | 8/2000 | Friedli et al. |
| 6,248,093 | B1 | 6/2001 | Moberg |
| 6,260,890 | B1 | 7/2001 | Mason |
| 6,368,307 | B1 | 4/2002 | Ziemba et al. |
| 6,423,053 | B1 | 7/2002 | Lee |
| D461,241 | S | 8/2002 | Moberg et al. |
| D461,891 | S | 8/2002 | Moberg |
| 6,485,483 | B1 | 11/2002 | Fujii |
| 6,585,695 | B1 | 7/2003 | Adair et al. |
| 6,595,979 | B1 | 7/2003 | Epstein et al. |
| 6,652,489 | B2 * | 11/2003 | Trocki et al. ............... 604/154 |
| 6,689,086 | B1 | 2/2004 | Nita et al. |
| 6,800,071 | B1 | 10/2004 | McConnell et al. |
| 6,817,990 | B2 | 11/2004 | Yap et al. |
| 6,854,620 | B2 | 2/2005 | Ramey |
| 7,063,684 | B2 | 6/2006 | Moberg |
| 7,137,654 | B2 | 11/2006 | Segal et al. |
| 7,306,578 | B2 | 12/2007 | Gray et al. |
| 7,628,772 | B2 | 12/2009 | McConnell et al. |
| 7,628,782 | B2 | 12/2009 | Adair et al. |
| 7,658,734 | B2 | 2/2010 | Adair et al. |
| 7,981,105 | B2 | 7/2011 | Adair et al. |
| 2002/0173748 | A1 | 11/2002 | McConnell et al. |
| 2003/0130618 | A1 * | 7/2003 | Gray ............... A61M 5/1456 604/93.01 |
| 2003/0161744 | A1 | 8/2003 | Vilks et al. |
| 2003/0163090 | A1 | 8/2003 | Blomquist et al. |
| 2003/0199847 | A1 | 10/2003 | Akerlund et al. |
| 2004/0003493 | A1 | 1/2004 | Adair et al. |
| 2004/0092873 | A1 | 5/2004 | Moberg |
| 2004/0133166 | A1 * | 7/2004 | Moberg ............... A61M 5/1456 604/151 |
| 2004/0243065 | A1 | 12/2004 | McConnell et al. |
| 2005/0240154 | A1 | 10/2005 | Mogensen et al. |
| 2005/0277882 | A1 | 12/2005 | Kriesel |
| 2006/0100581 | A1 | 5/2006 | Mogensen |
| 2007/0078393 | A1 | 4/2007 | Lynch et al. |
| 2007/0167912 | A1 | 7/2007 | Causey et al. |
| 2008/0045929 | A1 | 2/2008 | Birnbach |
| 2008/0097309 | A1 * | 4/2008 | Enegren et al. ............... 604/111 |
| 2008/0200900 | A1 | 8/2008 | Aeschlimann et al. |
| 2008/0262425 | A1 | 10/2008 | Mogensen |
| 2009/0076453 | A1 | 3/2009 | Mejlhede et al. |
| 2009/0099523 | A1 | 4/2009 | Grant et al. |
| 2009/0137979 | A1 | 5/2009 | Adair et al. |
| 2009/0177159 | A1 | 7/2009 | Knopper et al. |
| 2009/0299288 | A1 | 12/2009 | Sie et al. |
| 2010/0049135 | A1 | 2/2010 | Adair et al. |
| 2010/0049144 | A1 | 2/2010 | McConnell et al. |
| 2010/0082010 | A1 | 4/2010 | Adair et al. |
| 2010/0125247 | A1 | 5/2010 | Adair et al. |
| 2010/0168670 | A1 | 7/2010 | Srisathapat et al. |
| 2011/0060312 | A1 | 3/2011 | Scheurer |
| 2011/0160667 | A1 | 6/2011 | Bazargan et al. |
| 2011/0190704 | A1 | 8/2011 | Lynch et al. |

\* cited by examiner

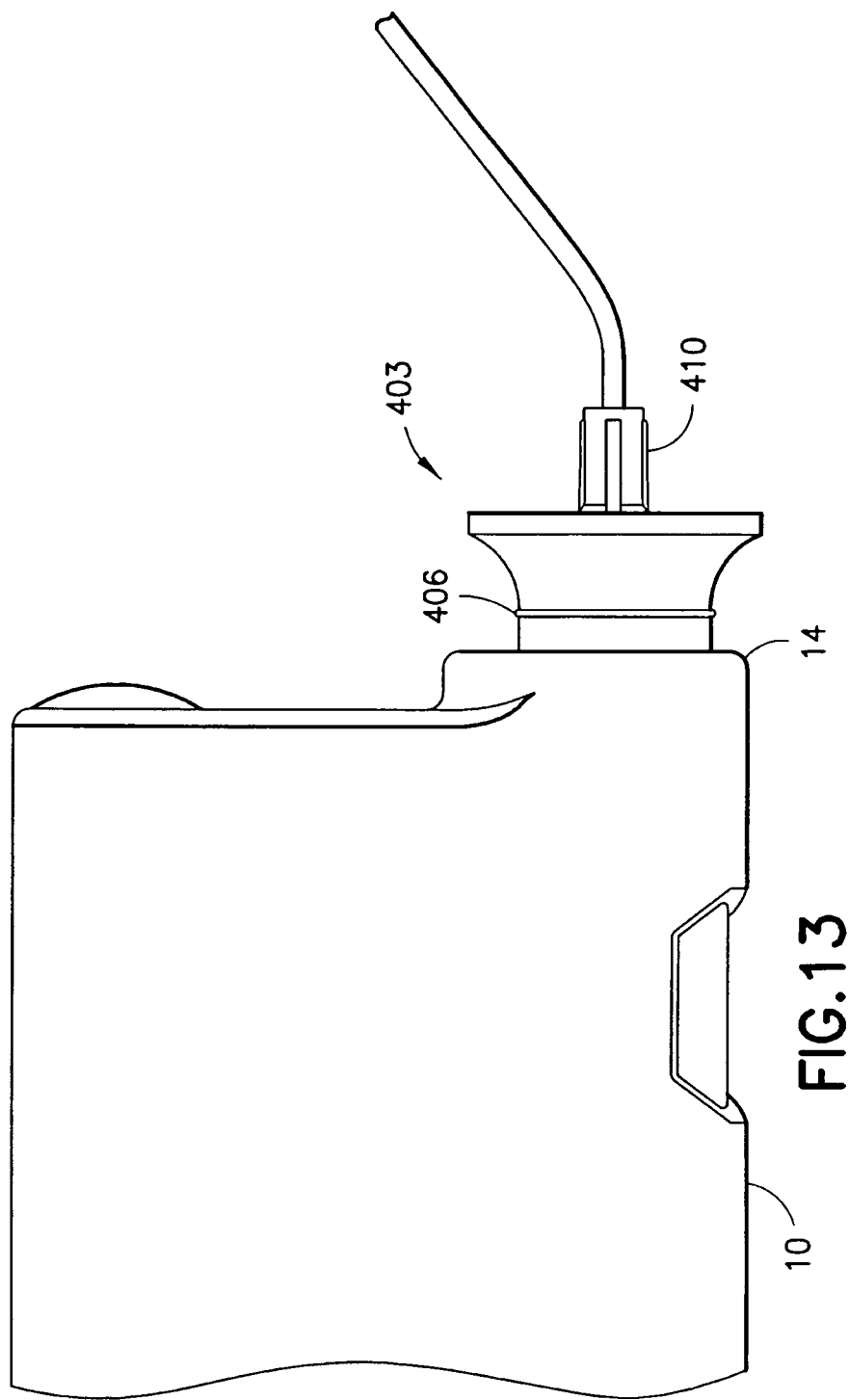

INFUSION RESERVOIR WITH PUSH-ON CONNECTOR FEATURES AND/OR ATTACHMENTS THEREFOR

CROSS-REFERENCE TO RELATED APPLICATIONS

This application claims the benefit under 35 U.S.C. §119 (e) of a U.S. provisional patent application of Charles Hwang et al. entitled "Infusion Reservoir With Push-On Connector Features and/or Attachments Therefor", Ser. No. 61/369,706, filed on Jul. 31, 2010, the entire content of said application being incorporated herein by reference.

FIELD OF THE INVENTION

The present invention relates generally to components and elements of infusion systems, including a push-on connector and reservoir assembly for connecting the reservoir and line set to any number of infusion pump configurations using a simple straight-line push-on motion.

BACKGROUND OF THE INVENTION

A large number of people, including those suffering from conditions such as diabetes use some form of infusion therapy, such as daily insulin infusions to maintain close control of their glucose levels. There are currently two principle modes of daily treatment for insulin infusion therapy. The first mode, referred to as Multiple Daily Injections or MDIs, includes syringes and insulin pens. These devices are simple to use and are relatively low in cost, but they require a needle stick at each injection, typically three to four times per day. The second mode includes infusion pump therapy, which entails the purchase of an insulin pump that lasts for about four years. The initial cost of the pump can be significant, but from a user perspective, the overwhelming majority of patients who have used pumps prefer to remain with pumps for the rest of their lives. This is because infusion pumps, although more complex than syringes and pens, offer the advantages of continuous infusion of insulin, precision dosing and programmable delivery schedules. This results in closer blood glucose control and an improved feeling of wellness.

However, patients may encounter situations wherein different configurations of infusion pumps, reservoirs and line sets are required for one or more reasons, and such patients may become concerned that the different configurations could adversely affect dosing and programmable delivery schedules. Plus, many current systems and methods require user actions or motions not fully compatible with each user's abilities.

For example, a first conventional system and method requires two separate engagement/disengagement operations for connecting the reservoir and line set to the infusion pump. For engagement, the user first slides or pushes a reservoir into the pump reservoir cavity, then turns a separate threaded sleeve with sufficient torque to thread and tighten the sleeve into position. For disengagement, the user first unscrews the separate threaded sleeve, and then pulls the reservoir from the pump reservoir cavity. The human factors are not intuitive with this second operation, and there is a tendency to unscrew the line connection from the reservoir. Applying a counter clockwise turning motion to the only grip point, i.e. the Luer connector, will unscrew the Luer, allowing insulin to leak onto the top surface of the reservoir and create an opportunity for the leaked insulin to migrate into the pump reservoir cavity as the reservoir is pulled from the cavity. Also, at least one or more sealing O-rings are typically provided in such devices, and the compression forces required by such O-rings can be substantial. Still further, once released in a manner described above, there are few grip points from which to pull the released reservoir from the pump reservoir cavity.

Another failure that could occur in such a system and method is the separation of the line from the Luer connector, again resulting in insulin leakage from the line. Also, in many such systems and methods, there is no audible feedback when the separate threaded sleeve has been torqued to the proper degree, nor is there any visible indication that the separate threaded sleeve has disengaged, i.e. unscrewed to some degree, during use.

In such a system and method, the user motions necessary to place the reservoir into the pump reservoir cavity and complete the engagement of the line set connection are excessive and not intuitive, and the separate threaded sleeve is akin to a wear component requiring periodic replacement. However, the user may not always know when the sleeve requires replacement and failure to replace the sleeve could result in contamination from the worn elastomer migrating into the pump reservoir cavity or loss of ability to properly engage and torque the separate threaded sleeve. Still further, the separate threaded sleeve could also be lost or misplaced, since it is not an integral part of either the reservoir, line set or pump.

In yet other systems and methods, the O-ring used to seal the space between the reservoir, connector and the pump reservoir cavity can be located within the pump reservoir cavity, and needs to be replaced periodically by the user for proper operation. However, removal of the O-ring can be difficult for some users with limited dexterity, and improper removal of the O-ring can result in O-ring contamination migrating into the pump reservoir cavity or depending on the O-ring removal tool, can result in damage to the O-ring groove which retains the O-ring in the pump reservoir cavity. Ultimately, this damage can impact dosing or pump performance. Further, O-ring wear can occur which may not be noticeable to the user, causing O-ring particulates to enter the pump reservoir cavity or loss of sealing capabilities of the O-ring and migration of contaminates into the pump reservoir cavity.

Still further, the connection features and procedures that are used in such conventional infusion pumps include one or more of two-start threads, detent grooves, and a single thread. Accordingly, such systems require a certain degree of phase alignment for connecting the reservoir to the infusion pump. For example, being "in phase" means that the rotational (angular) or Cartesian (x, y) relationship between the features is the same on every pump, i.e. the threads start at the same angular increment from a detent groove on every pump. Accordingly, many components of such systems cannot be interchanged.

Accordingly, a need exists for a system and method of infusion pump management having improved human factors for reservoir and pump connection, and providing a reservoir and connector that can be easily engaged with all of the currently marketed infusion pumps.

SUMMARY OF THE INVENTION

An object of the present invention is to substantially solve the above and other problems and difficulties, and provide reservoir designs, constructions and implementations to adapt to different configurations of infusion pumps and line sets that may be encountered, maximize ease of use, while also maintaining function.

Another object of the present invention is to provide line set designs, constructions and implementations to adapt to different configurations of infusion pumps, connectors and reservoirs that may be encountered, maximize ease of use, while also maintaining function.

Another object of the present invention is to provide straight-line, push-on type connector designs, constructions and implementations to adapt to different configurations of infusion pumps, reservoirs and line sets that may be encountered, maximize ease of use, while also maintaining function.

Another object of the present invention is to provide reservoir designs, constructions and implementations to adapt to different configurations of infusion pumps, connectors and line sets that may be encountered, maximize ease of use, while also maintaining function.

Another object of the present invention is to provide straight-line, push-on type connector designs, constructions and implementations to releasably secure a reservoir within any number of infusion pump body configurations using only a simple, straight-line push-on motion.

Another object of the present invention is to provide straight-line, push-on type connector designs, constructions and implementations to allow coupling of a standard Luer fitting with a reservoir releasably secured within any number of infusion pump body configurations.

Another object of the present invention is to provide straight-line, push-on type connector designs, constructions and implementations to allow coupling of a custom Luer fitting with a reservoir releasably secured within any number of infusion pump body configurations and prevent coupling of a standard Luer fitting with the reservoir.

Another object of the present invention is to provide a custom Luer fitting with a hydrophobic membrane therein for air ingress and egress when coupled with a reservoir, and an adapter with a hydrophobic membrane therein for air ingress and egress for use with a standard Luer fitting coupled with a reservoir.

These and other objects are substantially achieved by providing a reservoir and straight-line, push-on connector assembly for connecting the reservoir and one of a standard Luer line set and a custom Luer line set to any number of infusion pump configurations using a simple straight-line, push-on motion, wherein the push-on connector assembly is provided and configured to secure the line set and reservoir with the infusion pump. One simple straight-line, push-on motion, preferably performed by gripping the expander sleeve, places and secures the reservoir (i.e., locates the reservoir on the x, y, and z axes) in the pump reservoir cavity, and one simple straight-line, pull-off motion releases and removes the reservoir from the pump reservoir cavity. Rotational orientation is not required for proper connection, pump engagement, or pump function, and any pulling of the tube set will not release the reservoir as the expansion sleeve through which the tube set is routed is not moved from the securing position by tension on the tube set or Luer fitting To do so, exemplary embodiments of the present invention comprise one or more of a reservoir with integral engagement features, a moveable expander sleeve that slides within a portion of the reservoir and secures one or more of the integral engagement features into mating or other contact surface features of an insulin pump reservoir opening once the reservoir has been placed into the reservoir opening of the infusion pump. The exemplary embodiments of the present invention further comprise a system and method to connect either a standard Luer connector to the reservoir by providing an adapter with a hydrophobic membrane therein, or connect a non-standard Luer connector with a hydrophobic membrane therein to the reservoir, to provide insulin therapy at a site remote from the pump.

BRIEF DESCRIPTION OF THE DRAWINGS

The various objects, advantages and novel features of the exemplary embodiments of the present invention will be more readily appreciated from the following detailed description when read in conjunction with the appended drawings, in which:

FIGS. 13-15 are enlarged perspective views of the third embodiment of a reservoir and straight-line, push-on connector assembly showing another exemplary contoured expander sleeve gripping surface, and an unseated position indicator in accordance with an embodiment of the present invention;

Throughout the drawings, like reference numerals will be understood to refer to like parts, components and structures.

DETAILED DESCRIPTION OF THE EXEMPLARY EMBODIMENTS

Figure 1A:
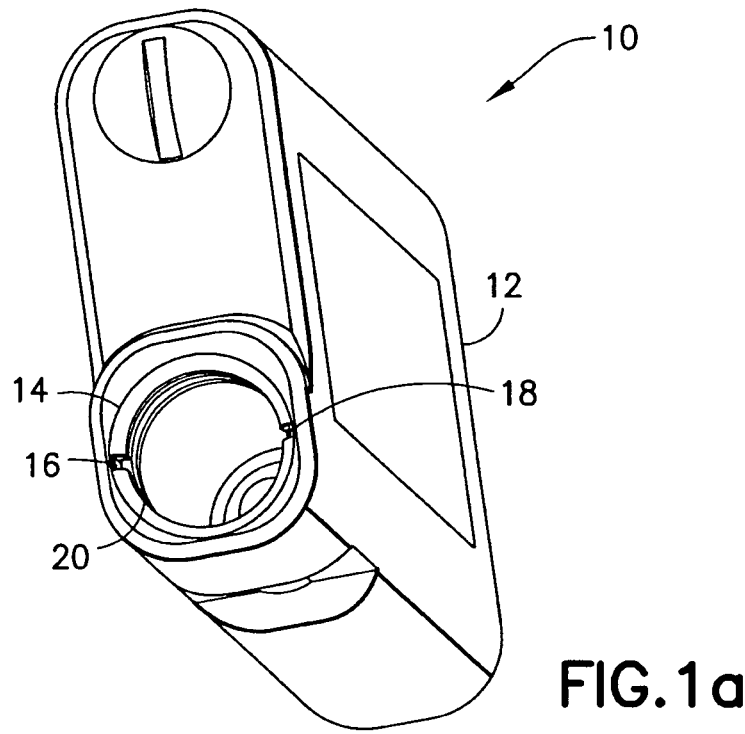
FIG. 1 are perspective views of an infusion pump which can interface with one or more exemplary elements of the present invention.

As will be appreciated by one skilled in the art, there are numerous ways of carrying out the examples, improvements and arrangements of devices disclosed herein. Although reference will be made to the exemplary embodiments depicted in the drawings and the following descriptions, the embodiments disclosed herein are not meant to be exhaustive of the various alternative designs and embodiments that are encompassed by the present invention.

As noted above, a need exists for a system and method of infusion pump management having improved human factors for the reservoir and pump connection, and providing a reservoir and connector that can engage with all of the currently marketed infusion pumps. To substantially solve these and other problems, an exemplary reservoir and straight-line, push-on connector assembly are provided to secure a reservoir within any type of infusion pump using a simple, straight-line, push motion, and provide an adapter with a hydrophobic membrane therein to enable the use of currently marketed products that have standard Luer connectors. The exemplary reservoir and straight-line, push-on connector assembly can also be designed to allow the use of a line set that that has a non-standard or custom/proprietary Luer line connection to inhibit the use of currently marketed products with standard Luer connectors.

In embodiments of the present invention, one simple straight-line, push-on motion, preferably performed by gripping the expander sleeve, places and secures the reservoir (i.e., locates the reservoir on the x, y, and z axes) in the pump reservoir cavity, and one simple straight-line, pull-off motion releases and removes the reservoir from the pump reservoir cavity. Rotational orientation is not required for proper connection, pump engagement, or pump function, and any pulling of the tube set will not release the reservoir as the expansion sleeve through which the tube set is routed is not moved from the securing position by tension on the tube set or Luer fitting.

The exemplary reservoir and straight-line, push-on connector assembly can be configured for insertion into any currently marketed infusion pump, and further configured to mate with or otherwise secure threads, detents, and/or any number of other mechanical interfaces in the reservoir opening of the infusion pump, and thereby enable secured connection of a reservoir and line set with any currently marketed infusion pump. These exemplary reservoir and straight-line, push-on connector assemblies can comprise a number of features for such engagement and use therein, including, but not limited to, the provision of a reservoir and a straight-line, push-on type expander sleeve to secure the reservoir within the reservoir opening of an infusion pump using only a simple straight-line motion, and the provision of hydrophobic membranes located in a suitable location to allow line set attachment and use, such as in a custom Luer connector, or in an expander sleeve or adapter to permit the use of a standard Luer connector.

In such exemplary embodiments of the present invention, the attachment method of the reservoir and straight-line, push-on connector assemblies can be performed by a simple straight-line user motion, eliminating the need for twisting and locking actions for both insertion and removal of the reservoir and connector as associated with conventional systems and methods. The same motion to push the reservoir into the pump, also locks the reservoir within the pump. Unlike current reservoirs on the market, the exemplary embodiments of the present invention do not need to be twisted to lock the reservoir within the pump.

That is, in the exemplary embodiments of the present invention, a user can simply align a reservoir with an infusion pump reservoir opening and slide the reservoir into the infusion pump reservoir opening using a straight-line motion only such that one or more detents on the reservoir engage recesses in the infusion pump opening to inhibit spiral disassembly or movement. The user can then slide, advance, engage or seat the expander sleeve fitting into the reservoir and/or infusion pump reservoir opening such that one or more expanding latches or locking features of the reservoir engage threads or similar features, or other inner surfaces in the infusion pump reservoir opening to inhibit linear disassembly or movement. A line set with either a standard Luer fitting or a custom Luer fitting can then be installed with the accessible reservoir end through the expander sleeve. In the case of a standard Luer fitting, an adapter is provided between the reservoir and the standard Luer fitting to provide the hydrophobic membrane required for pressure equilibrium. In the case of the custom Luer fitting, the hydrophobic membrane can provided in the custom Luer fitting or expander sleeve.

In the exemplary embodiments of the present invention, the hydrophobic membrane can be provided in one or more of the custom Luer fitting, the adapter, and the expander sleeve. In the case of the custom Luer fitting, the hydrophobic membrane can be located in a flange or other body element of the custom Luer fitting. In the case of an adapter, the hydrophobic membrane can be located in a body element of the flange of the adapter. In the case of an expander sleeve, the hydrophobic membrane can be located in a flange of the expander sleeve, a side wall of the expander sleeve or other body element of the expander sleeve. In each case, an opening is provide for pressure equilibrium and having at least a partially surrounding flat surface on which the hydrophobic membrane is secured. The hydrophobic membrane is preferably provided as a covering for the opening and provides a pathway for air ingress and egress for pressure equilibrium. Such exemplary features are easily moldable, and the hydrophobic membrane can be heat staked or bonded into position with UV cured adhesive or epoxy. An exemplary hydrophobic membrane is comprised of a Polytetrafluoroethylene (PTFE) or expanded Polytetrafluoroethylene (ePTFE) material, but is not limited thereto.

The exemplary embodiments of the present device described below illustrate a number of features and elements in the areas of reservoir and reservoir connector assemblies, and Luer and line set construction and implementation, such that a reservoir can adapt to different configurations of infusion pumps, connectors and line sets that may be encountered, maximize ease of use by eliminating and replacing rotational steps with a single, straight-line push and pull motion, while maintaining desirable form and function. An exemplary infusion pump is shown by way of the example in FIG. 1 which serves to introduce the embodiments of the present invention described in greater detail below.

Figure 1B:
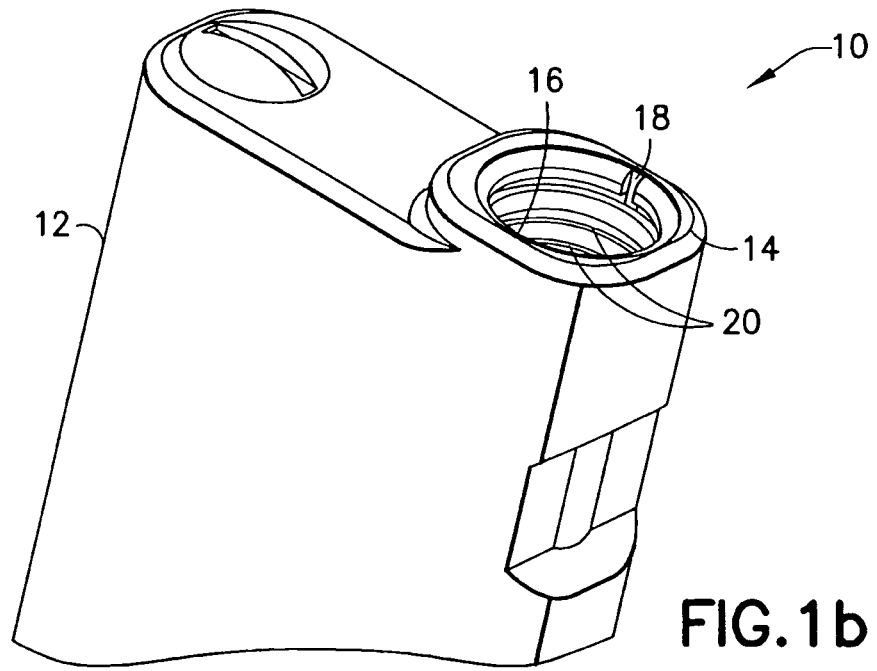
Figure 2:
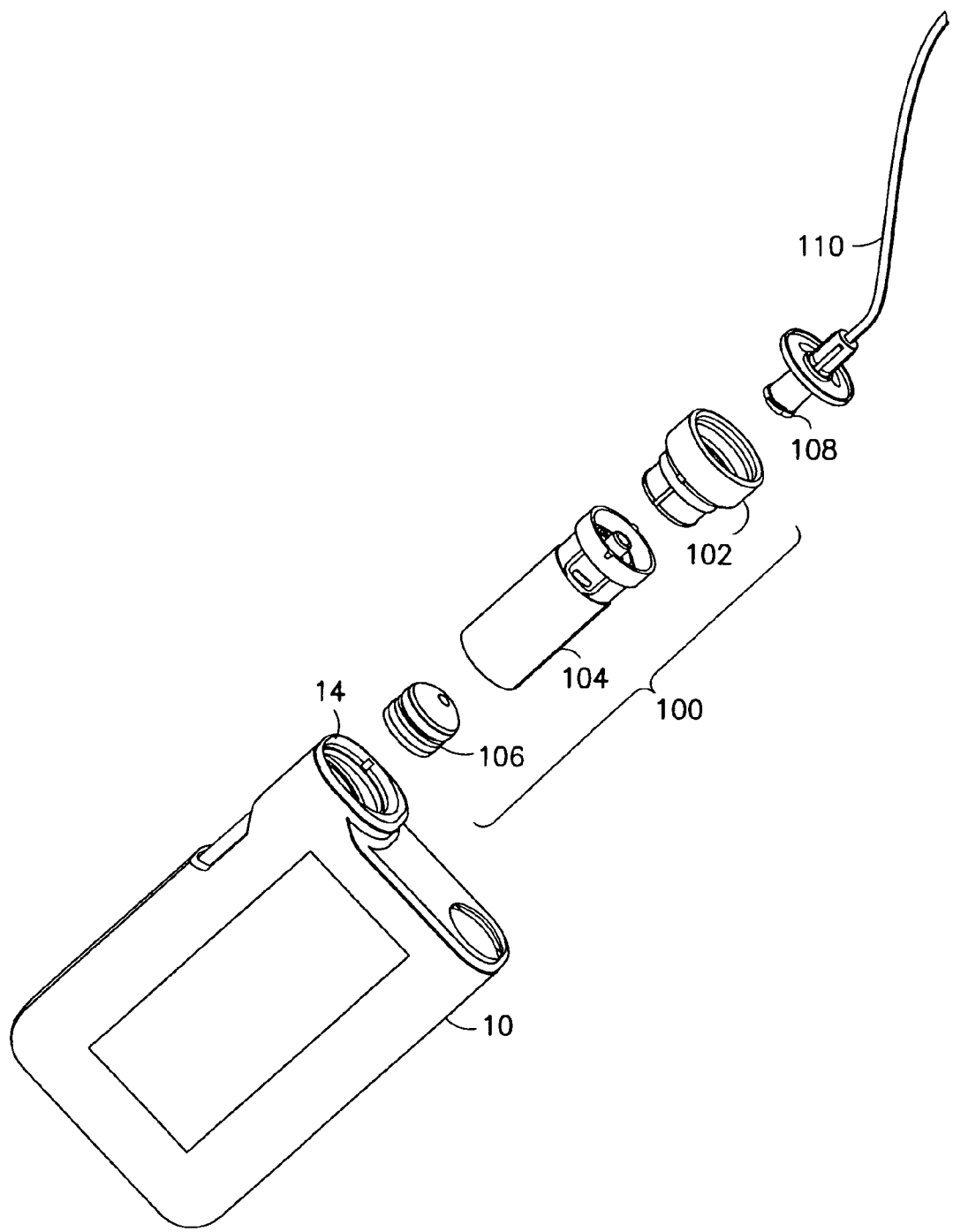
FIG. 2 is an exploded view of a first exemplary embodiment of a reservoir and straight-line, push-on connector assembly for interfacing a line set with a custom Luer connector having an integral hydrophobic membrane with the infusion pump of FIG. 1 in accordance with an embodiment of the present invention.

FIG. 1 illustrates an exemplary infusion pump 10 including the following features. Part (a) of FIG. 1 is a perspective view of the infusion pump 10, and part (b) of FIG. 1 is an enlarged view of the reservoir opening of the infusion pump 10 in greater detail. As shown in FIG. 1, the exemplary infusion pump 10 can comprise a body 12, and a reservoir opening 14 into which a reservoir can be positioned. In a conventional system and method, the user slides a reservoir into the reservoir opening 14 and then turns and threads a separate threaded sleeve with sufficient torque to check the threads and secure the reservoir. For disengagement, the user is required to unscrew the separate threaded sleeve, and then pull the reservoir from the pump reservoir cavity.

However, many infusion pumps are configured to receive and secure a reservoir in different ways, and using different threaded sleeves. That is, in many cases, a reservoir and tube set may not conform to an infusion pump of the user thereby preventing use. In the following description, a number of exemplary embodiments of a reservoir assembly, expander sleeve and line set are described in greater detail, which can be provided for use with the exemplary infusion pump 10 or any number of other similar devices. In doing so, the exemplary reservoir assembly, expander sleeve and line set constructions, or variations and combinations thereof, can be used to overcome different configurations of infusion pumps, reservoirs and line sets that may be encountered.

The infusion pump 10 comprises at least one reservoir opening 14 for receiving and containing a reservoir, such that the contents thereof are delivered to a user via an attached tube set. As known to those skilled in the art, the infusion pump 10 can include any number of features for user setting and control of medicament delivery, and such additional details of the infusion pump 10 are omitted herein for clarity. In the exemplary embodiment shown, the reservoir opening 14 is substantially cylindrical having a depth and diameter sufficient to receive and store therein a reservoir, and comprises slots or recesses 16 and 18 at or near an entry point to engage protrusions on the reservoir to, for example, prevent rotational movement of the reservoir once in position. The reservoir opening 14 can further comprise thread elements 20 to receive and engage thread elements on the reservoir or reservoir connector in a rotating manner to secure the elements within the reservoir opening 14. Still further, the reservoir opening 14 can comprise one or more of an O-ring pump seal, an O-ring contact surface and a female groove to serve one purpose or another, but which can be used by the exemplary embodiments described below.

To provide a more simplified and ergonomically desirable reservoir and connector that can be used with a large number of different infusion pumps, exemplary embodiments of the present invention provide a reservoir and straight-line, push-on connector assembly comprising at least one deflectable latches of the reservoir and an expander sleeve with over-molded seals, which can be inserted into the reservoir opening 14 of the infusion pump 10 with a simple straight-line, push-on motion. The basic features in the device described herein therefore can comprise a reservoir with an integral upper sleeve and moveable engagement features (i.e., latches, arms, wings, elements, and so forth), an expander sleeve, and over-molded seals on the expander sleeve. The basic features in the connection alternatives can comprise a line set connection with an adapter and a standard Luer connector, and a line set connection with a custom Luer connector.

In exemplary embodiments of the present invention, a straight-line, push-on connector assembly is provided in which a radial expansion of at least one component, resulting from axial advancement of a cam, tapered sleeve, expander sleeve, or other mechanical element, is used to engage and secure threads or similar features, or simply an inner wall surface, in the infusion pump reservoir opening 14 to inhibit linear disassembly or movement of the reservoir and the straight-line, push-on connector. The provision of such a connector assembly is configured to operate in a simple straight-line, push-on manner, and results from the consideration of ergonomic and other human factor engineering principles to simplify, eliminate and combine motions necessary for attachment. Further, by overmolding one or more seals into such a straight-line, push-on connector assembly, the part count is reduced in the connector assembly.

In one or more of the exemplary embodiments of the present invention, the reservoir is provided with an opening at one end to slidably receive the expander sleeve, which can be used to deflect at least one deflectable latches of the reservoir. The expander sleeve is slidable within the opening of the reservoir between two positions. In a first non-seated position, one or more expanding latches or locking features of the reservoir are not expanded such that insertion and removal of the reservoir can be easily performed, and a second seated position wherein the expanding latches or locking features of the reservoir as urged by the moving of the expander sleeve are expanded outward and engage and secure threads or similar features in the infusion pump reservoir opening to inhibit linear disassembly or movement. Detents on the reservoir can be provided to engage and secure the slots or recesses in the infusion pump reservoir opening to inhibit rotational movement.

A gripping surface on the expander sleeve permits the insertion and locking action, and the unlocking and removal action, using a single grip of the expander sleeve and a simple, straight-line motion. A cam or engagement profile on such an expander sleeve is also preferably designed to resist disassembly until a specific pull force is applied to the expander sleeve. A pull force to the tube set will not have any effect. That is, the locking feature is activated and deactivated solely by the expander sleeve. Tugs on the infusion set tube are transmitted harmlessly to the reservoir. The cam or engagement profile is also designed to provide an audible and/or tactile "click" or other sound or visual indication when the expander sleeve is completely advanced in one or both directions.

The expanding latches or locking features of the reservoir configured to engage the reservoir opening when urged by the movement of the expanding sleeve can comprise a simple protruding segment with only a single contact surface to engage and secure the mating male threads, female threads, or other grooves in the reservoir opening, i.e., the cross-section of the segment can be a triangle. In yet other exemplary embodiments of the present invention, the expanding latches or locking features of the reservoir piece can comprise an exemplary single-post engagement feature, two-post engagement feature, or a pad engagement feature that, once secured, inhibit removal of the connector assembly, and wherein each provides reservoir removal prevention at least to an extent provided by a threaded connection but without requiring any twisting movements for engagement or disengagement.

FIGS. 2-3 and 5-6 are views of a first exemplary embodiment of a reservoir and straight-line push connector assembly 100 for interfacing a line set with a custom Luer having an integral hydrophobic membrane with the infusion pump of FIG. 1 in accordance with an embodiment of the present invention. As noted in greater detail below, the exemplary embodiments of the present invention can be configured for use with a standard Luer connector by providing a hydrophobic membrane in an adapter or expander sleeve. The exemplary embodiments of the present invention can also be configured for use with a custom Luer connector with a hydrophobic membrane and prevent use with a standard Luer connector by, for example, providing dimensions of the connector that prevent use of the standard Luer connector. The first exemplary embodiment is configured for use with a custom Luer connector with a hydrophobic membrane and prevents use with a standard Luer connector by, for example, providing dimensions of the connector that prevent use of the standard Luer connector.

In the first exemplary embodiment, a reservoir 104 is configured to be slidably inserted into the reservoir opening 14 such that a plunger 106 of the reservoir 104 can be driven through actions of the infusion pump 10. Such actions are well known to those skilled in the art, and further description of the driving of the plunger 106 to expel the contents of the reservoir 104 are omitted for clarity. Detents 124 and 126 on the reservoir 104 are provided to engage and secure the slots or recesses 16 and 18 in the infusion pump reservoir opening to inhibit rotational movement.

Once the reservoir 104 is in position within the reservoir opening 14, an expander sleeve 102 can be either inserted into an opening of the accessible end of the reservoir 104, or can be previously assembled with the end of the reservoir 104 and simply seated as described in greater detail below, to thereby secure the reservoir 104 and expander sleeve 102 in the reservoir opening 14 of the infusion pump 10 using a simple straight-line, push-on motion. The expander sleeve 102 is slidable within the opening of the reservoir 104 between two positions. In a first non-seated position, one or more expanding latches or locking features 130 and 132 of the reservoir 104 are not expanded such that insertion and removal of the reservoir 104 can be easily performed, and a second seated position wherein the expanding latches or locking features 130 and 132 of the reservoir 104 as urged by the moving of the expander sleeve 102 are expanded outward and engage and secure threads or similar features in the infusion pump reservoir opening 14 to inhibit linear disassembly or movement.

At this time, a custom Luer connector 108 of a tube set 110 can be installed with the reservoir 104 for use. In yet other exemplary embodiments of the present invention, an adapter and a standard Luer connector of a tube set can be installed with the reservoir 104 for use.

Figure 3:
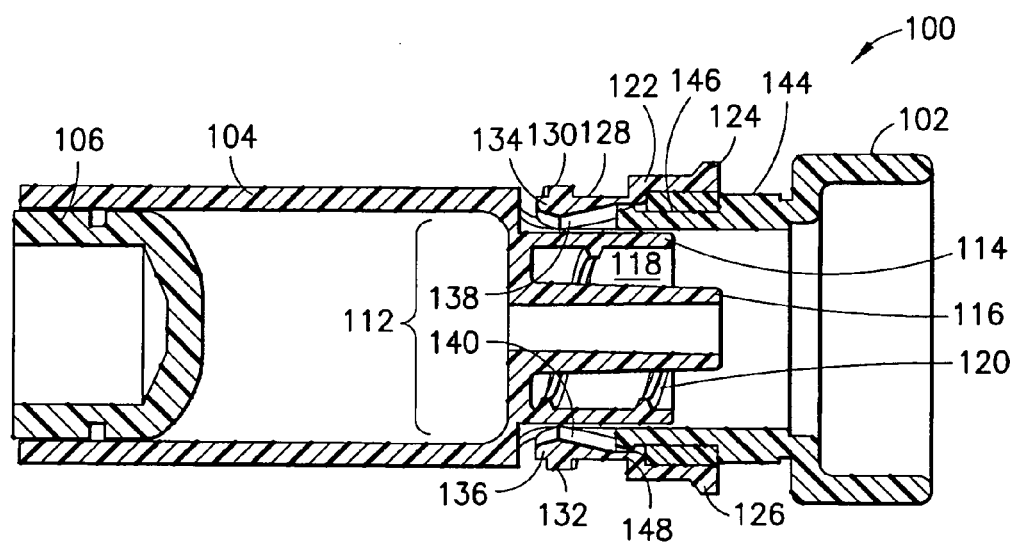
FIG. 3 is an enlarged sectional view of the assembled first embodiment of a reservoir and straight-line, push-on connector assembly for interfacing with the infusion pump of FIG. 1 in accordance with an embodiment of the present invention.

In the first exemplary embodiment of the present invention shown in greater detail in FIG. 3, the reservoir 104 contains the plunger 106 at a first end, and a connection means at a second end for receiving the custom Luer 108 and around which, slidably receiving the receiving the expander sleeve 102. Specifically, the second end of the reservoir 104 comprises a male Luer lock 112 as known to those skilled in the art. The male Luer lock 112 comprises an internally threaded outer circumference 114 surrounding an inner protrusion 116, and a space therebetween 118 sufficiently sized to receive and secure a female Luer fitting. Threads 120 are provided on an inner surface of the outer circumference 114 to secure the Luer fitting. In yet other embodiments of the present invention, the threads 120 and/or the outer circumference 114 can be omitted.

The reservoir further comprises an outer ring 122 to slidably receive the expander sleeve 102 in a space provided between the outer ring 122 and the outer circumference 114 of the Luer lock 112. The outer ring 122 is preferably formed as a part of the reservoir 104, of the same materials, to simplify construction and reduce the number of components.

At an end of the outer ring 122, one or more detents 124 and 126 can be provided to extend a slight distance from the outer ring 122 and serve to engage one or more similarly shaped openings in the reservoir opening 14, such as openings 16 and 18 shown in FIG. 1. In doing so, the engagement between the detents 124 and 126 with the openings inhibit spiral disassembly or movement of the reservoir 104 once in position.

The outer ring 122 further comprises a reduced diameter section 128 to provide clearance for one or more expanding latches or locking features 130 and 132 of the reservoir and which are provided on an outer surface of deflectable arms 134 and 136, respectively. In doing so, the features 130 and 132 while in a relaxed, non-deflected state, are at substantially a same diameter as the remaining reservoir 104. This allows the reservoir 104 to be easily placed with the reservoir opening of the pump. However, when deflected outwardly by the expander sleeve 102 as described in greater detail below, the features 130 and 132 engage any contacted surface within the reservoir opening 14, such as those provided by a threaded surface, and secure the reservoir 104 via features 130 and 132 and deflectable arms 134 and 136 to the contacted surface until the deflection is released. As described in greater detail below, such deflection is provided by slidably seating the expander sleeve 102 in the outer ring 122 of the reservoir 104.

Specifically, the features 130 and 132 are disposed upon the deflectable arms 134 and 136 which extend from the outer ring 122 of the reservoir 104, and which further comprise one or more inclined surfaces 138 and 140 at a side opposite the features 130 and 132. The inclined surfaces 138 and 140 are configured to engage the slidable insertion of the expander sleeve 102 such that the slidable movement of the expander sleeve 102 when seating can be used to contact the inclined surfaces 138 and 140, deflect the deflectable arms 134 and 136 of the outer ring 122 outward, such that the features 130 and 132 are forced outward to engage any contacted surface, such as those provided by a male threaded surface or female threaded surface within the opening 14 of the infusion pump 10, and secure the reservoir 104 to the contacted surface of the opening 14 of the infusion pump 10 to inhibit linear disassembly or movement of the reservoir 104 once in position until deflection is released.

Figure 4A:
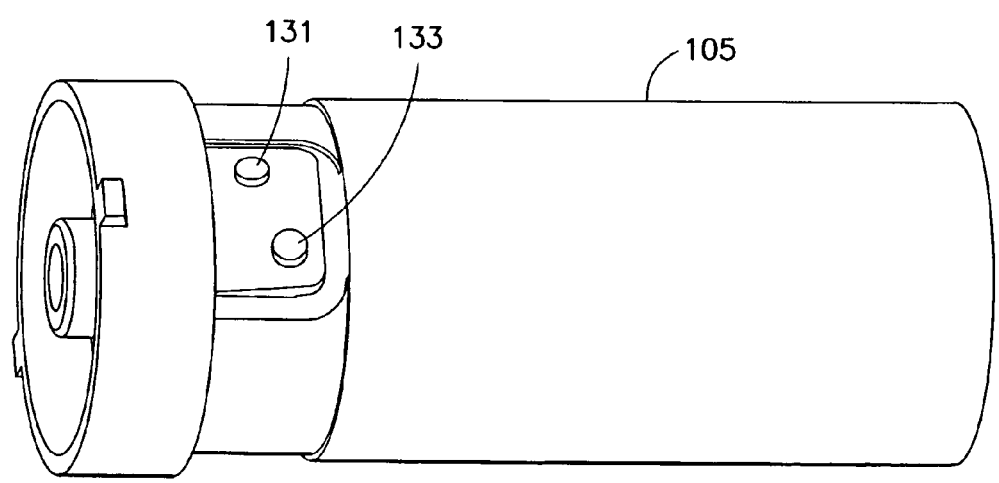
FIG. 4A is an enlarged view of an exemplary post-type engagement mechanism of a reservoir in accordance with an embodiment of the present invention.
Figure 4B:
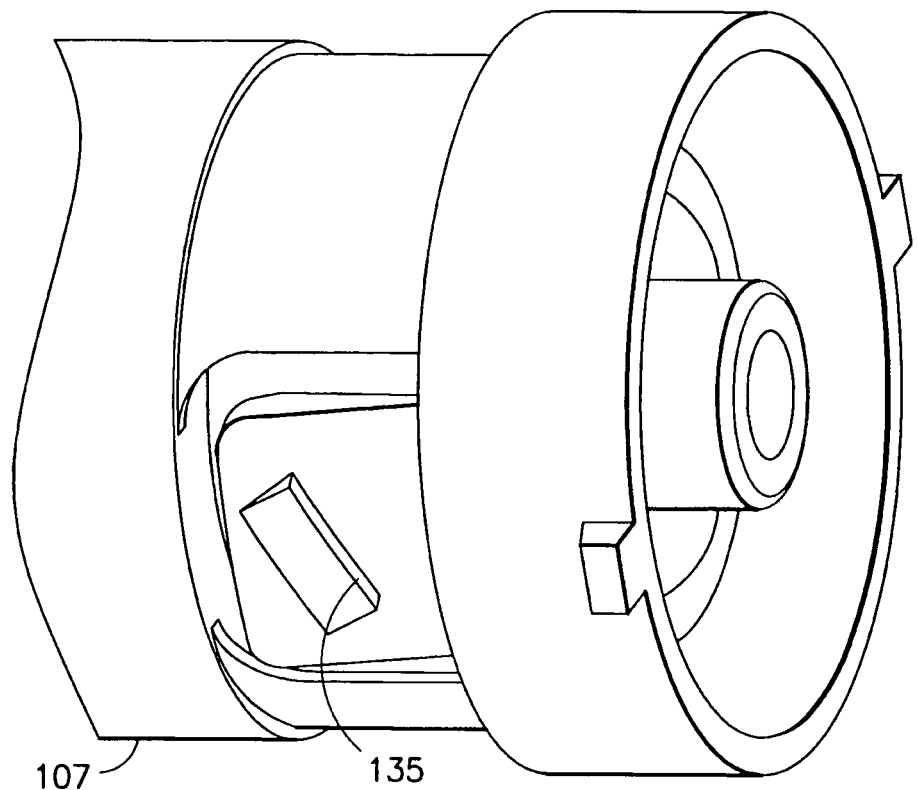
FIG. 4B is an enlarged view of an exemplary triangle-type engagement mechanism of a reservoir in accordance with an embodiment of the present invention.
Figure 4C:
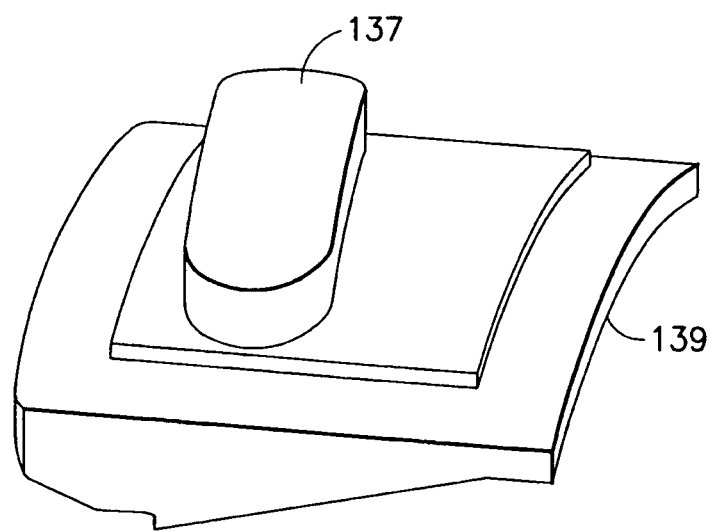
FIG. 4C is an enlarged view of an exemplary pad-type engagement mechanism of a reservoir in accordance with an embodiment of the present invention.

In the exemplary embodiment shown in FIG. 3, the features 130 and 132 are disposed upon the deflectable arms 134 and 136 and are comprised of simple segments to engage and secure surfaces, such as threads, in the reservoir opening 14. In yet other exemplary embodiments of the present invention, a single-post or two-post engagement feature, or a pad or triangular feature, can be disposed upon the deflectable arms 134 and 136, or even in place of the deflectable arms, to engage and secure surfaces, such as threads, in the reservoir opening. FIG. 4A illustrates examples of such two-post engagement features 131 and 133 of an alternate reservoir 105, FIG. 4B illustrates examples of a triangle-type engagement mechanism 135 of an alternate reservoir 107, and FIG. 4C illustrates examples of a pad-type engagement mechanism 137 of an alternate deflectable arm 139 wherein remaining features are as described in regard to the reservoir 104 above, to inhibit removal of the reservoir.

In yet other exemplary embodiments of the present invention, a single-post engagement feature can be used, or segment can be provided with only a single contact surface to engage and secure the mating male or female threads. In still other exemplary embodiments of the present invention, an engagement feature can be provided as a plurality of capturing-type (i.e., U-shaped, V-shaped, or similarly shaped) engagement features to engage/constrain both ends of the male or female threads. In doing so, a plurality of expanding latches can be provided. In still other exemplary embodiments of the present invention, an engagement feature can be provided as an elastomeric pad configured to grip the flat side-wall of the pump reservoir cavity adjacent to any male or female threads or where no such threads are found. Further, as described in greater detail below, the engagement feature 137 can be provided as "armless" pieces 139 captured between the reservoir and the infusion pump opening but engageable by the expansion sleeve and function in substantially the manner as described above.

In the case where one or more elastomer pads are used, increased engagement/disengagement forces can be provided by placing such elastomeric pads in or near the same locations as existing threads may be found, thereby allowing the elastomer of the pads to expand into the male or female threads. The elastomer can comprise a square, round, or otherwise shaped pad that overlaps the male or female threads, and a portion of the pad engages into the male or female threads.

Returning to FIG. 3, the detents 124 and 126 serve to engage one or more similarly shaped openings in the reservoir opening 14, such as openings 16 and 18 shown in FIG. 1 and in doing so, the engagement between the detents 124 and 126 with the openings inhibit spiral disassembly or movement of the reservoir 104. Once secured in such a manner, the elements 124 and 126 would need to be destroyed or sheared to rotate the reservoir. In effect, the elements 124 and 126 rotationally constrain the reservoir. The expanding latches or locking features 130 and 132 constrain the reservoir on the z axis, i.e. the reservoir cannot be pulled out or fall out of the pump cavity. The combination of both the rotational and z axis constraints locate and lock the reservoir to the infusion pump reservoir cavity.

Figure 11:
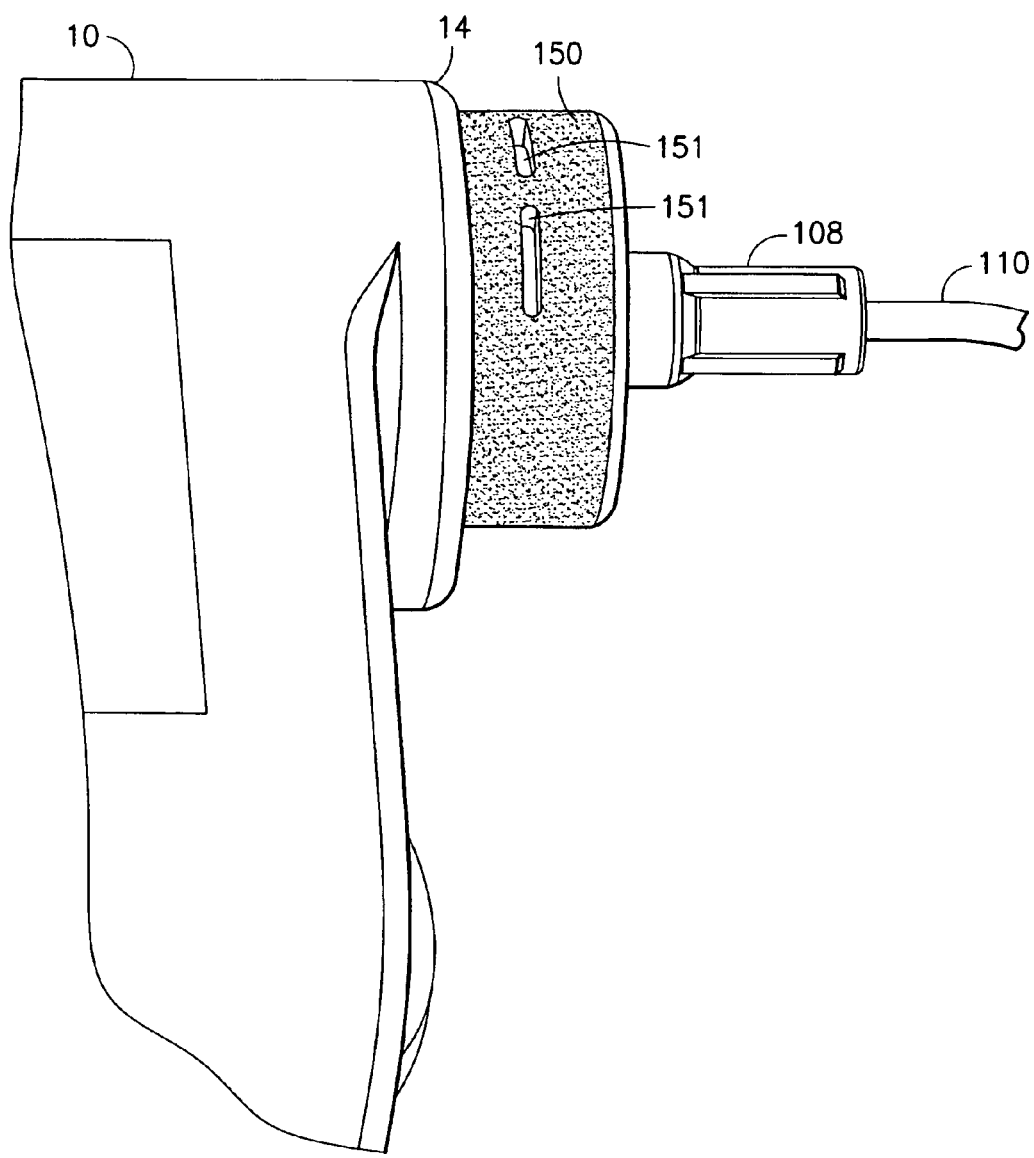
FIG. 11 is an enlarged view of an exemplary user-graspable surface of an expander sleeve in accordance with a third embodiment of the present invention.

The slidable movement of the expander sleeve 102 when seating forces a projection ring 148 of the expander sleeve 102 into contact with the inclined surfaces 138 and 140, and deflects the deflectable arms 134 and 136 of the outer ring 122 outward, such that the features 130 and 132 are forced outward to engage any contacted surface, such as those provided by a male or female threaded surface within the opening 14 of the infusion pump 10, and secure the reservoir 104. To accomplish the deflection, the expander sleeve 102 is provided having a first outer circumference 142 configured to be gripped by a user. The first outer circumference 142 is substantially circular with a constant diameter, and the outer surface of the first outer circumference 142 can be smooth or textured to facilitate gripping by the user. In yet another exemplary embodiment of the present invention shown in FIG. 11, illustrating modification to the expander sleeve, the outer user-graspable circumference of the expander sleeve 150 can be of a low profile and constant diameter, with a textured surface to facilitate gripping by the user. In yet other embodiments of the present invention as shown in FIGS. 12-15, the first outer circumference can be concave shaped as an alternative for further improving the grasp of the user. Further, the exemplary embodiment shown in FIG. 11 illustrates an example of the positioning of a hydrophobic membrane on the grasping diameter of the expander sleeve 150. In this case, the hydrophobic membrane covered openings 151 provide a pathway for air ingress and egress for pressure equalization. Such exemplary features are easily moldable, and the hydrophobic membrane can be heat staked or bonded with UV cured adhesive/epoxy for attachment. An exemplary hydrophobic membrane is comprised of a PTFE or ePTFE material, but is not limited thereto.

Returning to FIG. 3, the expander sleeve 102 is also provided having a second outer circumference segment 144 configured to slidably enter the outer ring 122 of the reservoir 104 and firmly hold the detents 124 and 126 in engagement with the one or more similarly shaped openings 16 and 18 in the reservoir opening 14 to inhibit spiral disassembly or movement of the reservoir 104 once in position. The expander sleeve 102 is still further provided having a third outer circumference segment 146 and having disposed at an end thereof the inclined projection ring 148 configured to slidably enter the outer ring 122 of the reservoir 104 and contact the inclined surfaces 138 and 140, to deflect the deflectable arms 134 and 136 of the outer ring 122 outward, such that the expanding latches or locking features 130 and 132 are forced outward to engage any contacted surface, such as those provided by a threaded surface within the reservoir opening 14, and secure the reservoir 104 to the contacted surface within the infusion pump to inhibit linear disassembly or movement of the reservoir 104 once in position until deflection is released.

The contacting surfaces of the inclined projection ring 148 and inclined surfaces 138 and 140 can be tapered at sufficient angles to ease insertion and deflection, and prevent the expander sleeve 102 from complete removal from the outer ring 122 of the reservoir 104. As described in greater detail below, the reservoir 104 can comprise an internal lip or ring feature to engage and retain the expander sleeve 102.

In at least one of the exemplary embodiments of the present invention, up to three seals can be provided to create a seal to eliminate contaminant ingress into the pump reservoir cavity. A first seal can be provided as an O-ring in the pump reservoir cavity or opening, which is configured to compress against the outside diameter (OD) of the reservoir, a second seal can be provided between the OD of the expander sleeve and the inside diameter (ID) of the upper portion of the reservoir, and a third seal can be provided between the ID of the expander sleeve and the OD of the flange feature on the custom Luer connector. To do so, at least one of the exemplary embodiments of the present invention includes an O-ring provided in the pump for the first seal, such as the O-ring 162 shown in FIG. 5, an O-ring provided in an ID of the expander sleeve for the second seal, such as the O-ring 168 shown in FIG. 5, and an O-ring provided in the expander sleeve opening for the third seal, such as the O-ring 164 shown in FIG. 5.

The exemplary expander sleeve 102 can also be overmolded with elastomer on surfaces to provide the first, second and third seals. In at least one other exemplary embodiment of the present invention, a standard Luer connector is incorporated in which the inner overmolded seal on the expander sleeve is located to seal against the outer wall of the Luer connection on the reservoir.

Figure 5:
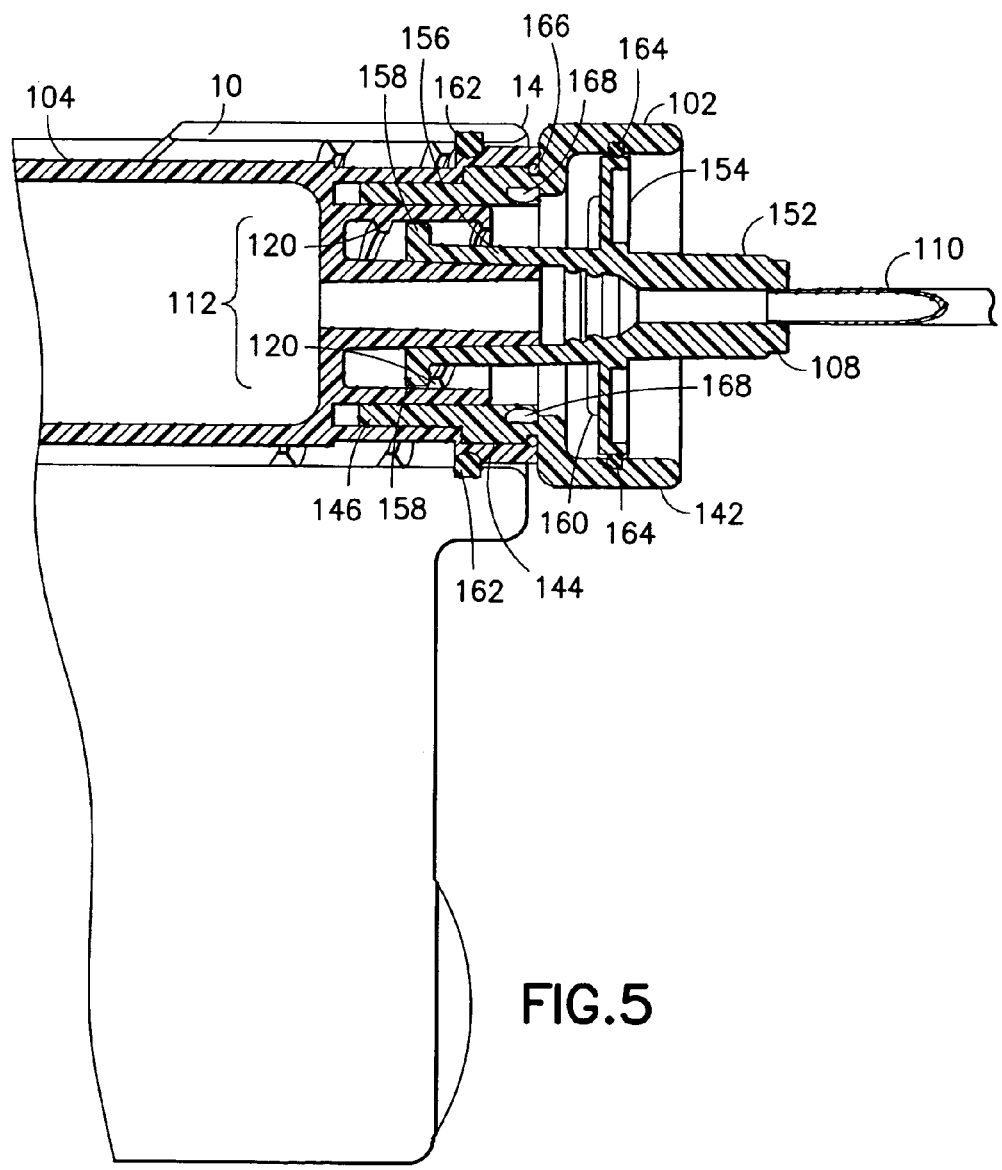
FIG. 5 is an enlarged sectional view of the assembled first embodiment of a reservoir and straight-line, push-on connector assembly inserted into the infusion pump of FIG. 1 in accordance with an embodiment of the present invention.

As shown in FIG. 5, the custom Luer connector 108 of the tube set 110 can be installed through the open inner diameter of the expander sleeve 102 and with the Luer lock of the reservoir 104 for use, and comprises a hydrophobic membrane 160 and sealing flange 154. A standard taper feature on the custom Luer connector 108 provides a seal and locking engagement with the reservoir 104, and the hydrophobic membrane 160 can be located in the flange 154 as described below. In this case, the custom Luer connector 108 comprises a first end 152, second end 156 and the flange 154 extending therefrom to seal the opening of the expander sleeve 102.

However, as known to those skilled in the art, air ingress and egress is needed to equilibrate pressure internal to the infusion pump reservoir cavity and ambient pressure. In exemplary embodiments of the present invention, the hydrophobic membrane 160 is incorporated into one or more of the expander sleeve 102, custom Luer connector 108, or as also shown in following embodiments, an adapter. For example, the hydrophobic membrane can be incorporated into a side wall or flange of the expander sleeve 102, a flange of the custom Luer connector 108, or a flange of an adapter which allows the use of a standard Luer connector. The hydrophobic membrane can be incorporated into the custom Luer connector, i.e., the line set connector, in the case of the first exemplary embodiment, and incorporated into an adapter or expander sleeve in the case of a second exemplary embodiment described below.

Figure 6:
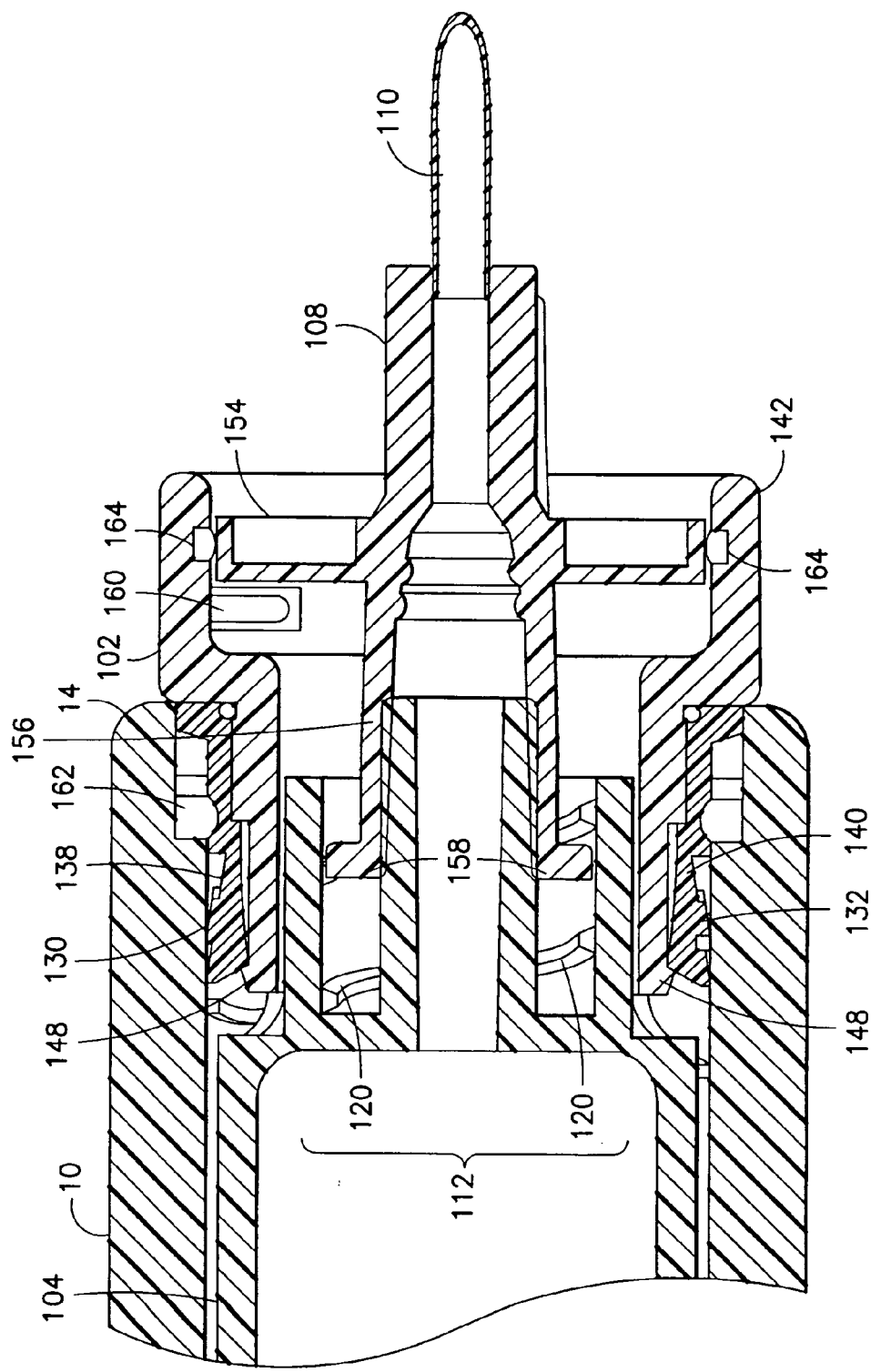
FIG. 6 is the enlarged sectional view of FIG. 5 rotated 90 degrees.
Figure 7:
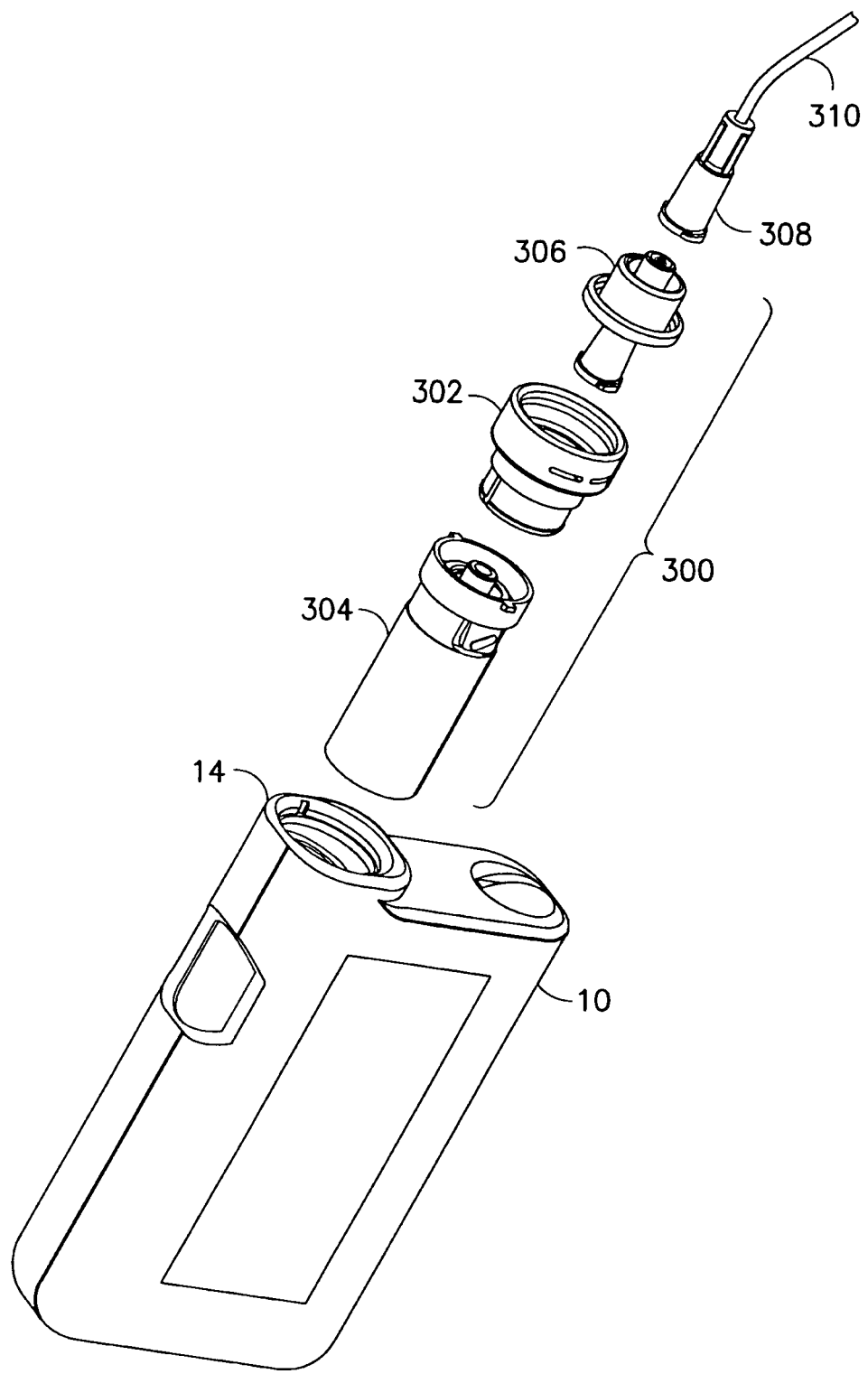
FIG. 7 is an exploded view of a second exemplary embodiment of a reservoir and straight-line, push-on connector assembly having a hydrophobic membrane incorporated into the expander sleeve for interfacing a line set with a standard Luer connector with the infusion pump of FIG. 1 in accordance with an embodiment of the present invention.
Figure 8:
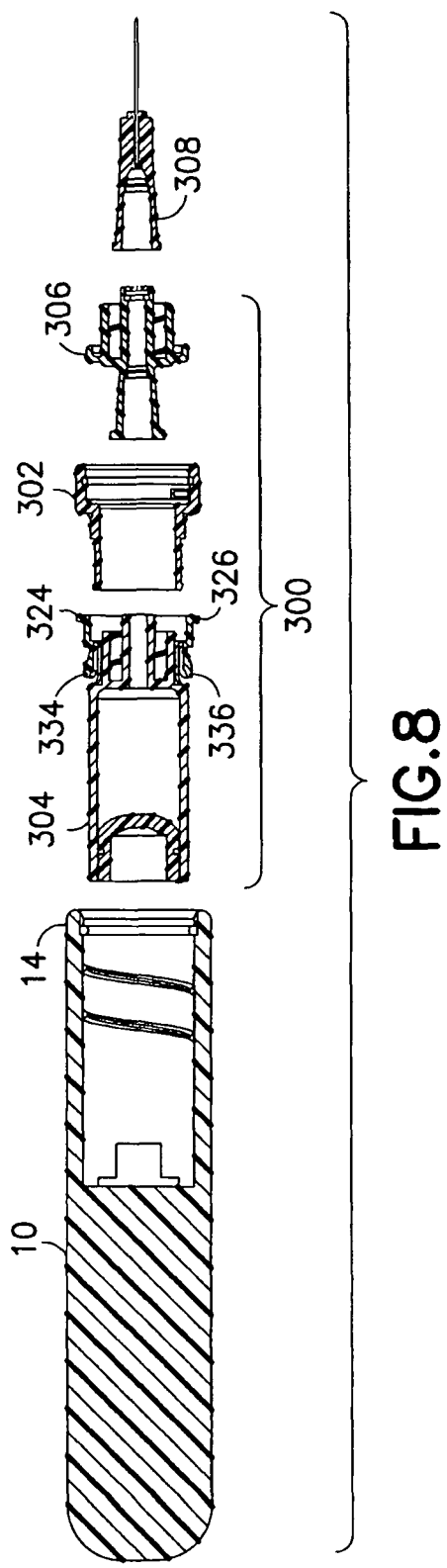
FIG. 8 is an exploded sectional view of the second embodiment of a reservoir and straight-line, push-on connector assembly for interfacing with the infusion pump of FIG. 1 in accordance with an embodiment of the present invention.
Figure 9:
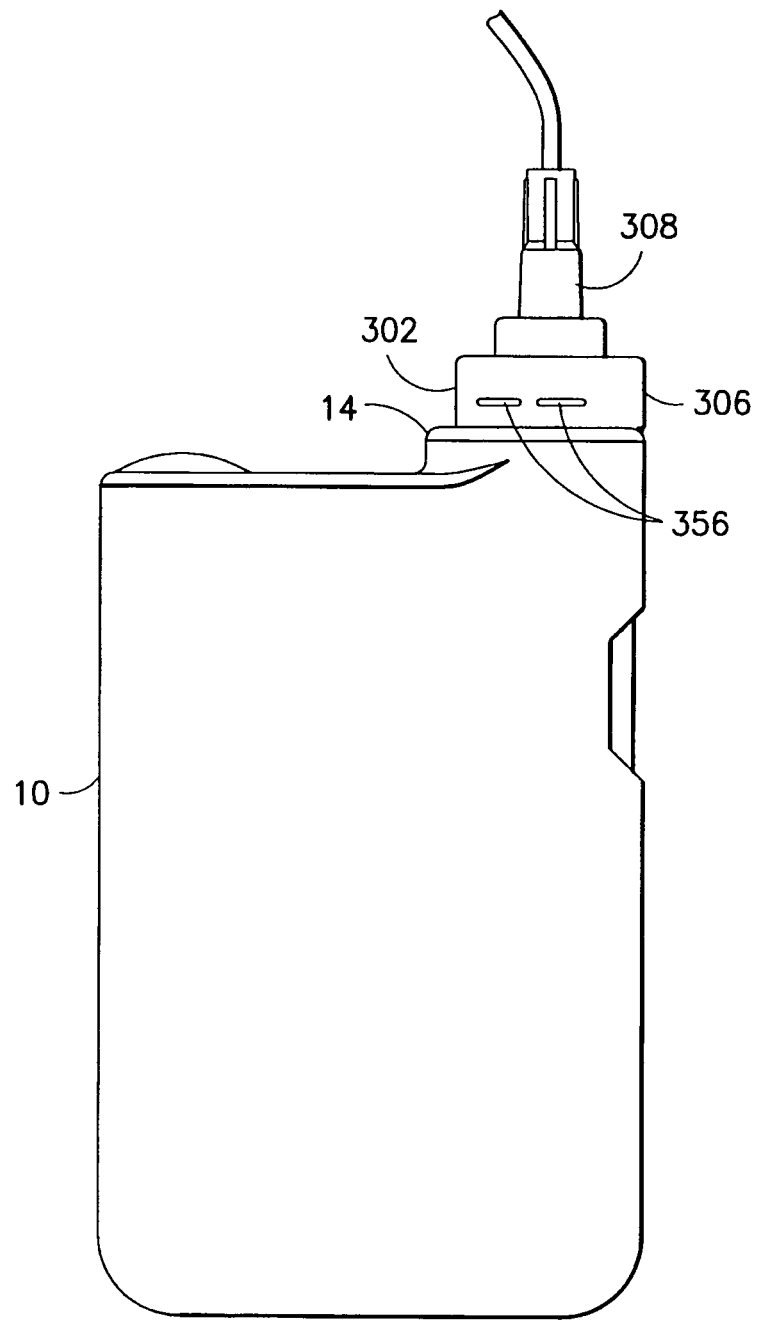
FIG. 9 is a perspective view of the assembled second embodiment of a reservoir and straight-line, push-on connector assembly inserted into the infusion pump of FIG. 1 in accordance with an embodiment of the present invention.

In the first exemplary embodiment shown in FIGS. 5 and 6, the hydrophobic membrane 160 is provided in the expander sleeve 102 or the custom Luer connector 108. For example, the hydrophobic membrane 160 can be located in either the side wall or the flange (i.e., the flat surface adjacent to the circumferential side wall) of the expander sleeve 102. The hydrophobic membrane can also be located in the flange (i.e., flat surface) 154 of the custom Luer connector 108. An exemplary hydrophobic membrane is comprised of a polytetrafluoroethylene (PTFE) or expanded polytetrafluoroethylene (ePTFE) material, but is not limited thereto. One or more openings are provided, covered by the hydrophobic membrane to allow air ingress and egress to equilibrate pressure internal to the infusion pump reservoir cavity and ambient pressure, while preventing contaminants, fluids and other undesired materials from entering the system.

Further, the diameter of the flange 154 of the custom Luer connector 108 is configured to substantially seal the opening of the expander sleeve 102 once in position. This can be further aided by the provision of the overmolded seal or O-ring 164 provided on an inner diameter of the opening of the expander sleeve 102 as shown in FIG. 5.

The second end 156 of the custom Luer connector 108 includes engagement tabs 158 to engage the threads 120 of the Luer connection 112 of the reservoir 104. The hydrophobic membrane 160 is positioned in the custom Luer connector 108 to allow air ingress and egress to equilibrate pressure internal to the infusion pump reservoir cavity and ambient pressure, while preventing contaminants, fluids and other undesired materials from entering the system. Further, the flange 154 of the custom Luer connector 108 provides a sealing surface between the ID of the expander sleeve 102 and the OD of the flange 154 on the custom Luer connector 108. Further, in an exemplary embodiment of the present invention, the length, width, height, diameter or other dimension of the expander sleeve 102 can be configured to inhibit the use of a standard Luer connector, which has a fixed height, and allow only the use of the custom Luer connector 108.

In contrast to the first exemplary embodiment described above, the second exemplary embodiment is configured for use with a standard Luer connector by providing a hydrophobic membrane in an adapter or expander sleeve. In doing so, the second exemplary embodiment comprises the adapter 306 to allow the use of a standard Luer fitting. However, the hydrophobic membrane must be provided elsewhere, such as in the adapter 306 or expander sleeve 302, as the standard Luer fitting 308 lacks such a hydrophobic membrane. As noted above, air ingress and egress is needed to equilibrate pressure internal to the infusion pump reservoir cavity and ambient pressure.

FIGS. 7-10 are views of the second exemplary embodiment of a reservoir and straight-line, push-on connector assembly 300 for interfacing a line set with a standard Luer connector but using an adapter and expander sleeve having an integral hydrophobic membrane with the infusion pump of FIG. 1 in accordance with an embodiment of the present invention. In the second exemplary embodiment shown, a reservoir 304 is configured to be slidably inserted into the reservoir opening 14 such that a plunger of the reservoir 304 can be driven through actions of the infusion pump 10. Detents 324 and 326 of the reservoir 304 are provided to engage grooves of the reservoir opening, and arms 334 and 336 are outwardly displaceable to engage the inner walls of the reservoir opening 14.

Once in position, an expander sleeve 302 can be either inserted into an opening of the accessible end of the reservoir 304, or can be previously assembled with the end of the reservoir 304 and simply seated as described above, to thereby secure the reservoir 304 in the reservoir opening 14 of the infusion pump 10 with a simple straight-line, push-on motion. The function and features of the exemplary second embodiment are substantially the same as described above in regard to the first exemplary embodiment with the addition of the hydrophobic membrane in the expander sleeve 302, and the adapter 306 which permits the use of a standard Luer fitting 308 in place of the custom Luer fitting of the first embodiment. Specifically, the adapter 306 is installed with the reservoir 304, and the standard Luer connector 308 of the tube set 310 can be installed with the adapter 306 for use.

Figure 10:
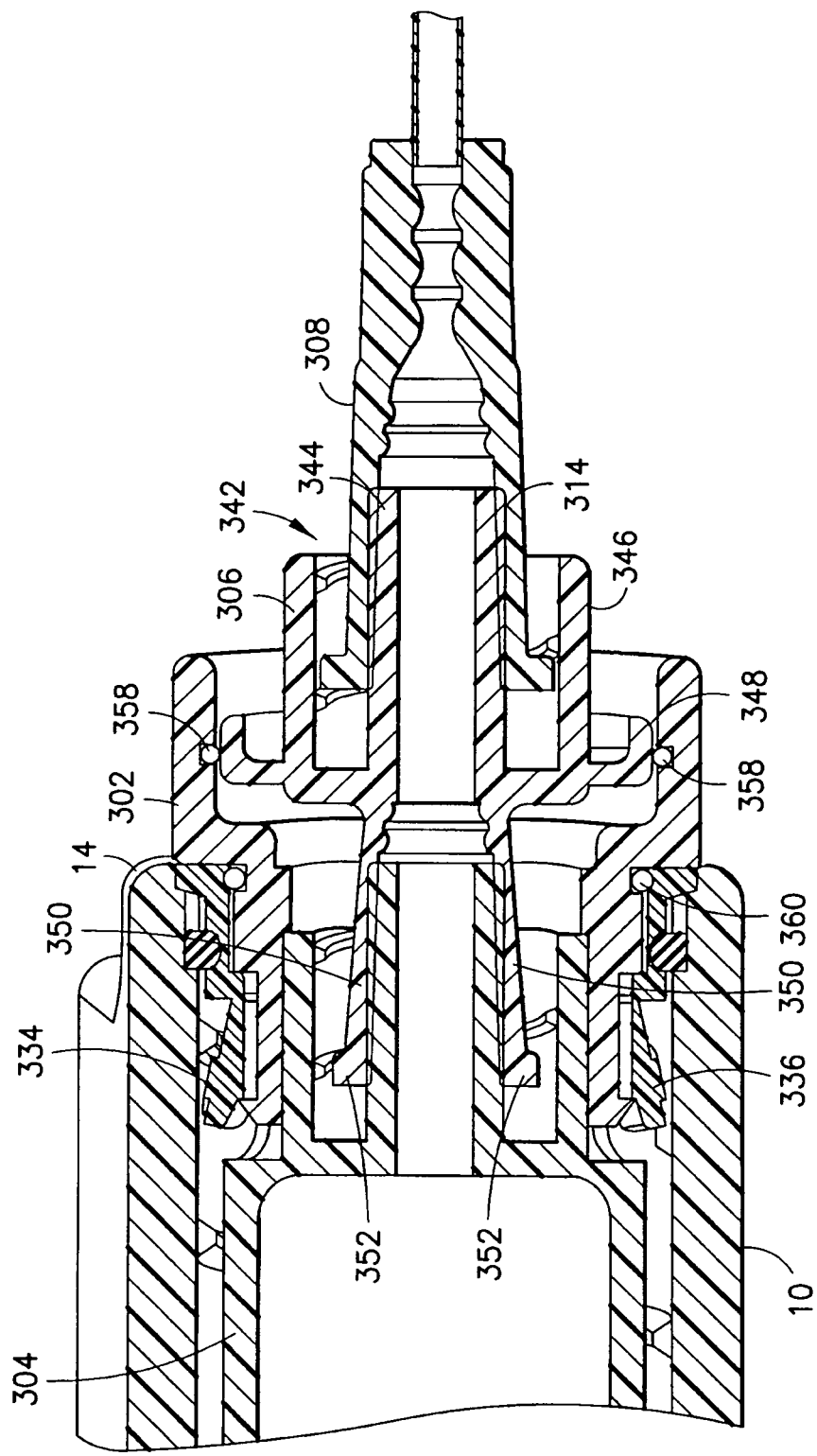
FIG. 10 is an enlarged sectional view of the assembled second embodiment of a reservoir and straight-line, push-on connector assembly inserted into the infusion pump of FIG. 1 in accordance with an embodiment of the present invention.

As shown in FIG. 10, the adapter 306 comprises a first end 342 to receive the standard Luer connector 308. The remaining elements of the adapter 306 include the inner barrel 344 and outer threaded barrel 346, and the flange 348 extending therefrom to seal the opening of the expander sleeve 302 assembly. The second end includes the barrel 350 and engagement tabs 352 to engage the threads of the Luer connection of the reservoir 304. The threads of the adapter 306 and the Luer connector 308 are configured in the same securing direction such that engagement secures the loosest connection first, but each engagement is secured in a single rotational motion. Further, in an exemplary embodiment of the present invention, the length, width, height, diameter or other dimension of the expander sleeve 302 can be configured to inhibit the use of a standard Luer connector, which has a fixed height, directly with the reservoir 304, and require the use of the adapter 306.

In the second exemplary embodiment, a hydrophobic membrane can be provided in the adapter 306 or the expander sleeve 302. The exemplary embodiment shown in FIGS. 7-10 illustrates an example of the positioning of a hydrophobic membrane on the grasping diameter of the expander sleeve 302. In this case, the hydrophobic membrane covered openings 356 provide a pathway for air ingress and egress for pressure equalization. A flat surface can be provided surrounding the openings 356 on the inner surface of the grasping diameter of the expander sleeve 302 on which to attach the hydrophobic membrane. As noted above, such exemplary features are easily moldable, and the hydrophobic membrane can be heat staked or bonded with UV cured adhesive/epoxy for attachment. An exemplary hydrophobic membrane is comprised of a PTFE or ePTFE material, but is not limited thereto. The hydrophobic membrane is provided to allow air ingress and egress to equilibrate pressure internal to the infusion pump reservoir cavity and ambient pressure, while preventing contaminants, fluids and other undesired materials from entering the system.

Further, the adapter 306 is configured such that the inner overmolded seal or O-ring 358 on the expander sleeve 302 is located to seal against the outer wall of the flange 348 of the adapter 306. The diameter of the flange of the adapter 306 is configured to substantially seal the opening of the expander sleeve 302 once in position. This can be further aided in the provision of the overmolded seal or O-ring 358 provided on an ID of the opening of the expander sleeve 302 as shown in FIG. 10. Still further, as described in greater detail below, a warning or fault ring 360 is shown on an OD of the expander sleeve 302.

The above first exemplary embodiment of a reservoir and straight-line, push-on connector assembly uses a custom Luer connector having an integral hydrophobic membrane. The second exemplary embodiment of a reservoir and straight-line, push-on connector assembly uses an adapter and an expander sleeve having an integral hydrophobic membrane and a standard Luer connector. Further, in the first and second exemplary embodiments, the reservoir comprises deflectable arms and segments to engage and secure surfaces, such as threads, in the reservoir opening when the expander sleeve is seated. In yet other exemplary embodiments of the present invention, the deflectable arms can be replaced with an "armless" embodiment of the reservoir.

Figure 12A:
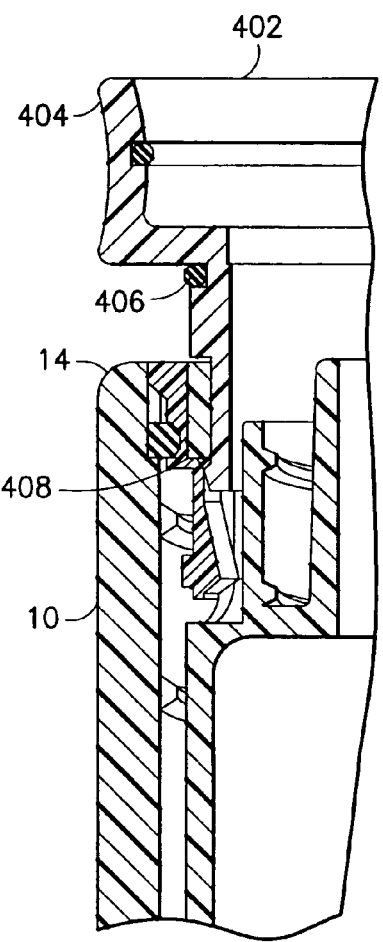
FIG. 12 are enlarged sectional views of the third embodiment of a reservoir and straight-line, push-on connector assembly showing another exemplary contoured expander sleeve gripping surface, and an unseated position indicator in accordance with an embodiment of the present invention.
Figure 12B:
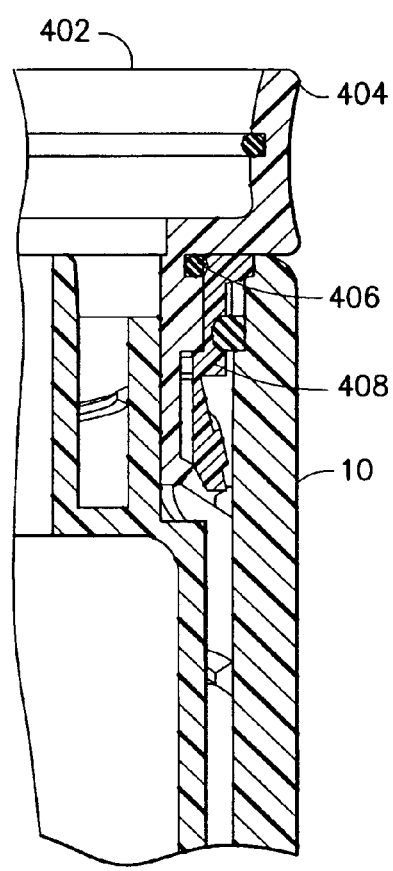
Figure 14:
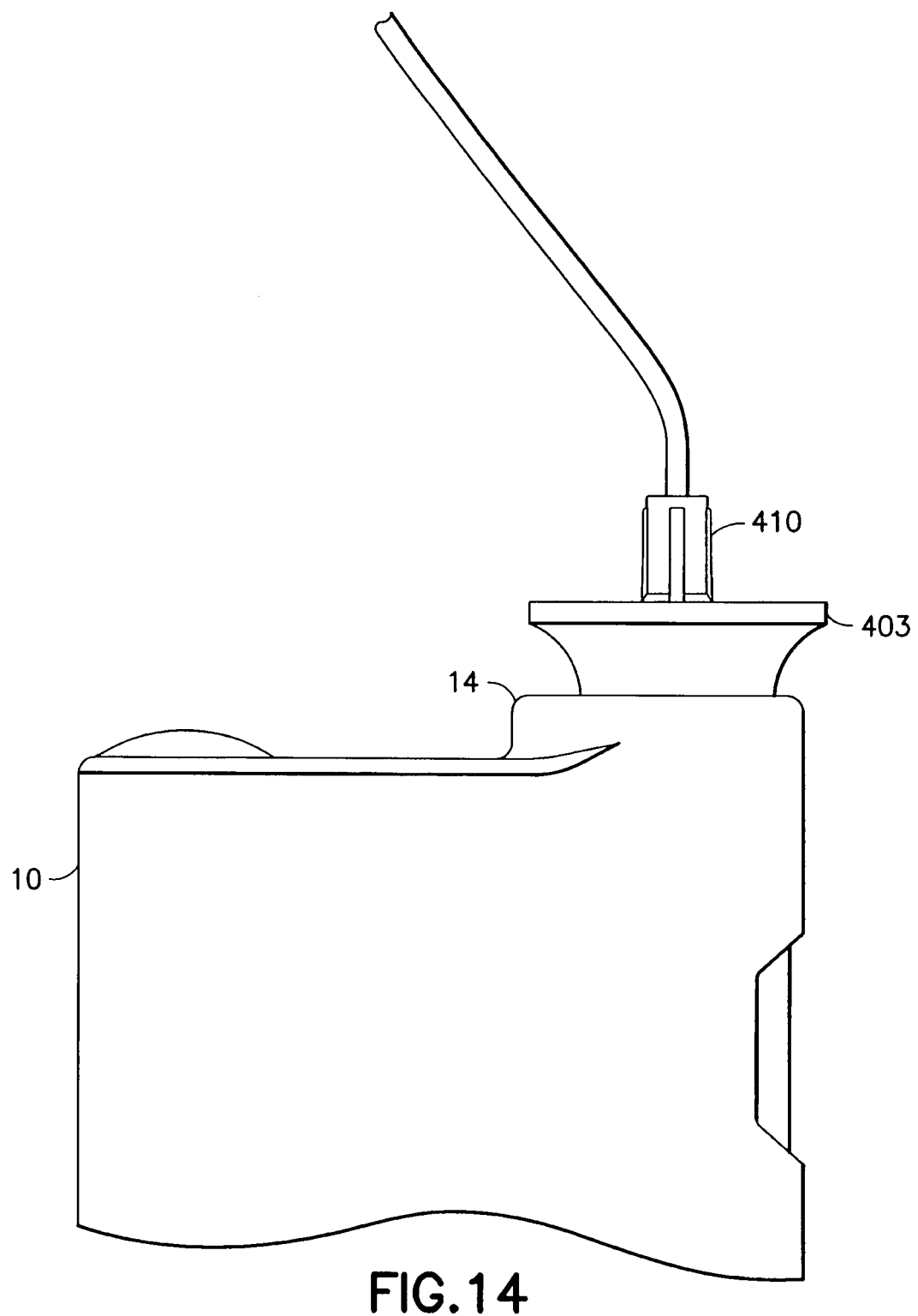
Figure 15:
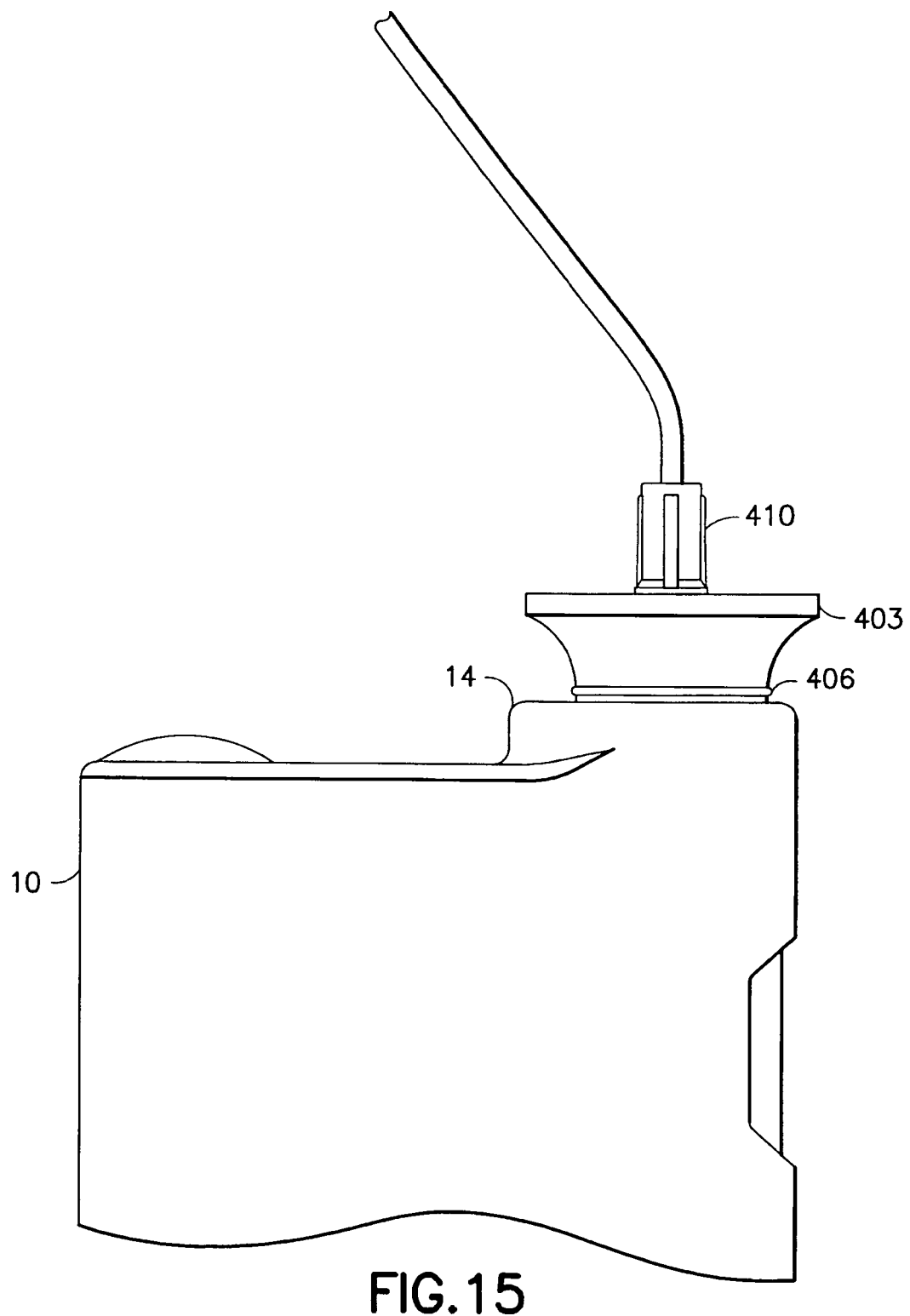

FIGS. 11-15 are views of third exemplary embodiments of a reservoir and straight-line, push-on connector assembly for interfacing a line set with the infusion pump of FIG. 1. The exemplary embodiment shown in FIG. 11 is substantially the same as the exemplary embodiments described above, but illustrates an expander sleeve 150 provided having an outer circumference with a textured surface to aid in gripping by a user. The exemplary embodiment shown in FIG. 12 is substantially the same as the exemplary embodiments described above, but illustrates an expander sleeve 402 provided having a first outer circumference 404 configured in a concave shape to aid in gripping by a user. The exemplary embodiment shown in FIGS. 13-15 is also substantially the same as the exemplary embodiments described above, but illustrates an expander sleeve 403 provided having a first outer circumference 404 configured in a trumpet shape to also aid in gripping by a user.

Further, the third embodiment illustrates an example of a fault ring indicator 406 that can be applied to any exemplary embodiment, and which remains exposed around a portion of the expander sleeve that would normally be engaged within the reservoir opening. In doing so, the fault ring indicator 406 can be provided to illustrate when the expander sleeve is not fully seated and therefore, the reservoir is not secured. When the expander sleeve has been fully seated, the fault ring indicator 406 is hidden within the reservoir opening. In an exemplary embodiment of the present invention, the fault ring indicator can be a band, mark or O-ring, and made in a bright color, such as red or orange, but is not limited thereto.

FIGS. 13-15 are additional views of the third embodiment further illustrating the fault ring indicator or mark showing an unseated expander sleeve 403 in a position when the reservoir is first placed into the pump reservoir cavity and the expander sleeve 402 is not advanced, a position when the expander sleeve 402 is fully advanced/engaged, and a position when the expander sleeve 402 has been partially unseated such as when there is incomplete engagement or when there is partial disengagement, thereby exposing the warning ring 406. The exemplary visible fault detection feature is provided to identify a fault condition, such as the movement of the expander sleeve which could result in the loosening of the engagement between the reservoir and the pump reservoir cavity. The visible, pronounced (i.e., bright red, fluorescent or contrasting) ring 406 or mark can be incorporated into the expander sleeve, and located on the expander sleeve at a point such that the fault detection ring 406 is exposed if the expander sleeve is not completely advanced. Where an integrated guide or other piece, as described in greater detail below, is provided in an exemplary embodiment of the present invention, the guide can be molded from a clear or opaque material or plastic, or have windows or spaces provided therein, to allow the user to see the fault detection ring or mark on the expander sleeve. In still other exemplary embodiments of the present invention the integrated guide can comprise a line or mark thereon that corresponds to the top outer surface around the pump reservoir cavity. Accordingly, to confirm complete engagement or maintained complete engagement, the user can simply look at the integrated guide to see if the line or mark and top surface are aligned.

Figure 16:
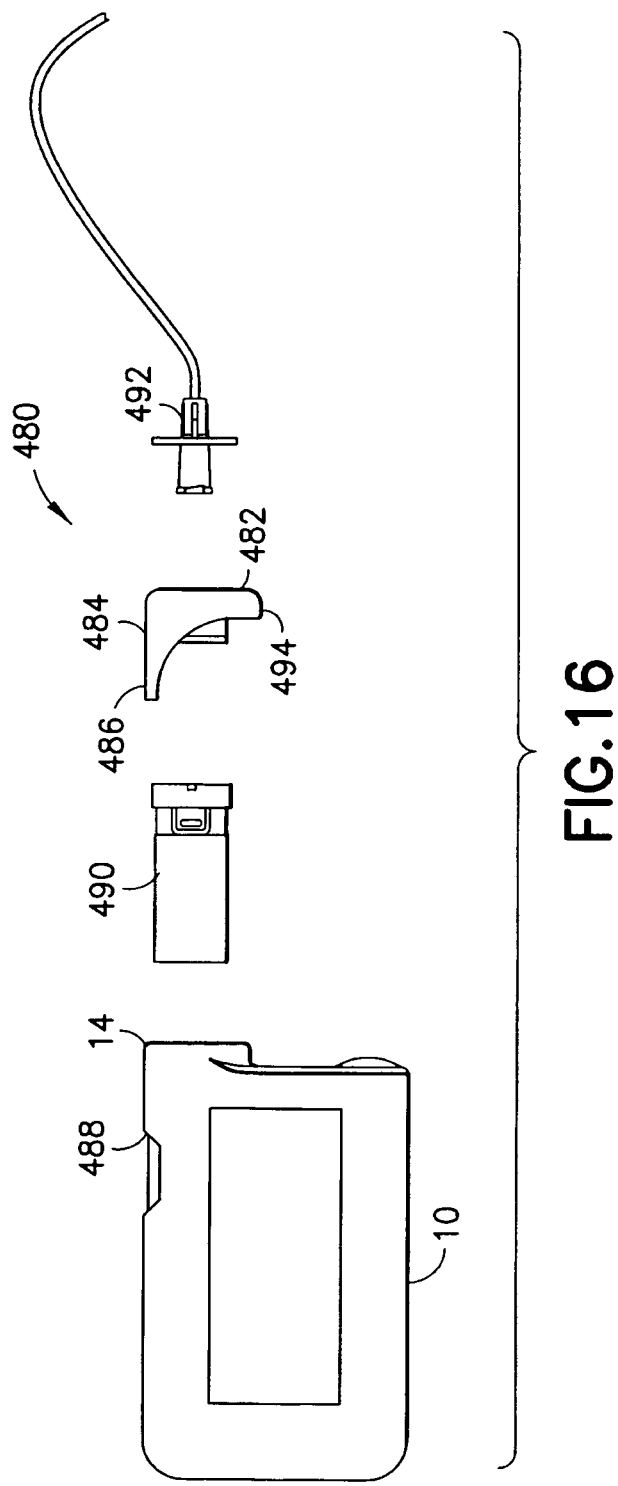
FIG. 16 is an exploded view of a fourth exemplary embodiment of an alignment guide, reservoir, and straight-line, push-on connector assembly for interfacing a line set with the infusion pump of FIG. 1 in accordance with an embodiment of the present invention.
Figure 17:
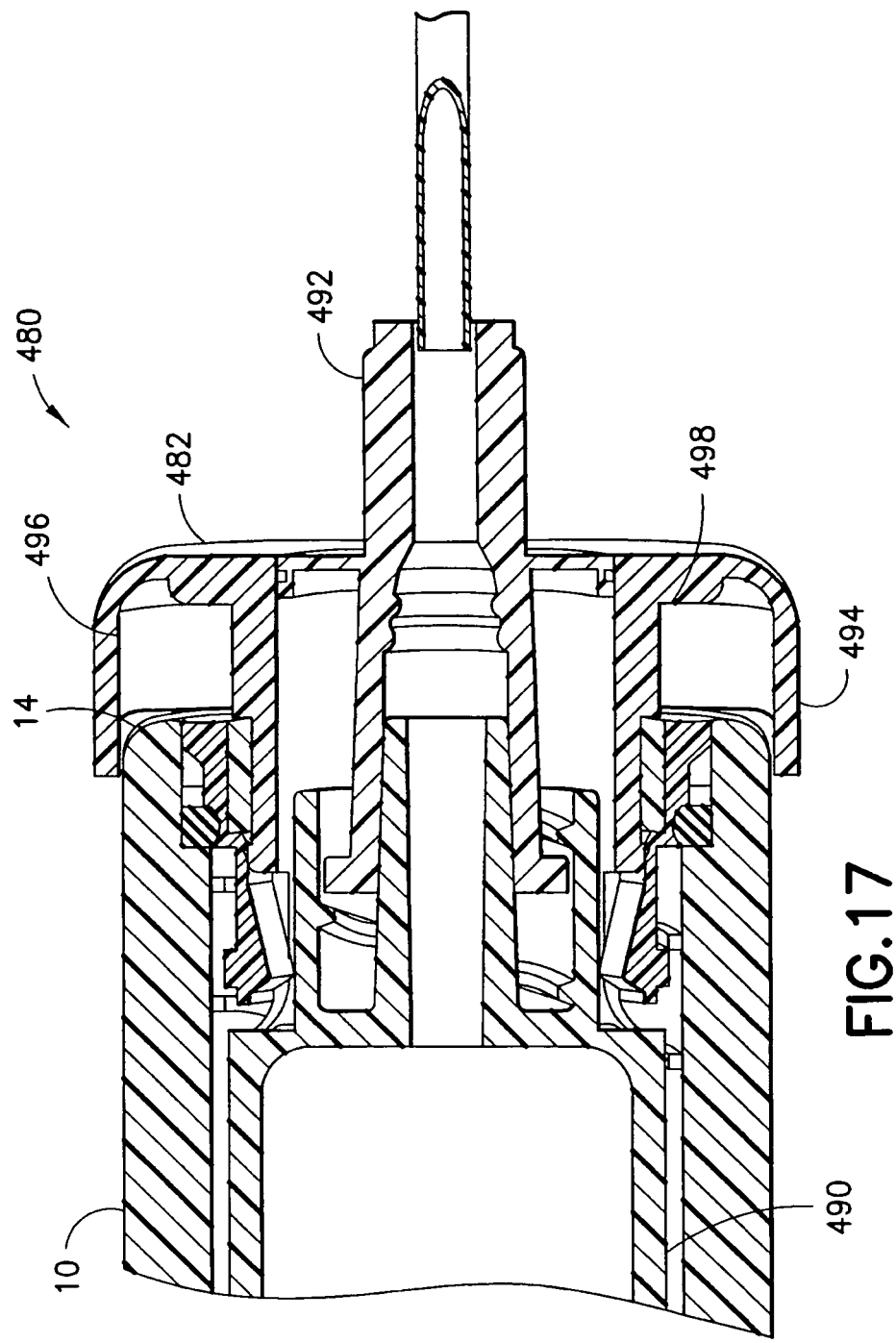
FIG. 17 is an enlarged sectional view of the fourth embodiment of an alignment guide, reservoir, and straight-line, push-on connector assembly inserted into the infusion pump of FIG. 1 in accordance with an embodiment of the present invention.
Figure 18:
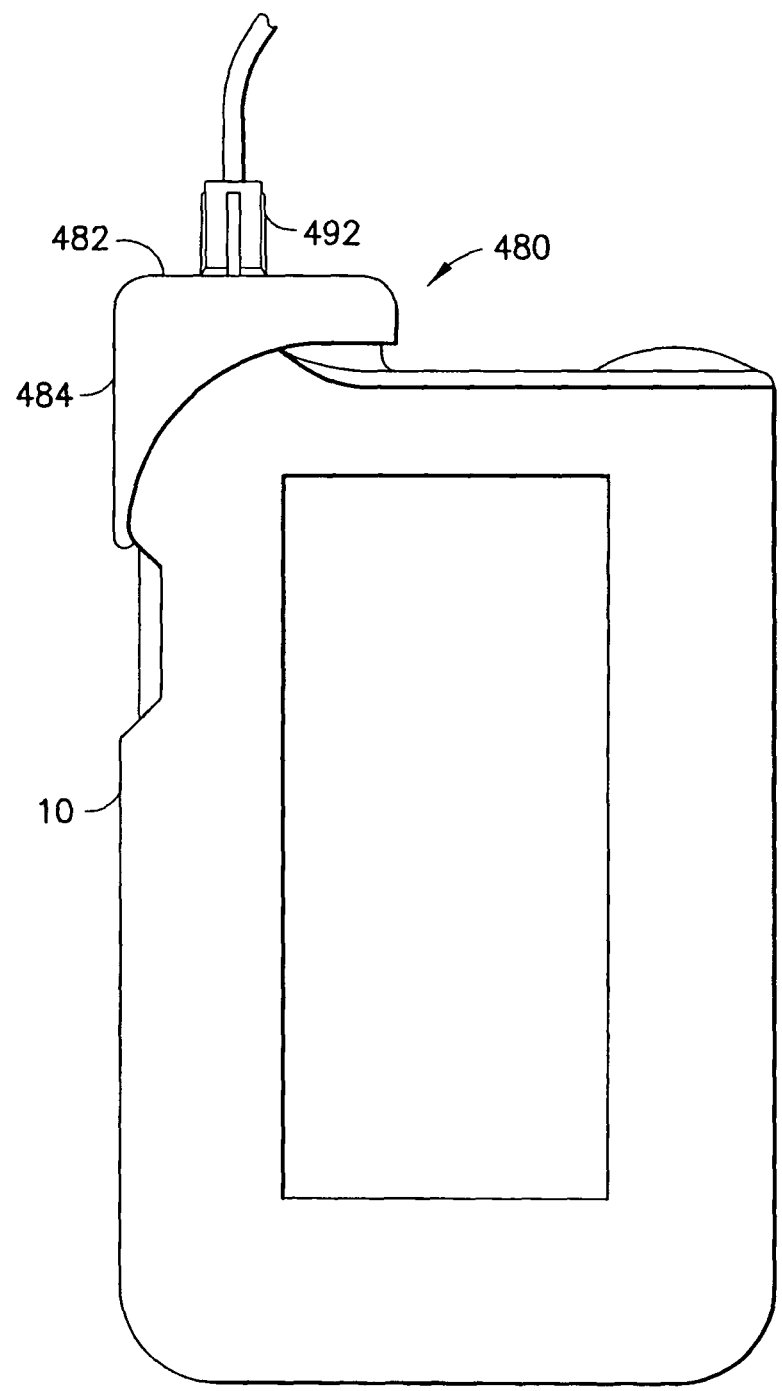
FIG. 18 is a perspective view of the fourth embodiment of an alignment guide, reservoir, and straight-line, push-on connector assembly inserted into the infusion pump of FIG. 1 in accordance with an embodiment of the present invention.

In this or other exemplary embodiments of the present invention, an integrated guide can be designed and provided to target a desired alignment of the assembly as the reservoir and straight-line, push-on connector assembly are engaged into the pump reservoir cavity. FIG. 16 is an exploded view of a fourth exemplary embodiment of such an alignment guide, reservoir, and straight-line, push-on connector assembly for interfacing a line set with the infusion pump of FIG. 1 in accordance with an embodiment of the present invention, and FIGS. 17 and 18 are views of the fourth embodiment inserted with the infusion pump of FIG. 1.

In the exemplary embodiment, an expander sleeve 480 is further configured to provide an integrated guide for insertion of the reservoir. Since the expander sleeve is preferably retained by the reservoir, the integrated guide 480 of the fourth embodiment is configured to orient the reservoir relative to the top and side surfaces of the infusion pump 10 during insertion. To do so, the integrated guide 480 has a flat top surface 482 and a side-wall member 484 to slide along a side surface of the infusion pump 10. A tab 486 is provided with the integrated guide 480 to releasably capture a detent opening 488 in the side of the infusion pump 10 and thereby serve to secure the integrated guide 480 with the infusion pump 10. Further, as shown in greater detail in FIG. 17, the guide 480 can comprise a second side-wall member 494 to slide along an opposite side surface of the infusion pump 10, and can comprise reliefs 496 and 498 to engage the opening 14 and provide a lower profile when the guide 480 is fully seated. The remaining expander sleeve elements and functions are substantially provided as described above.

Figure 19:
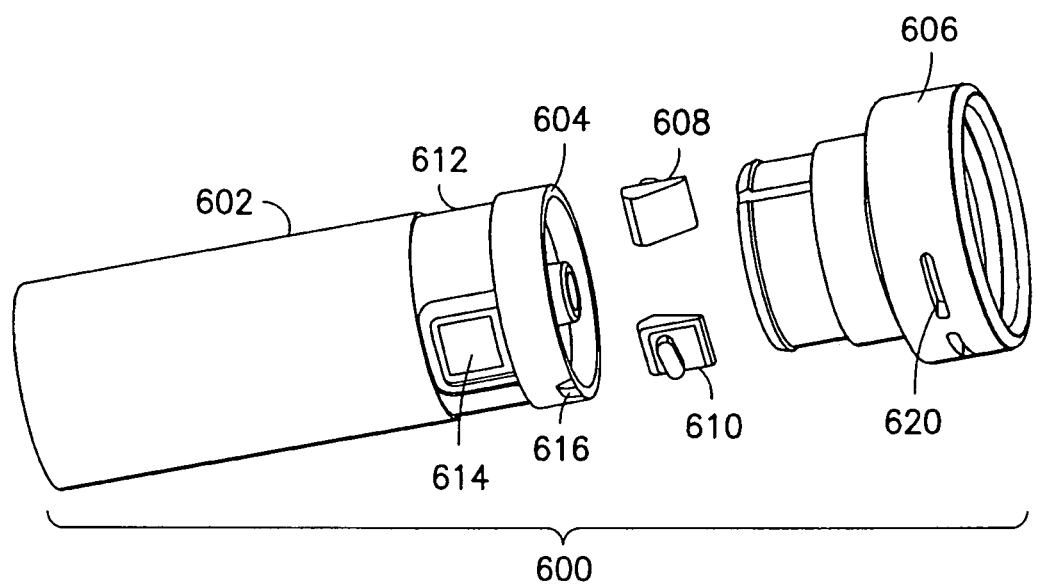
FIG. 19 is an enlarged exploded view of a fifth exemplary embodiment of an "armless" reservoir and straight-line, push-on connector assembly for interfacing a line set with the infusion pump of FIG. 1 in accordance with an embodiment of the present invention.
Figure 20:
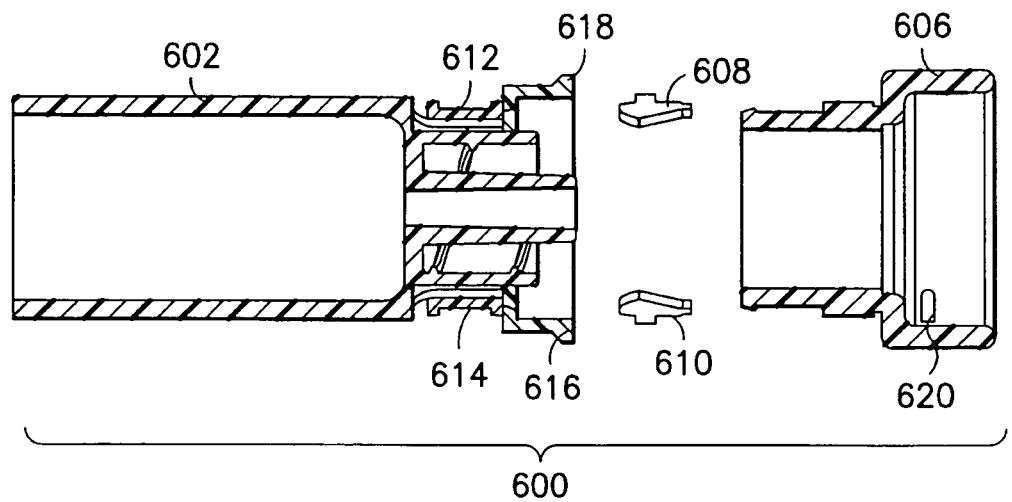
FIG. 20 is an enlarged exploded sectional view of the fifth embodiment of an "armless" reservoir and straight-line, push-on connector assembly for interfacing a line set with the infusion pump of FIG. 1.

FIGS. 19 and 20 are exploded views of a fifth exemplary embodiment of an "armless" reservoir and straight-line, push-on connector assembly 600 for interfacing a line set with the infusion pump of FIG. 1 in accordance with an embodiment of the present invention. In the exemplary embodiment shown, the reservoir 602 is provided with an open end 604 with detents 616 and 618 and an expander sleeve 606 in a manner similar to the exemplary embodiments described above.

However, in this case, the features for engaging the inner surfaces of the reservoir opening 14 are not disposed upon flexible arms of the reservoir, but are simply provided as pieces 608 and 610 that can be captured between the reservoir 602 and the expander sleeve 606. The pieces 608 and 610 are configured to be captured between "tracks" that are disposed on a surface of the expander sleeve 606 that advances the pieces, and "tracks" on the reservoir 602 that retract the pieces. Once captured in such a position, the seating of the expander sleeve 606 displaces the pieces 608 and 610 outward via openings 612 and 614 in the reservoir to secure the pieces 608 and 610 against the inner configuration of the reservoir openings and thereby secure the reservoir 602 with the infusion pump cavity.

Figure 21:
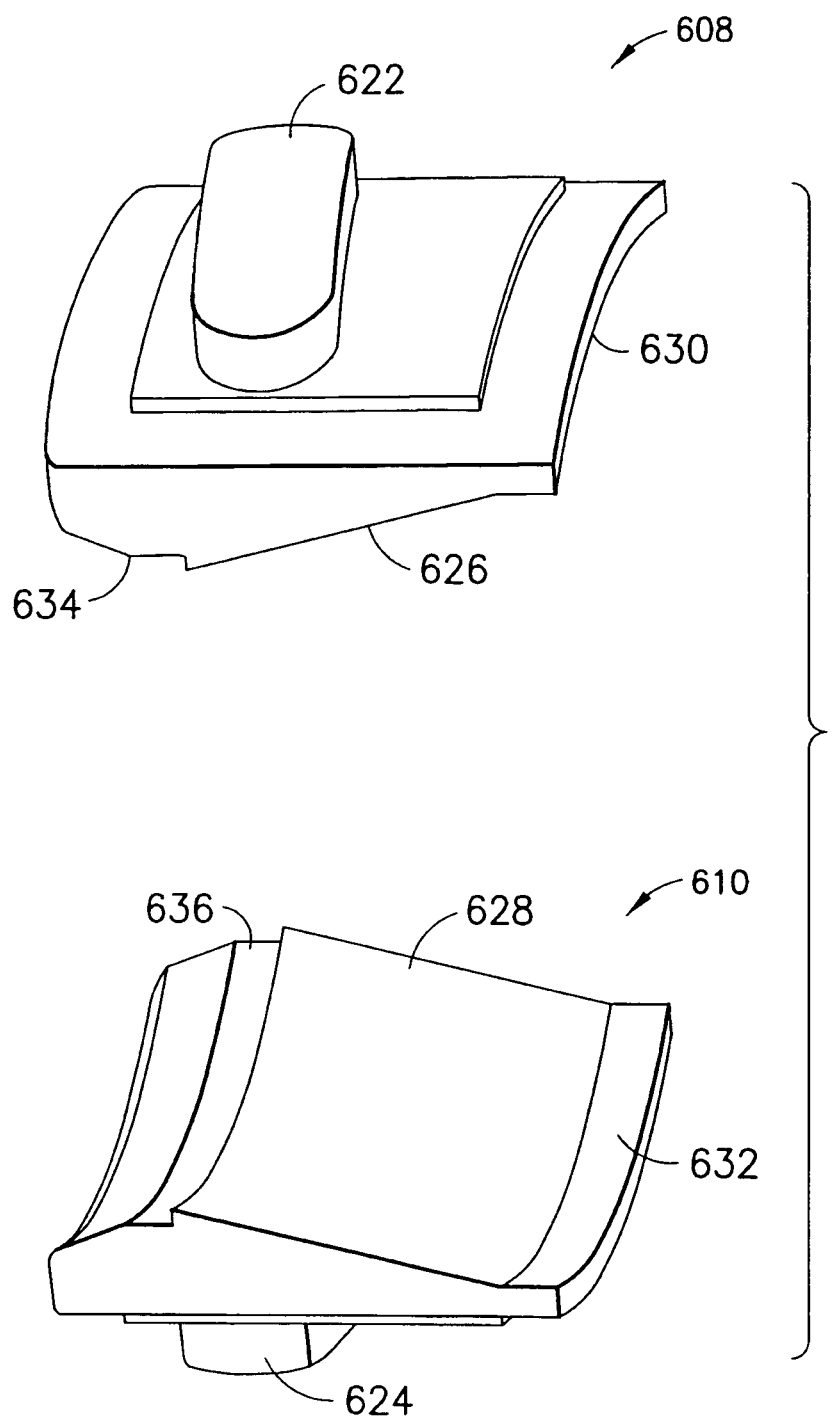
FIG. 21 are enlarged views of the floating tabs of FIG. 20 shown in greater detail in accordance with an embodiment of the present invention.

As shown in greater detail in FIG. 21, the pieces 608 and 610 each comprise an outer surface having members 622 and 624, respectively, and on opposite surfaces, an incline 626 and 628. A lower portion of the incline has a flat surface 630 and 632, and an upper portion of the incline has a shoulder and opposite incline 634 and 636.

Figure 22:
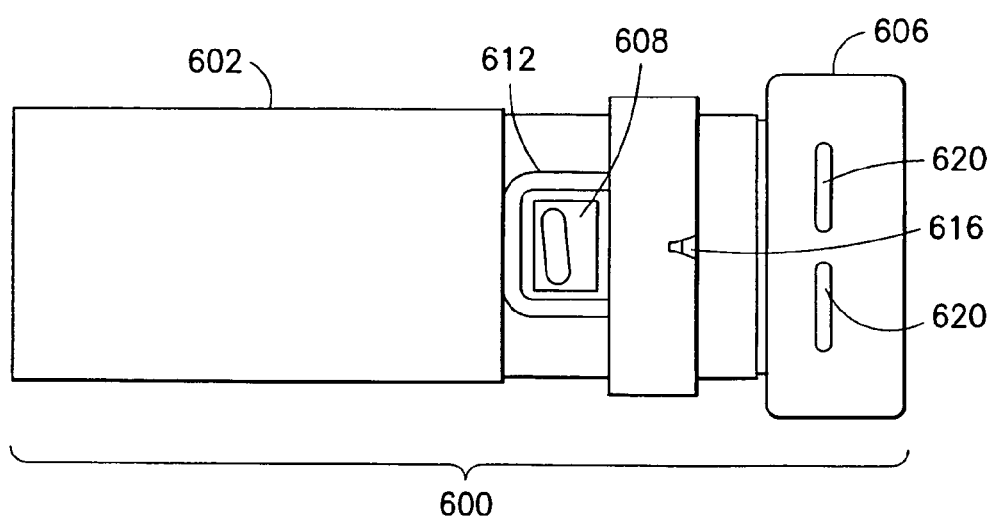
FIG. 22 is an enlarged perspective view of the fifth embodiment of an assembled "armless" reservoir and straight-line, push-on connector assembly for interfacing a line set with the infusion pump of FIG. 1 in accordance with an embodiment of the present invention.
Figure 23:
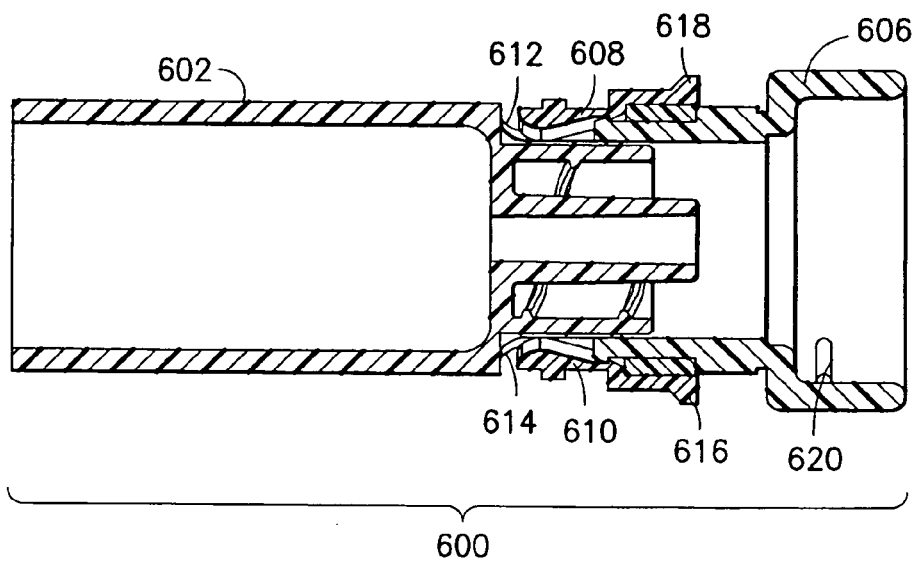
FIG. 23 is an enlarged sectional view of the fifth embodiment of an assembled "armless" reservoir and straight-line, push-on connector assembly for interfacing a line set with the infusion pump of FIG. 1 in accordance with an embodiment of the present invention.

FIGS. 22 and 23 are views of the fifth embodiment of an assembled "armless" reservoir and straight-line, push-on connector assembly. The pieces 608 and 610 are positioned within openings 612 and 614 in the reservoir 602, and are urged outward from the openings 612 and 614 by the insertion of the expander sleeve 606 into the reservoir 602. Once urged outward in such a manner, the pieces 608 and 610 perform substantially as described above in regard to embodiments one to five.

The exemplary embodiment shown in FIGS. 19-23 illustrates another example of the positioning of a hydrophobic membrane on the grasping diameter of the expander sleeve 606. In this case, the hydrophobic membrane covered openings 620 provide a pathway for air ingress and egress, and a flat surface is provided on an inner surface of the expander sleeve 606 on which to attach the hydrophobic membrane. As noted above, such exemplary features are easily moldable, and the hydrophobic membrane can be heat staked or bonded with UV cured adhesive/epoxy for attachment. An exemplary hydrophobic membrane is comprised of a PTFE or ePTFE material, but is not limited thereto.

In yet another exemplary embodiment of the present invention, one or more of the materials can be selected for desired properties, and combination of materials can be used to achieve desired results. For example, in an exemplary embodiment of the present invention, a two-piece reservoir can be used wherein the reservoir can comprise a cyclic olefin polymer (COP), cyclic olefin copolymer (COC) material, or CCP (Crystal Clear Polymer), which is a material registered by Becton and Dickinson Co. and listed by the U.S. Food and Drug Administration as DMF No. 16368, and further comprise an integral CCP, COP or COC Luer connector, combined with an upper sleeve manufactured from flexible polypropylene to allow, for example, the moveable latches or arms on the upper sleeve to flex without fracturing. To achieve such results, an exemplary embodiment can comprise a combination reservoir design with the upper sleeve made from polypropylene (PP) and the cartridge or remaining portions made from CCP, COP or COC.

Figure 24:
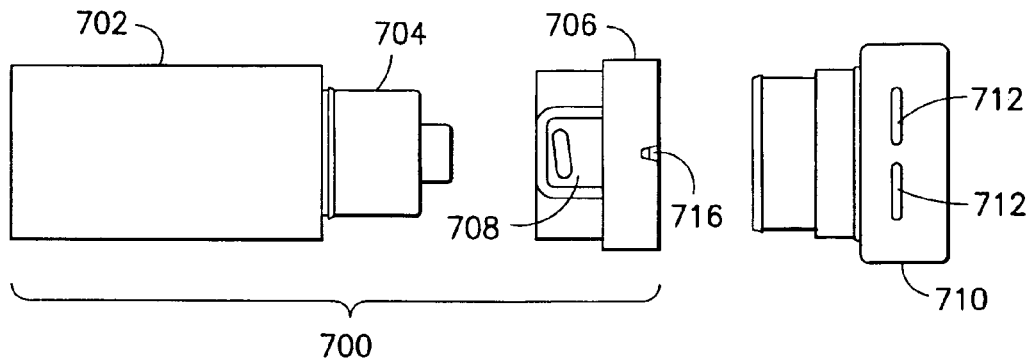
FIG. 24 is an exploded view of a sixth exemplary embodiment of a reservoir and straight-line, push-on connector assembly for interfacing a line set with the infusion pump of FIG. 1, wherein the top or push-on portion is made of a first material, and the remaining or cartridge portion is made from a second material, in accordance with an embodiment of the present invention.
Figure 25:
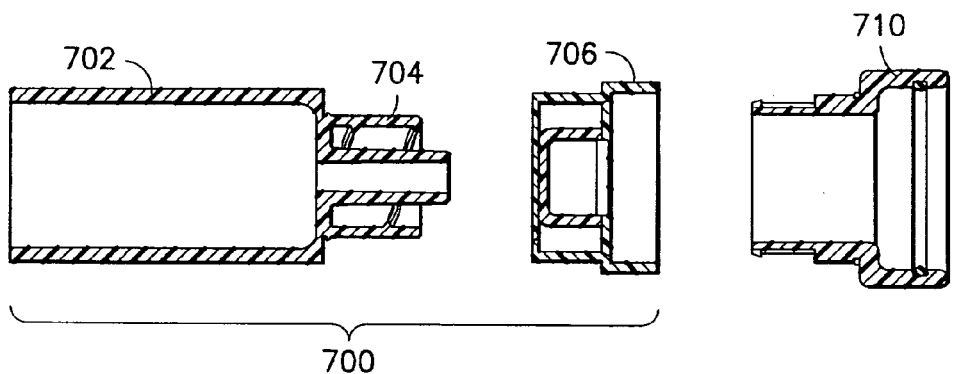
FIG. 25 is an exploded sectional view of the sixth embodiment of a reservoir and straight-line, push-on connector assembly for interfacing a line set with the infusion pump of FIG. 1 in accordance with an embodiment of the present invention.

FIGS. 24 and 25 are exploded views of a sixth exemplary embodiment of a reservoir and straight-line, push-on connector assembly for interfacing a line set with the infusion pump of FIG. 1, wherein the top portion is made of a first material, and the remaining or cartridge portion is made from a second material, in accordance with an embodiment of the present invention. Specifically, a two-piece reservoir 700 can be used wherein the reservoir 702 can comprise a CCP, COP or COC material, and further comprise an integral CCP, COP or COC Luer connector 704, combined with an upper sleeve 706 that can be snapped onto the top of the reservoir or otherwise provided, and manufactured from flexible polypropylene or other flexible polymer to allow, for example, the moveable latches or arms 708 on the upper sleeve 706 to flex without fracturing. To achieve such results, an exemplary embodiment can comprise a combination reservoir design with the upper sleeve 706 made from PP and the cartridge 702, 704 and/or expander sleeve 710 made from CCP, COP or COC. Such elements can be assembled into a complete reservoir and straight-line, push-on type connector assembly to function substantially as described above. For example, FIG. 26 is a view of the sixth embodiment of the assembled reservoir and straight-line, push-on connector assembly.

Figure 26:
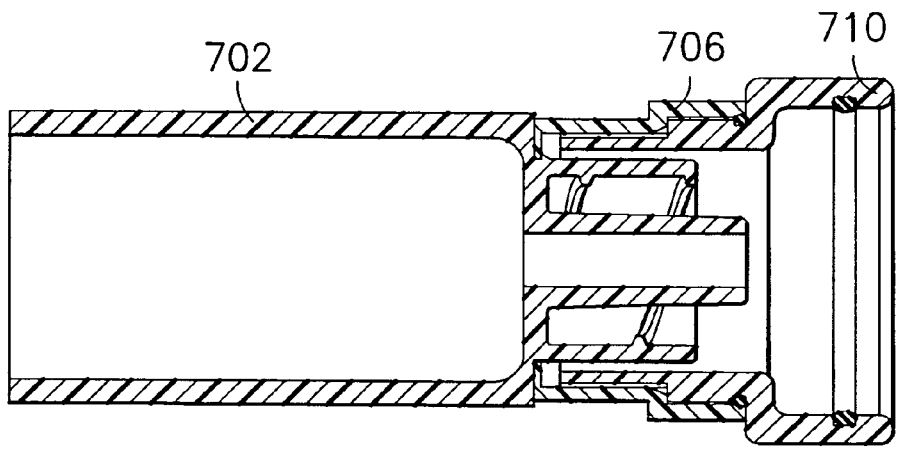
FIG. 26 is a perspective view of the sixth embodiment of an assembled reservoir and straight-line, push-on connector assembly for interfacing a line set with the infusion pump of FIG. 1 in accordance with an embodiment of the present invention.

The exemplary embodiment shown in FIGS. 24-26 illustrates another example of the positioning of a hydrophobic membrane on the grasping diameter of the expander sleeve 710. In this case, the hydrophobic membrane covered openings 712 provide a pathway for air ingress and egress, and a flat surface is provided on an inner surface of the expander sleeve 710 on which to attach the hydrophobic membrane. As noted above, such exemplary features are easily moldable, and the hydrophobic membrane can be heat staked or bonded with UV cured adhesive/epoxy for attachment. An exemplary hydrophobic membrane is comprised of a PTFE or ePTFE material, but is not limited thereto.

In yet other exemplary embodiments of the present invention a septum adapter can be incorporated into the reservoir and connector assembly to aid in preventing leakage from the reservoir during user setup procedures. In such exemplary embodiments, a septum, such as a standard septum or split, stretchable or otherwise pre-pierced septum, can be used. A split, stretchable or otherwise pre-pierced septum can eliminate the need for a cannula in the mating components to pierce the septum. Such a septum can be stretched open when the connector assembly is attached to the reservoir. However, where desirable to do so, the septum could be pierced or opened by a male Luer or blunt cannula that is connected to the Luer connector of the line set or other line set component.

Figure 27:
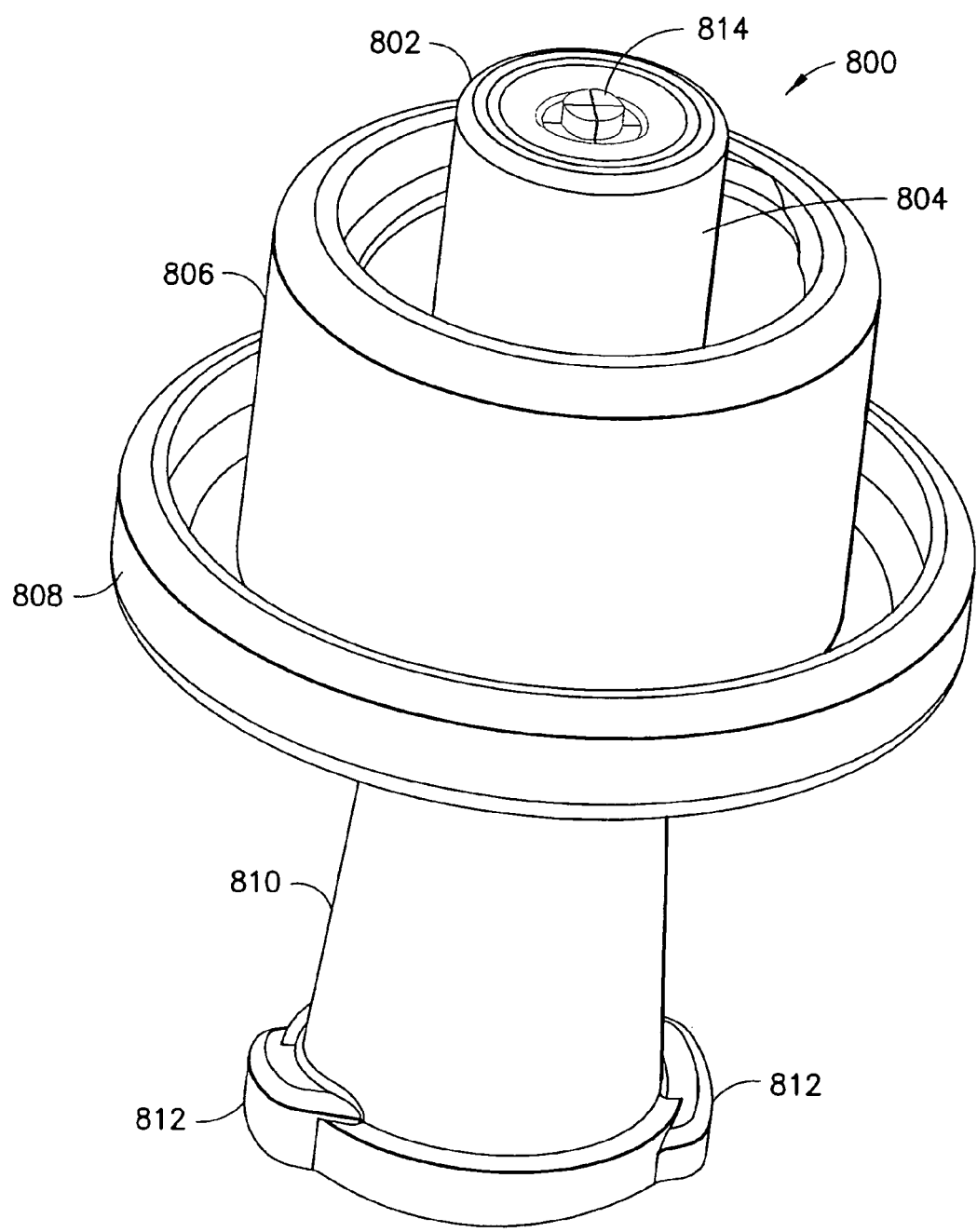
FIG. 27 is an enlarged perspective view of a luer adapter with integral split septum of a seventh exemplary embodiment of a straight-line, push-on connector assembly for interfacing a line set with the infusion pump of FIG. 1 in accordance with an embodiment of the present invention.
Figure 28:
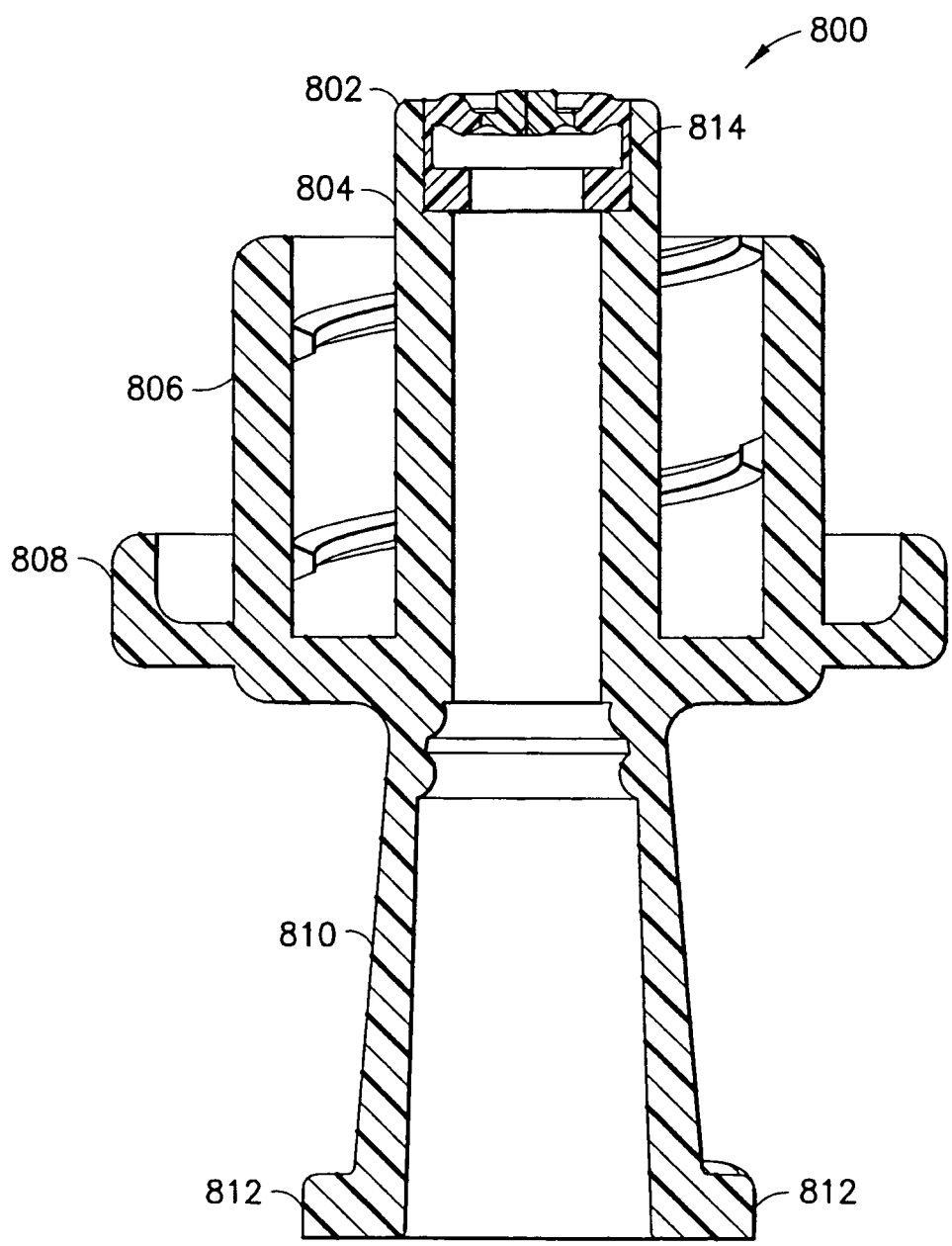
FIG. 28 is an enlarged sectional view of the luer adapter with integral split septum of the seventh embodiment of a push-on connector assembly for interfacing a line set with the infusion pump of FIG. 1 in accordance with an embodiment of the present invention.

For example, FIGS. 27 and 28 are views of a split septum of a seventh exemplary embodiment of a straight-line, push-on connector assembly for interfacing a line set with the infusion pump of FIG. 1 in accordance with an embodiment of the present invention. In the seventh exemplary embodiment, a septum can be incorporated into the adapter wherein an opening in the septum for subsequent use can be pre-made, made during earlier operations such as filling the reservoir, or by providing some sharp to pierce and provide a fluid path to the line set.

Figure 29:
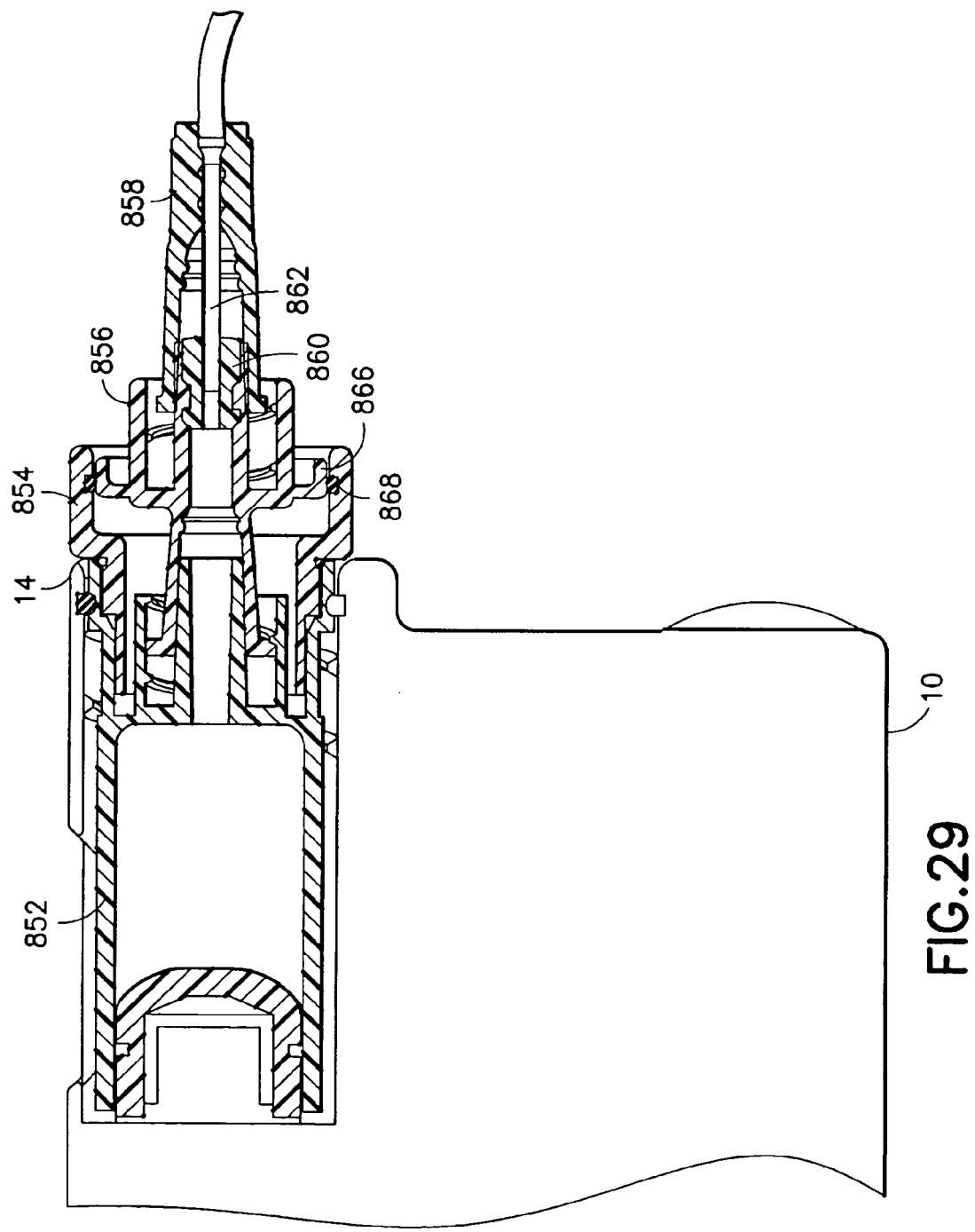
FIG. 29 is an enlarged sectional view of an eighth embodiment of a reservoir and straight-line, push-on connector assembly with a standard septum within the infusion pump of FIG. 1 in accordance with an embodiment of the present invention.
Figure 30:
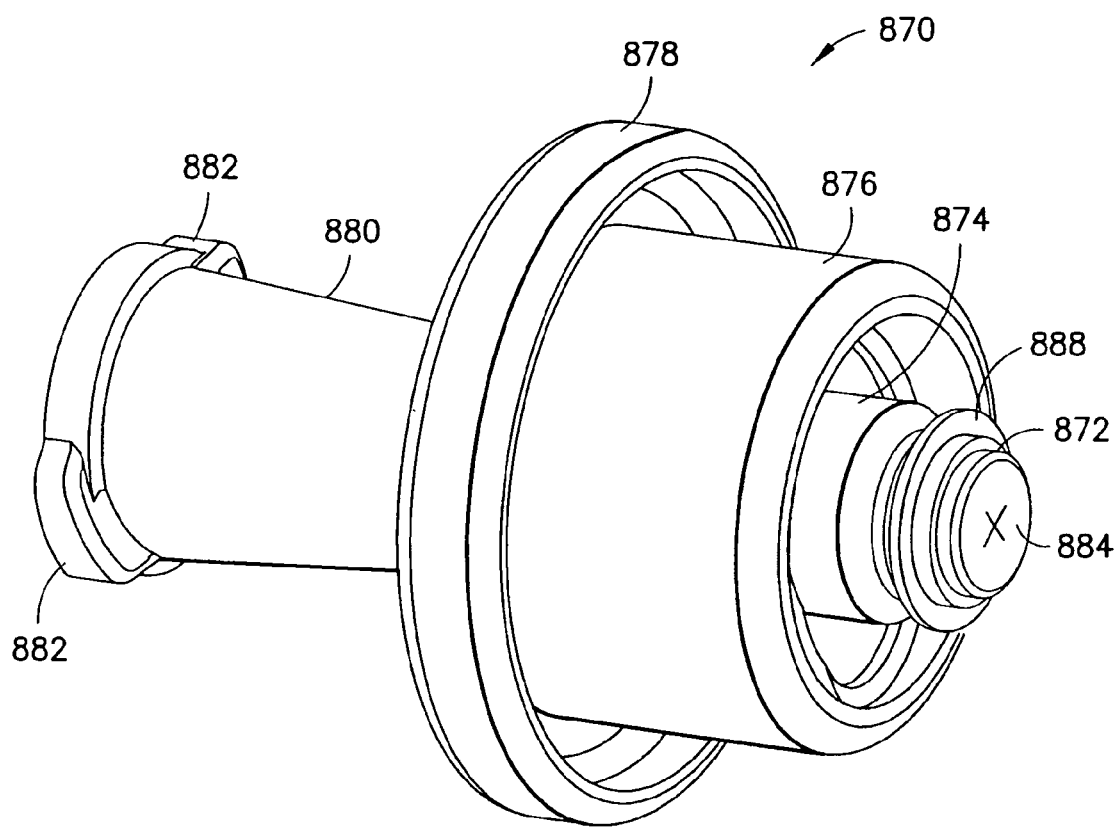
FIG. 30 is a perspective view of a ninth exemplary embodiment of a straight-line, push-on connector assembly with a stretch-open type septum for interfacing a line set with the infusion pump of FIG. 1 in accordance with an embodiment of the present invention.

The split septum connector adapter 800 of FIGS. 27 and 28 comprises a first end 802 for receiving a custom Luer connector in which a hydrophobic membrane is provided, and a split, opened, or otherwise pre-pierced septum 814 is secured or molded at the first end 802 to receive the custom Luer connector. For example, as shown in FIG. 28 the septum 814 can comprise a cylindrical plug wherein retention is provided by an interference engagement between the septum 814 and a mating cavity in the connector adapter 800. The remaining elements of the connector assembly 800 include the inner barrel 804 and outer threaded barrel 806, and the flange 808 extending therefrom to seal the opening of the expander sleeve. For the exemplary embodiment shown in FIGS. 27 and 28, a hydrophobic membrane can located in the side wall of an expander sleeve used with the embodiment, a flange of the expander sleeve, or the flange 808 of the adapter 800. The second end of the split septum connector adapter 800 includes the barrel 810 and engagement tabs 812 to engage the Luer connection of the reservoir.

Where a standard septum is used and piercing is required, a custom Luer fitting can be used to pierce the septum. FIGS. 29 and 30 are views of an eighth exemplary embodiment of a reservoir and straight-line, push-on connector assembly with a standard or conventional septum for interfacing a line set with the infusion pump of FIG. 1 in accordance with an embodiment of the present invention. An infusion pump 10 is provided to receive a reservoir 852, expander sleeve 854, conventional septum connector adapter 856 and a custom Luer fitting 858. In this case, a conventional septum 860 is provided in the connector adapter 856 for receiving the custom Luer fitting 858 during assembly.

As shown in FIG. 29, the septum 860 could be opened by a male Luer fitting or blunt cannula 862 that is connected either to the Luer connector of the line set or other line set component. For the exemplary embodiment shown in FIG. 29, a hydrophobic membrane can located in the side wall of the expander sleeve 854 used with the embodiment, a flange of the expander sleeve 854, or the flange of the adapter 856. The adapter 856 has a flange 866 having a sufficient diameter to close the opening of the expander sleeve 854 when contacting the seal 868 on the inner diameter of the expander sleeve 854. The second end of the split connector adapter 856 includes the barrel and engagement tabs to engage the Luer connection of the reservoir as described above.

In this case, the hydrophobic membrane can be provided on the grasping diameter of the expander sleeve 854. Hydrophobic membrane covered openings can be provided extending from the outer diameter to a circumferential groove (not shown) which would provide a pathway for air ingress and egress, and a flat surface can be provided on an inner surface of the expander sleeve 854 on which to attach the hydrophobic membrane. Such exemplary features are easily moldable, and the hydrophobic membrane can be heat staked or bonded with UV cured adhesive/epoxy for attachment. An exemplary hydrophobic membrane is comprised of a PTFE or ePTFE material, but is not limited thereto.

Figure 31:
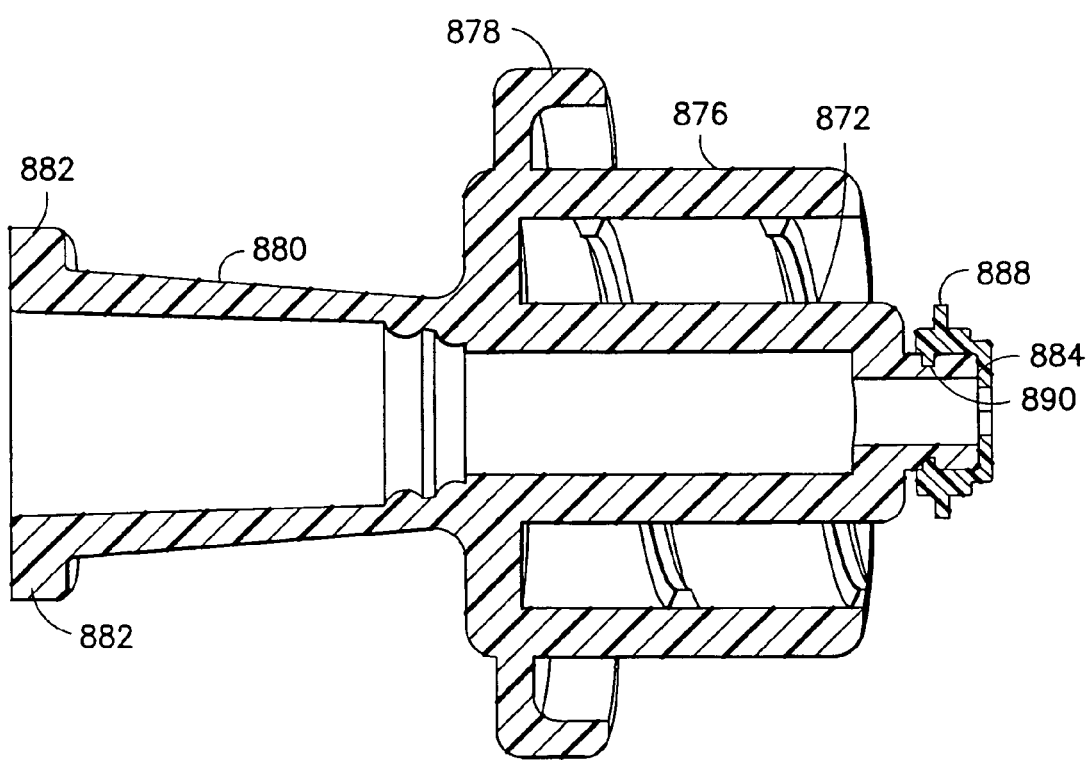
FIG. 31 is a sectional view of the ninth embodiment of the push-on connector assembly with a stretch-open type septum for interfacing a line set with the infusion pump of FIG. 1 in accordance with an embodiment of the present invention.
Figure 32:
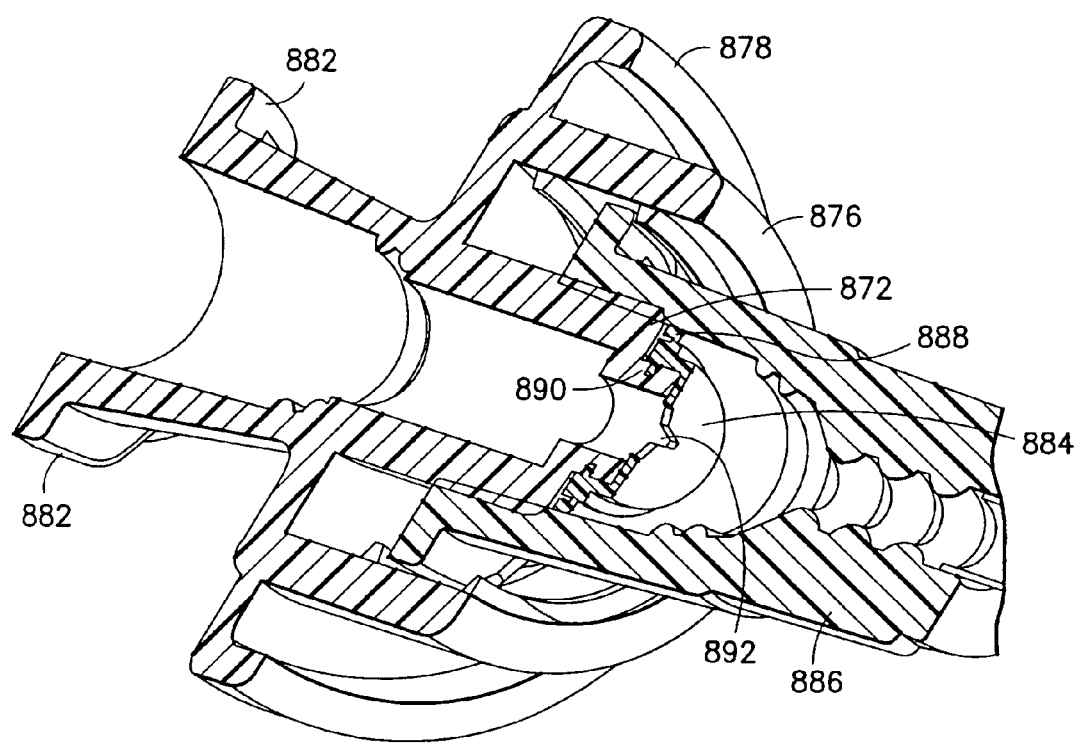
FIG. 32 is a sectional oblique view of the ninth embodiment of the push-on connector assembly with a stretch-open type septum shown in the open state after being assembled with a Luer fitting for interfacing a line set with the infusion pump of FIG. 1 in accordance with an embodiment of the present invention.

FIGS. 30-32 are views of a ninth exemplary embodiment of a straight-line, push-on connector adapter 870 with a stretch-open type septum for interfacing a line set with the infusion pump of FIG. 1 in accordance with an embodiment of the present invention. The stretch-open type septum connector adapter 870 comprises a first end 872 for receiving a Luer connector. Specifically, a pre-pierced stretchable septum 884 is secured or molded over the first end 872 to receive a Luer connector. The septum 884 further comprises at least a pliable detent 888 and a securing detent 890. As described in greater detail below, the securing detent 890 can be used to secure the septum 884 to the end of the adapter 870, and the pliable detent 888 can be used to contact the Luer connector, sealing any opening, and though such contact, stretching open an opening in the septum 884. The remaining elements of the connector adapter 870 include the inner barrel 874 and outer threaded barrel 876, and the flange 878 extending therefrom to seal the opening of the connector assembly. For the exemplary embodiment shown in FIGS. 30-32, a hydrophobic membrane can located in the side wall of an expander sleeve used with the embodiment, a flange of the expander sleeve, or the flange 878 of the adapter 870. The second end of the adapter 870 includes the barrel 880 and engagement tabs 882 to engage the Luer connection of the reservoir.

FIG. 32 is a sectional view of the ninth embodiment of the straight-line push connector assembly with a stretch-open type septum assembled with a Luer fitting. As shown in FIG. 32, the engagement with the Luer fitting 886 serves to stretch the septum 884 thereby creating an opening 892 in the center of the septum 884 which remains closed at other times. The pliable detent 888 of the septum 884 contacts the Luer connector 886 during use, sealing any opening between the adapter 870 and the Luer connector and though such contact, stretching open the opening 892 in the septum 884 such that no cannula is needed in the Luer connecter.

Figure 33:
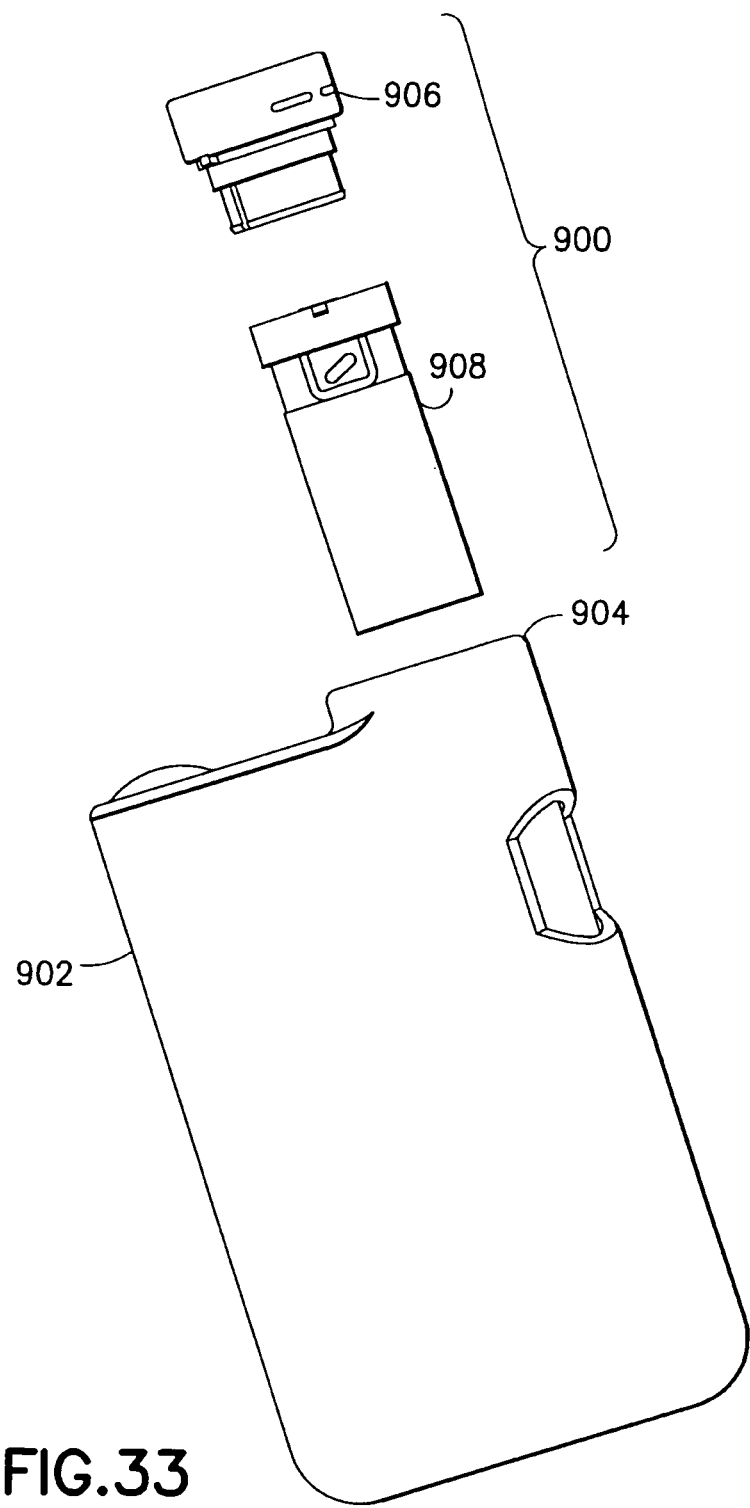
FIG. 33 is an exploded view of a tenth exemplary embodiment of a reservoir and straight-line, push-on connector assembly for interfacing a line set with another infusion pump in accordance with an embodiment of the present invention.
Figure 34:
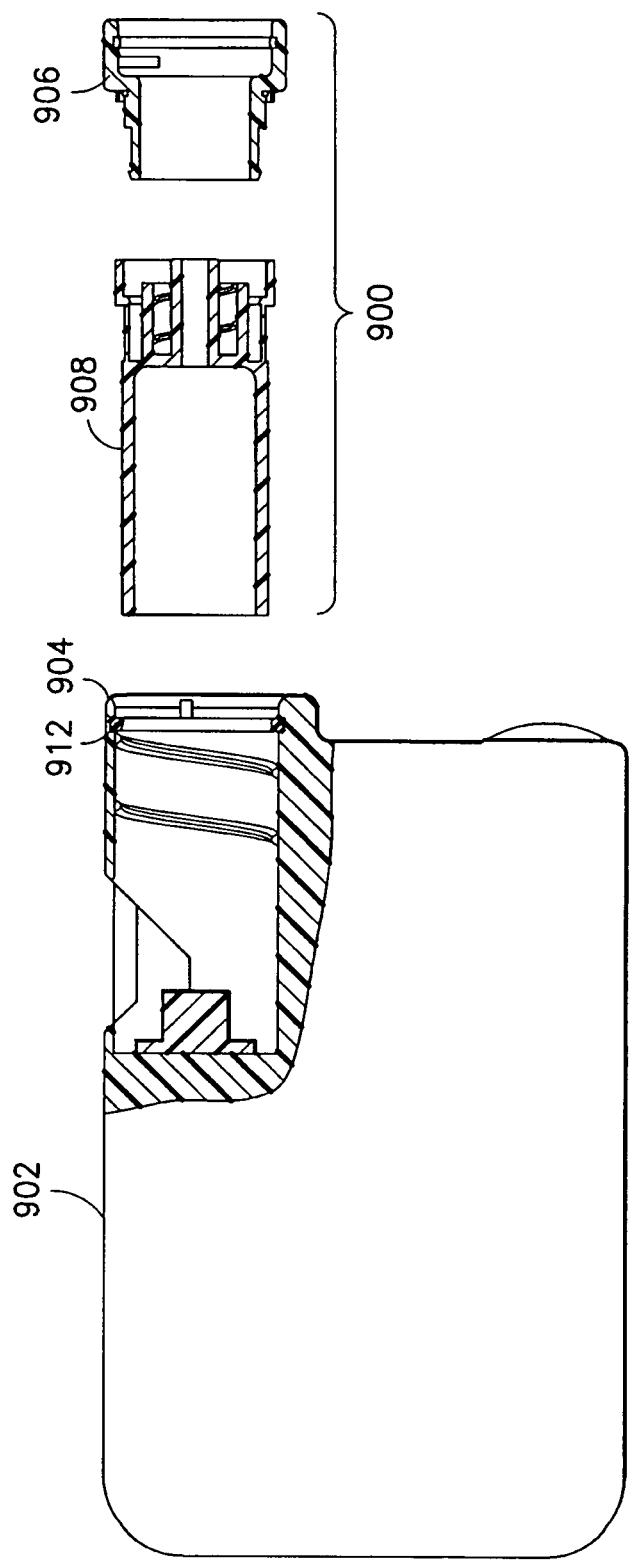
FIG. 34 is an exploded sectional view of the tenth embodiment of a reservoir and straight-line, push-on connector assembly for interfacing a line set with another infusion pump in accordance with an embodiment of the present invention.
Figure 35:
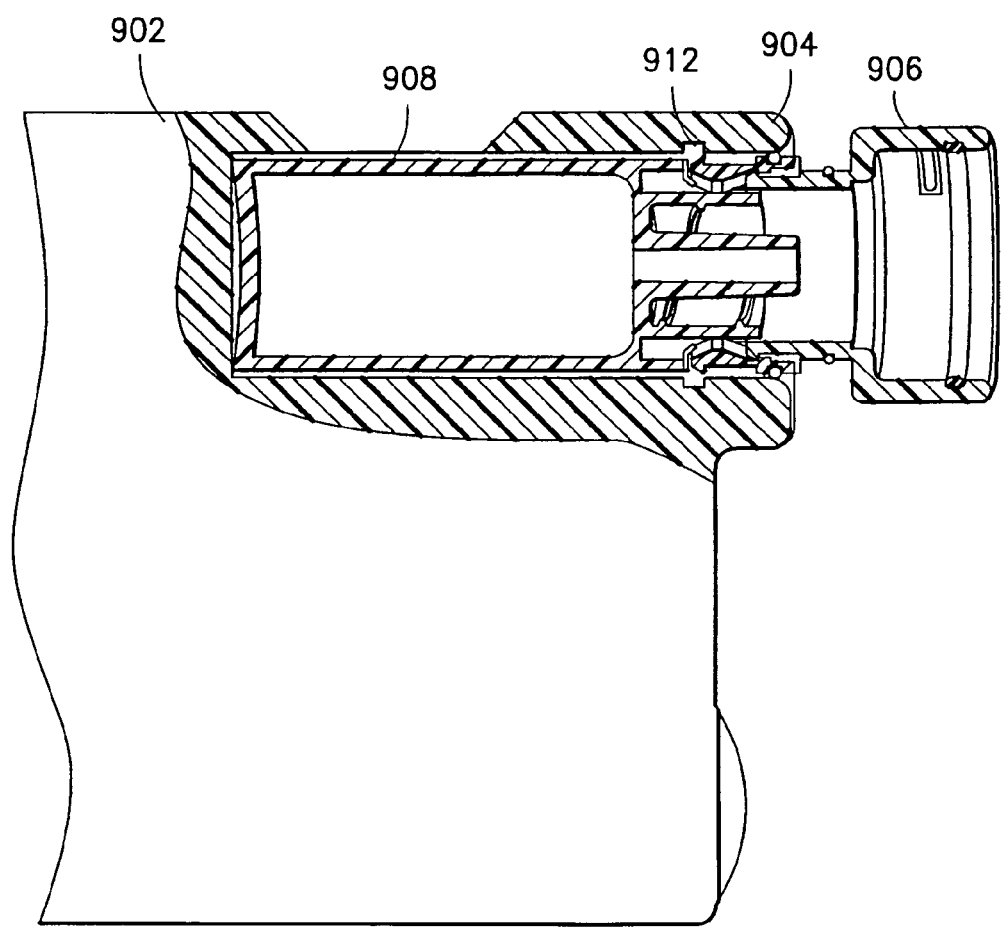
FIG. 35 is a sectional view of the tenth embodiment of an assembled reservoir and an unseated straight-line, push-on connector assembly within the other infusion pump in accordance with an embodiment of the present invention.
Figure 36:
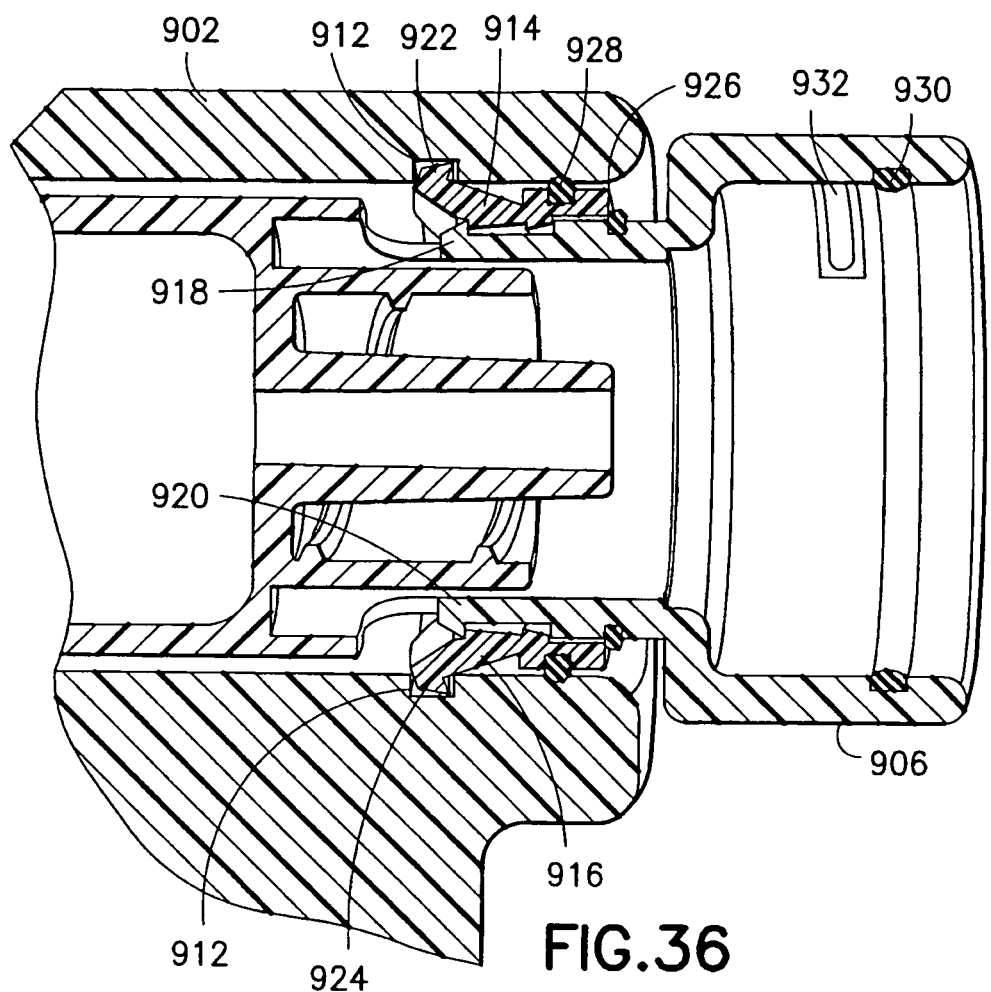
FIG. 36 is a sectional view of the tenth embodiment of an assembled reservoir and a seated straight-line, push-on connector assembly within the other infusion pump in accordance with an embodiment of the present invention.

FIG. 33 is an exploded view of a tenth exemplary embodiment of a reservoir and straight-line, push-on connector assembly for interfacing a line set with another infusion pump in accordance with an embodiment of the present invention. FIG. 34 is an exploded sectional view and FIGS. 35 and 36 are sectional views of the assembled reservoir and unseated straight-line push connector assembly within the infusion pump. The infusion pump can be provided with either an O-ring that is removed, or simply an O-ring space within the reservoir opening to which an exemplary reservoir and connector assembly can be secured. The O-ring seal or function thereof can be replaced with a seal located on the outer surface of the expander sleeve flange.

Figure 37:
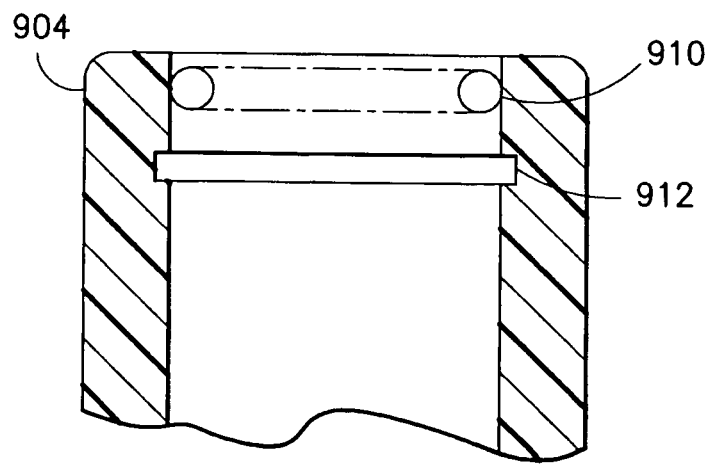
FIG. 37 is a sectional view of the connection features of the other infusion pump in accordance with an embodiment of the present invention.
Figure 38:
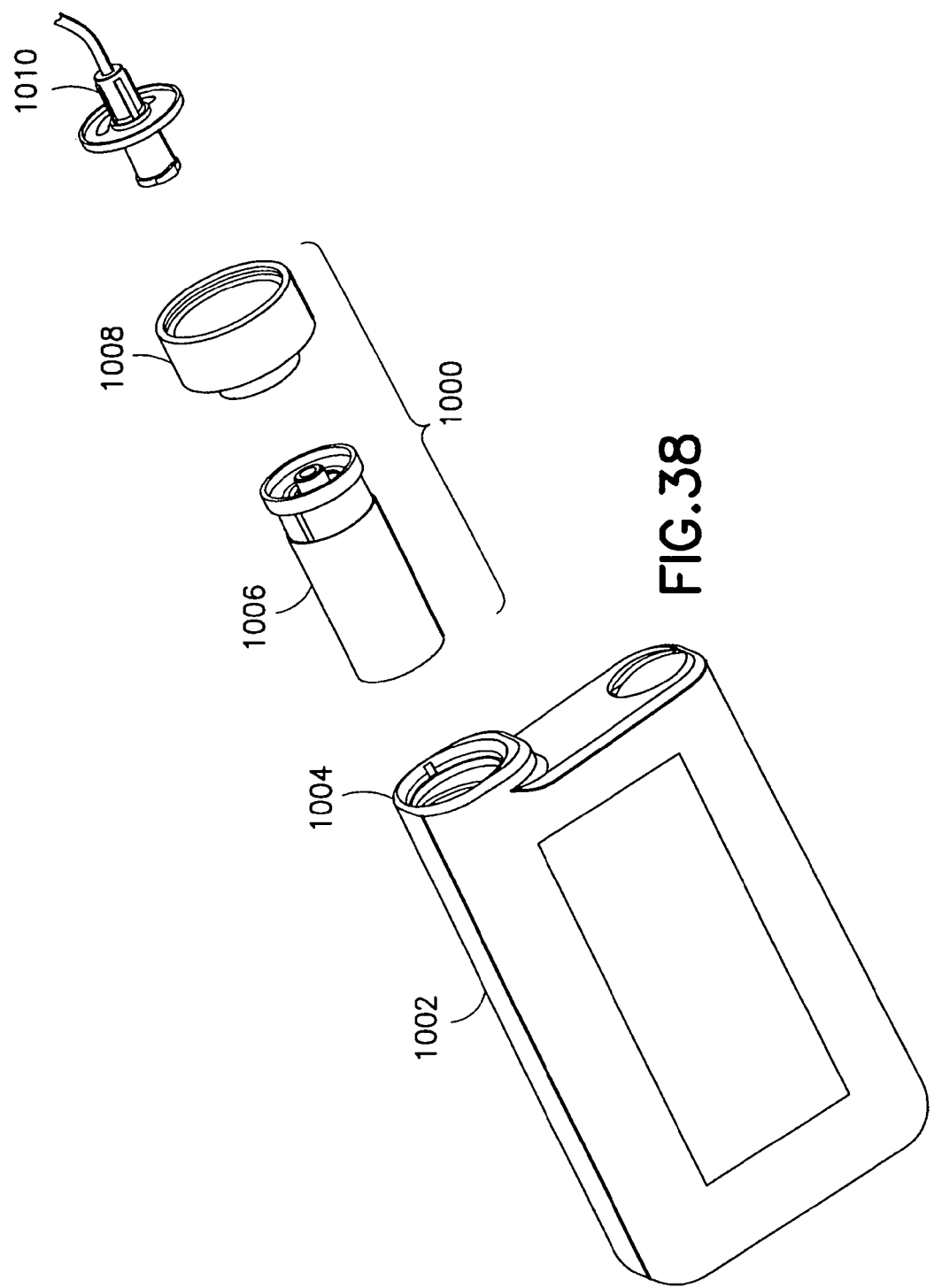
FIG. 38 is an exploded view of an eleventh exemplary embodiment of a reservoir and straight-line, push-on connector assembly for interfacing a line set with another infusion pump without O-ring in accordance with an embodiment of the present invention.
Figure 39:
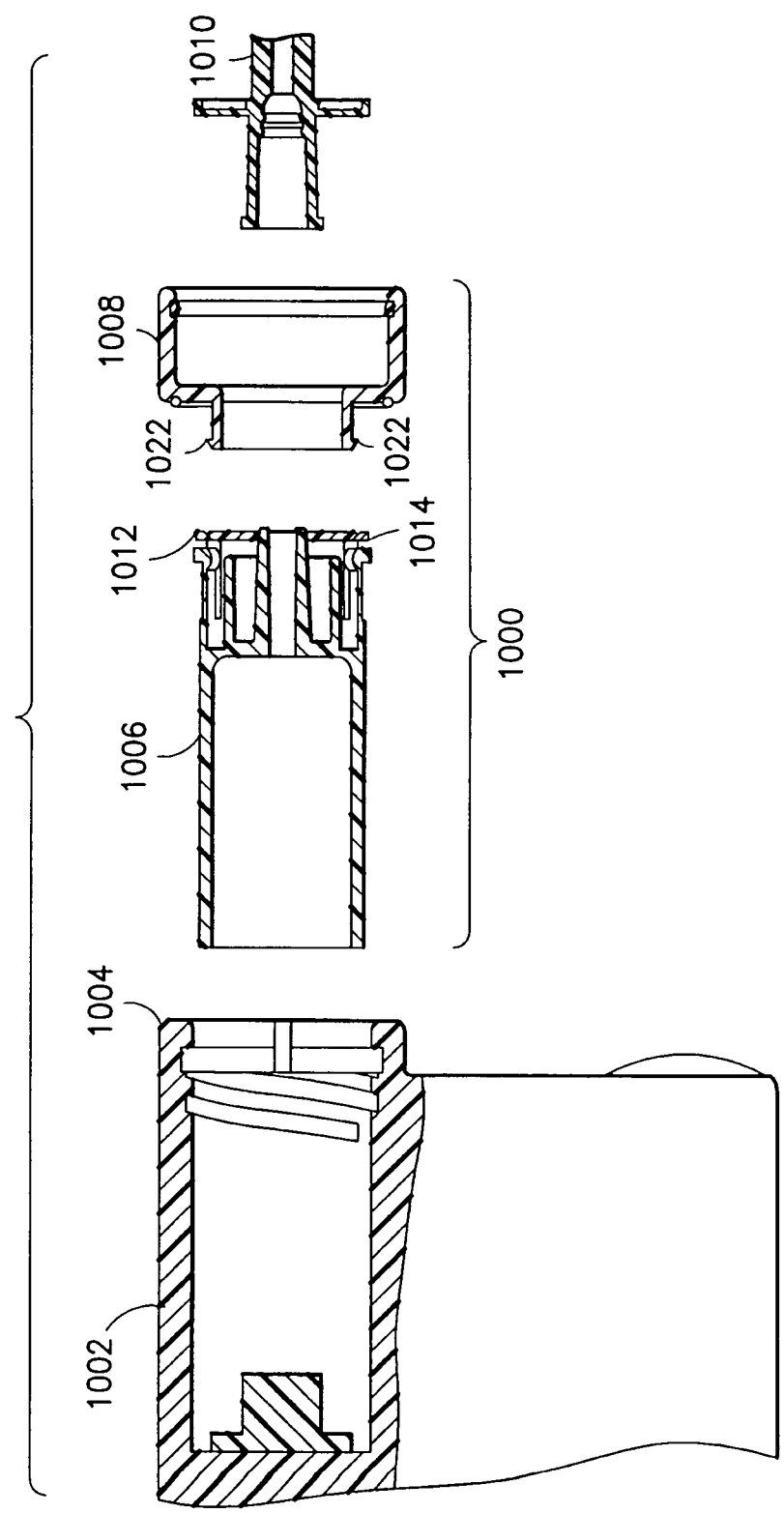
FIG. 39 is an exploded sectional view of the eleventh exemplary embodiment of a reservoir and straight-line, push-on connector assembly for interfacing a line set with another infusion pump without an O-ring in accordance with an embodiment of the present invention.

As shown in FIG. 33, the reservoir and straight-line, push-on connector assembly 900 comprises an expander sleeve 906 and reservoir 908 for use with the infusion pump 902 and at least one reservoir opening 904 therein. As shown in greater detail in FIG. 37, the reservoir opening 904 of the infusion pump 902 comprises an O-ring contact surface 910 and an annular groove 912. The exemplary O-ring contact surface 910 is the same diameter as the inner the area of the reservoir. However, in this exemplary embodiment, the expanding latches or locking features 922 and 924 of the reservoir are forced by the expander sleeve 906 into the annular groove 912 of the opening 904 of the infusion pump 902, and not simply against a side wall, or threads, of the opening 904 of the infusion pump 902 as described above. In regard to the remaining aspects, the reservoir 908 can be inserted into the opening 904 followed by the expander sleeve 906 in a manner similar to that described above, wherein the seating of the expander sleeve 906 into the reservoir 908 deflects arms 914 and 916 outward via contact with the members 918 and 920 of the expander sleeve 906, such that the features 922 and 924 are forced into the annular groove 912 of the opening 904 of the infusion pump 902.

A fault indicator 926 can be provided on the expander sleeve 906 and functions substantially as described above, and seals 928 and 930 can be provided on the OD of the reservoir, and the ID of the expander sleeve, respectively. In yet other exemplary embodiments of the present invention, an additional seal (not shown) can be provided between the expander sleeve and the reservoir (see, for example, the seal 1042 of the embodiment of FIG. 41). Such an additional seal can be overmolded as with seal 928.

FIG. 36 is a sectional view of the tenth embodiment of the assembled reservoir and a seated straight-line, push-on connector assembly within the infusion pump. As shown in FIG. 36, the seated expander sleeve 906 displaces the expanding latches or locking features 922 and 924 of the reservoir into the annular groove 912 of the opening 904 of the infusion pump 902 to secure there reservoir. The hydrophobic membrane 932 can be provided on the grasping diameter of the expander sleeve 906 to permit the use a standard Luer fitting. The hydrophobic membrane covered openings can be provided for air ingress and egress for pressure equalization, and the hydrophobic membrane can be heat staked or bonded with UV cured adhesive/epoxy for attachment. An exemplary hydrophobic membrane 932 is comprised of a PTFE or ePTFE material, but is not limited thereto.

In the tenth embodiment, the O-ring or seal 928 on the reservoir 908 is preferably located at the highest point in the pump reservoir cavity to minimize contamination from insulin leakage or particulate migration. Further, since the O-ring or seal 928 is located on the reservoir 908, it can be easily replaced with each use. Further, as described above, one simple straight-line, push-on motion, preferably performed by gripping the expander sleeve, places and secures the reservoir (i.e., locates the reservoir on the x, y, and z axes) in the pump reservoir cavity, and one simple straight-line, pull-off motion releases and removes the reservoir from the pump reservoir cavity. Rotational orientation is not required for proper connection, pump engagement, or pump function, and any pulling of the tube set will not release the reservoir as the expansion sleeve through which the tube set is routed is not moved from the securing position by tension on the tube set or Luer fitting.

Still further, an audible "click" and/or a tactile "snap" occurs when the assembly is connected properly to the pump, and one or more of the warning rings or features described above are visible around the base of the expander sleeve when the assembly has not been properly connected to the pump.

Still further, as noted above, in the case where an annular groove 912 is provided in the infusion pump reservoir cavity, and which wraps completely around the diameter (i.e., 360 degrees) of the pump reservoir cavity, the annular groove can provide an engagement feature for exemplary embodiments of the present invention. In doing so an integrated guide may not be needed, since the connector would be located and locked on the x, y, and z axes once the two mating expanding latches or locking features of the reservoir have been expanded into the annular groove in the pump reservoir cavity. The basic features in the connector described herein therefore can comprise the reservoir with integral upper sleeve and moveable engagement features (i.e., latches, arms, wings, elements, and so forth), the expander sleeve, and the over-molded seals on the expander sleeve. The basic features in the connection alternatives can comprise a line set connection with an adapter and a standard Luer connector, and a line set connection with a custom Luer connector.

FIGS. 38-41 are views of an eleventh exemplary embodiment of a reservoir and straight-line, push-on connector assembly for interfacing a line set with another infusion pump without an O-ring in accordance with an embodiment of the present invention. The eleventh exemplary embodiment comprises a reservoir and straight-line, push-on connector assembly 1000 for interfacing a line set with a custom Luer connector 1010 with an infusion pump without an O-ring, but possibly having space(s) for an O-ring, in accordance with an embodiment of the present invention. In the eleventh exemplary embodiment shown, a reservoir 1006 is configured to be slidably inserted into the reservoir opening 1004 such that a plunger of the reservoir can be driven through actions of the infusion pump 1002. Once in position, an expander sleeve 1008 can be either inserted into an opening of the accessible end of the reservoir 1006, or can be previously assembled with the end of the reservoir 1006 and simply seated as described above, to thereby secure the reservoir 1006 in the reservoir opening 1004 of the infusion pump 1002 with a simple straight-line, push-on motion.

Figure 40:
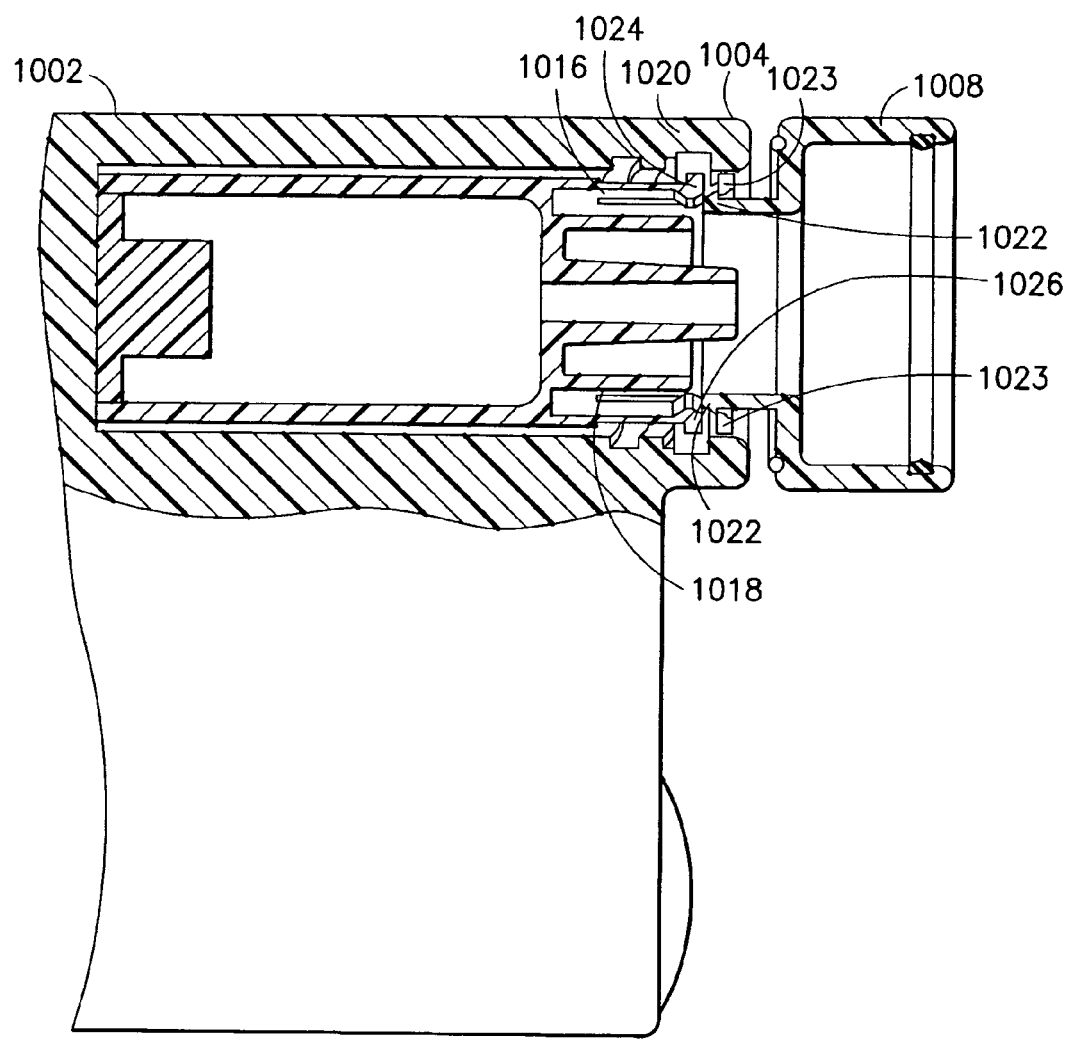
FIG. 40 is an enlarged sectional view of the eleventh exemplary embodiment of a reservoir and straight-line, push-on connector assembly in an unseated position within another infusion pump without an O-ring in accordance with an embodiment of the present invention.
Figure 41:
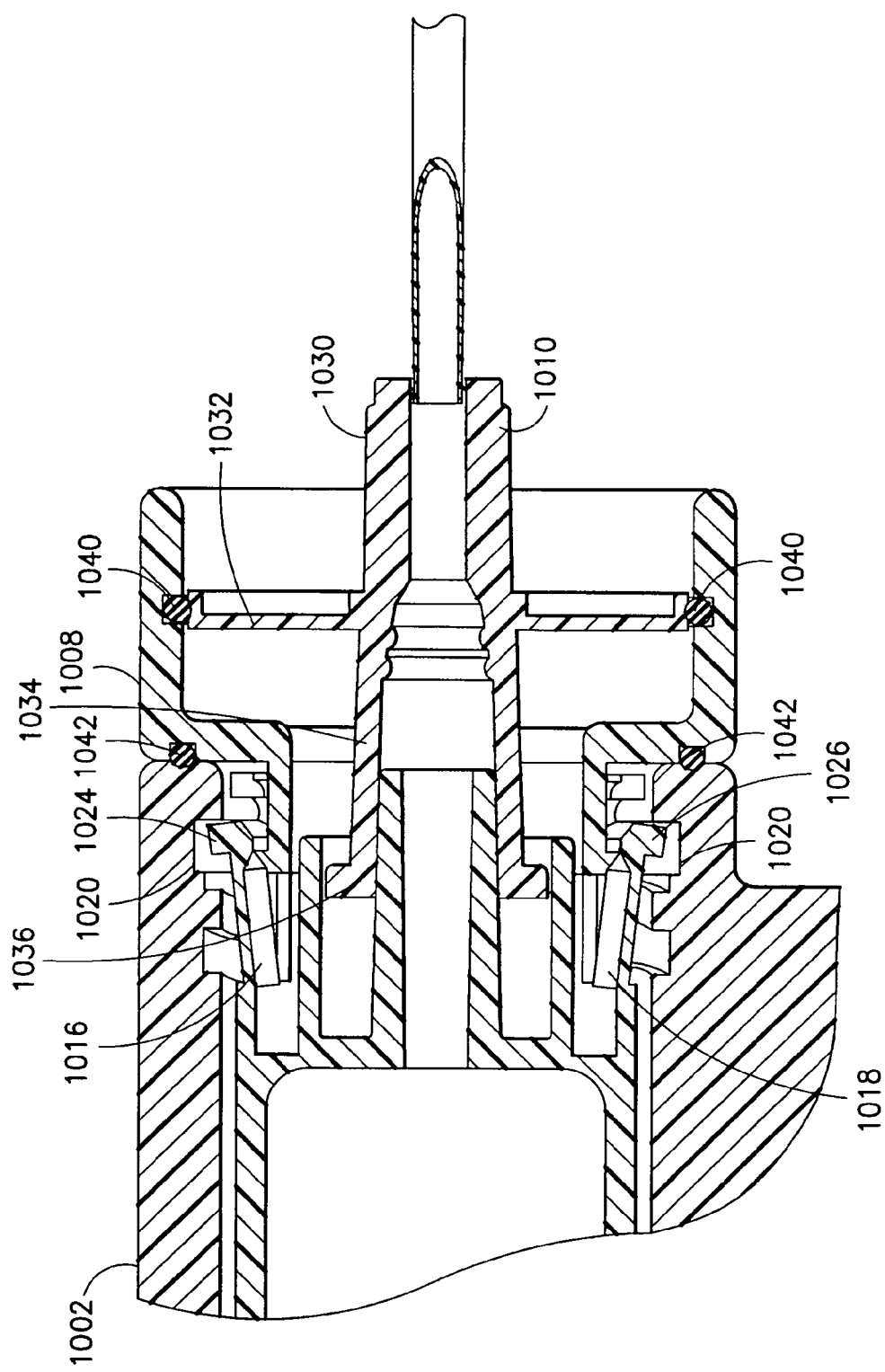
FIG. 41 is an enlarged sectional view of the eleventh exemplary embodiment of a reservoir and straight-line, push-on connector assembly in a seated position within another infusion pump without an O-ring in accordance with an embodiment of the present invention.

Detents 1012 and 1014 of the reservoir 1006 are provided to engage grooves or openings in the reservoir opening 1004 if provided to prevent rotational movement, and arms 1016 and 1018 are configured to be outwardly displaceable to engage at least the O-ring groove 1020 of the reservoir opening 1004. The function and features of the exemplary eleventh embodiment are substantially the same as described above in regard to the first exemplary embodiment, but wherein the arms 1016 and 1020 are provided in a different manner. As shown in FIGS. 40 and 41, the arms 1016 and 1020 extend back toward the opening 1004, in an opposite direction that the embodiments described above, creating a U-shaped opening in which the expander sleeve 1008 enters. Specifically, a tapered ring 1022 of the expander sleeve 1008 is provided and is directed into this U-shaped opening, thereby displacing the arms 1016 and 1018 outward. In doing so, the expanding latches or locking features 1024 and 1026 of the arms 1016 and 1018 are forced into at least the empty O-ring groove 1020.

Further, the expander sleeve 1008 is retained by the reservoir 1004 by mating annular rings on the engagement ends of each component. For example, as shown in FIG. 40, the expander sleeve 1008 comprises the annular ring 1022 which is configured to contact the annular ring 1023 of the reservoir 1004 to prevent complete removal of the expander sleeve 1008 from the annular ring 1022. That is, in this and other exemplary embodiments, the expander sleeve can be slidably captured by the reservoir though the use of such detents.

As shown in FIG. 41, the custom Luer connector 1010 can then be attached. To do so, the connector 1010 includes the first end 1030, second end 1034, flange 1032 and elements 1036. The members 1036 when pressed into the reservoir end serve to further force the securing elements outward as shown in FIG. 41. In a manner as described above, a hydrophobic membrane can be provided on the grasping diameter of the expander sleeve 1008 through one or more hydrophobic membrane covered openings (not shown). Such exemplary features are easily moldable, and the hydrophobic membrane can be heat staked or bonded with UV cured adhesive/epoxy for attachment. An exemplary hydrophobic membrane is comprised of a PTFE or ePTFE material, but is not limited thereto. Such a hydrophobic membrane is provided to allow air ingress and egress to equilibrate pressure internal to the infusion pump reservoir cavity and ambient pressure, while preventing contaminants, fluids and other undesired materials from entering the system. Further, the flange 1032 has a diameter sufficient to seal the opening of the expander sleeve 1008 through engagement with the O-ring 1040 about an ID of the expander sleeve 1008, and the expander sleeve 1008 comprises an O-ring 1042 upon a contact surface between the expander sleeve 1008 and the infusion pump 1002.

Figure 42:
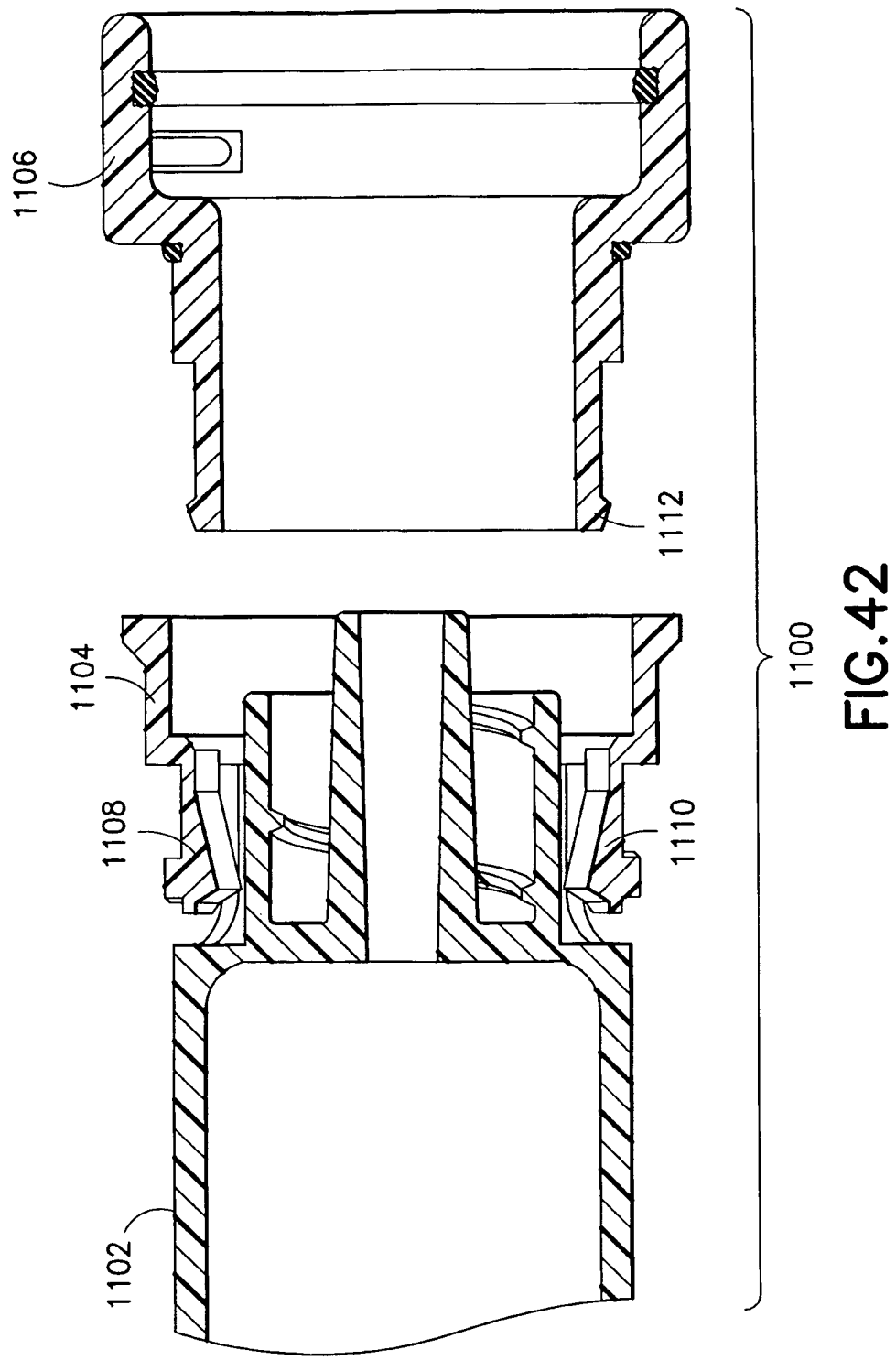
FIG. 42 is an exploded sectional view of a twelfth exemplary embodiment of a reservoir and straight-line, push-on connector assembly for interfacing a line set with an infusion pump at a different engagement angle in accordance with an embodiment of the present invention.
Figure 43:
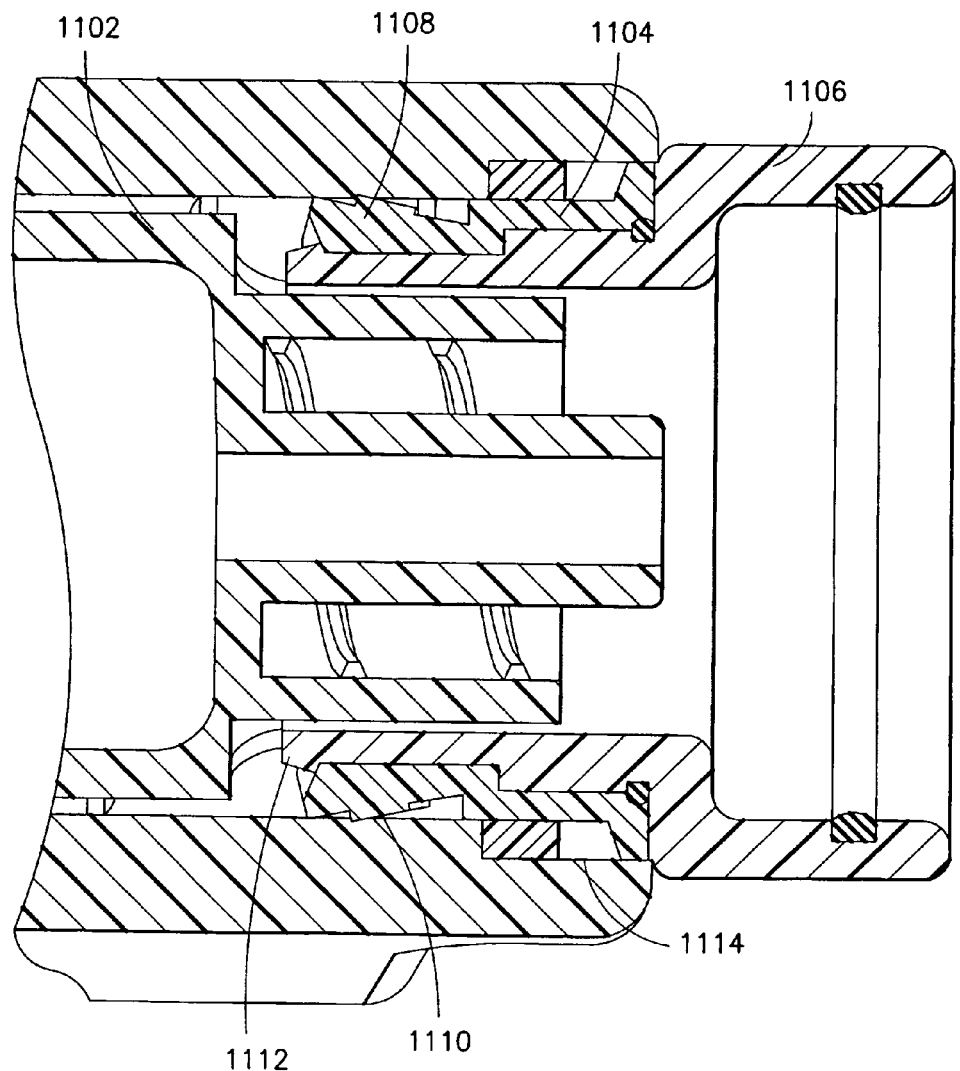
FIG. 43 is an enlarged sectional view of the twelfth exemplary embodiment of a reservoir and straight-line, push-on connector assembly for interfacing a line set with an infusion pump at a different engagement angle in accordance with an embodiment of the present invention.

As noted above, the engagement between the expander sleeve 1008 and the arms 1016 and 1018 of the reservoir 1006 is configured to be sufficient to force the arms and elements thereon sufficiently against the inner wall or annular groove of the reservoir opening to secure the reservoir therein. This angle of engagement can be varied to create desired results. FIG. 42 is an exploded sectional view of a twelfth exemplary embodiment of a reservoir and straight-line, push-on connector assembly for interfacing a line set with an infusion pump at a modified engagement angle in accordance with an embodiment of the present invention.

In the exemplary embodiment shown in FIG. 42, the connector assembly 1100 includes the reservoir 1102, reservoir end 1104 and expander sleeve 1106. The arms 1108 and 1110 of the reservoir 1102 comprise inclines on an inner surface which are configured to engage the contoured edge 1112 of the expander sleeve 1106 much sooner and/or at an angel for increased rate of displacement greater than the exemplary embodiments described above and thereby, create a greater displacement of the arms 1108 and 1110. Such an engagement can be provided to create a greater securing force between uter diameter, wherein said indicator is concealed when said expander sleeve is in said first t position, and said indicator is exposed when said expander sleeve is in said second view showing the engagement between the reservoir 1102 and expander sleeve 1106 when fully seated in a reservoir opening 1114.

Figure 44:
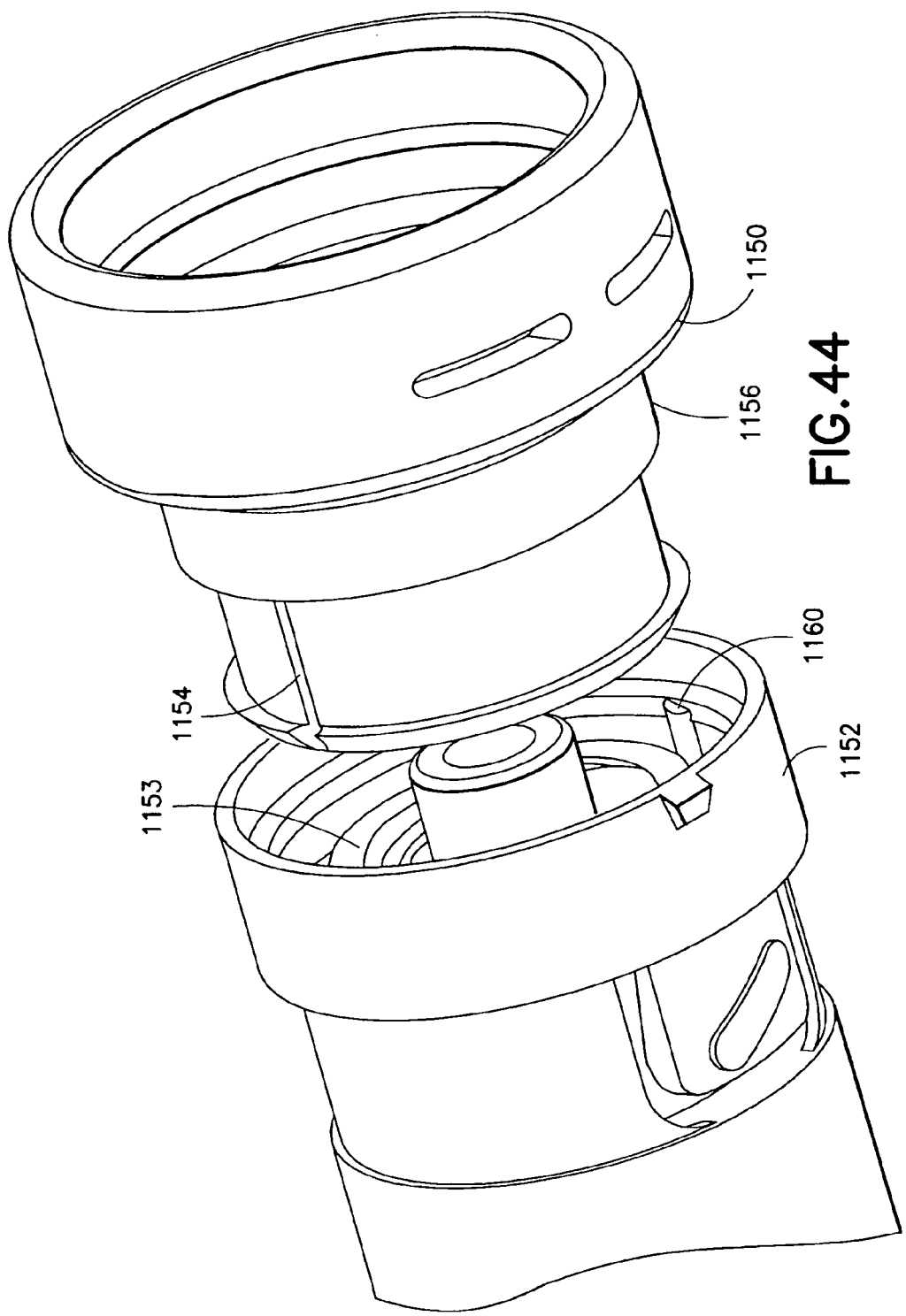
FIG. 44 is an enlarged perspective view of a thirteenth exemplary embodiment of a reservoir and straight-line, push-on connector assembly for interfacing a line set with an infusion pump having an alignment spline in accordance with an embodiment of the present invention.

In yet other exemplary embodiments of the present invention, alignment of at least the expander sleeve and the reservoir can be assisted through the provision of an alignment spine on one or more elements. FIG. 44 is an enlarged perspective view of a thirteenth exemplary embodiment of a reservoir and straight-line, push-on connector assembly for interfacing a line set with an infusion pump having an alignment spline in accordance with an embodiment of the present invention.

Figure 45:
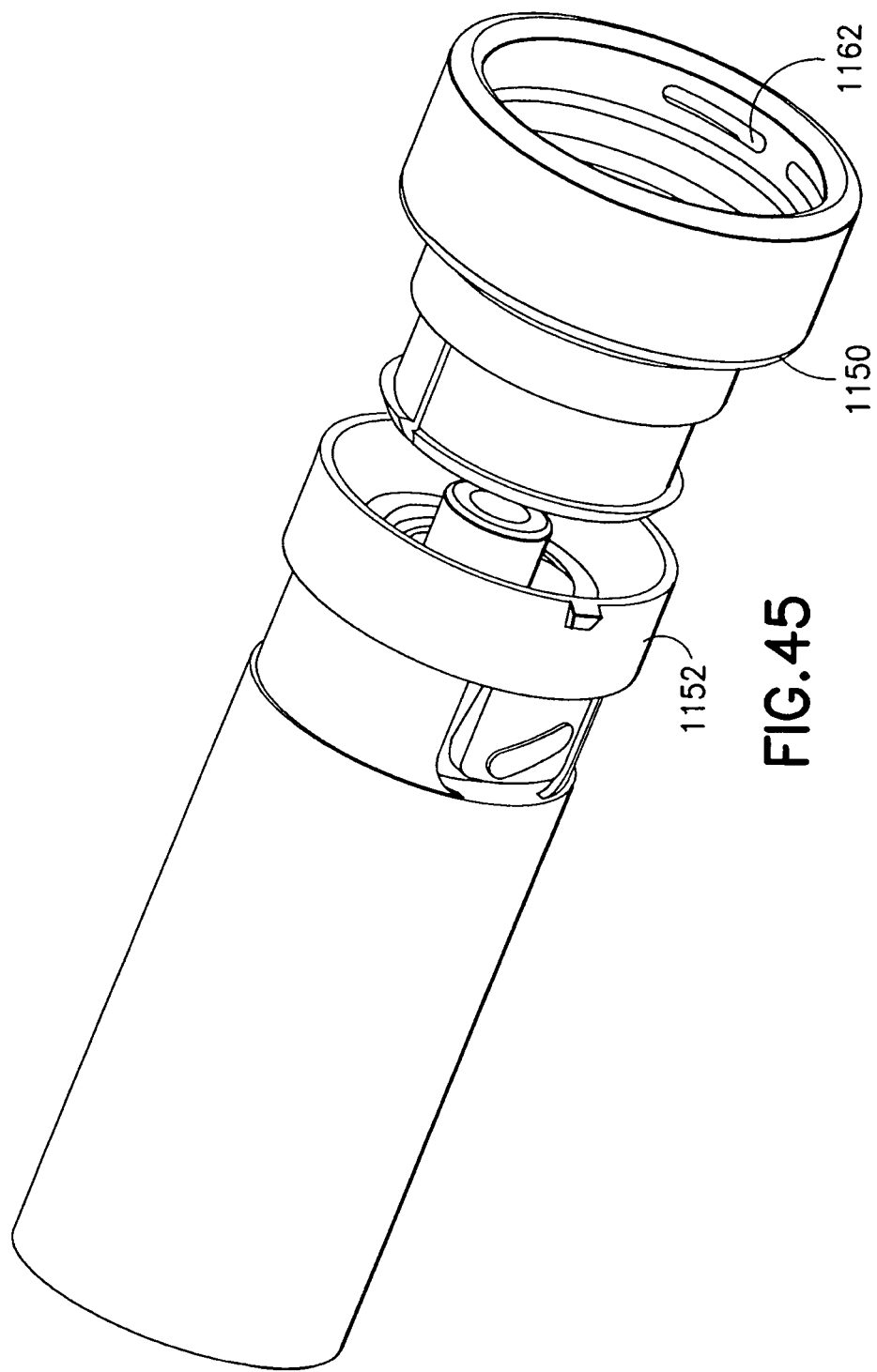
FIG. 45 is an enlarged perspective view of the thirteenth exemplary embodiment of a reservoir and straight-line, push-on connector assembly showing an exemplary hydrophobic membrane therein in accordance with an embodiment of the present invention.

In the exemplary embodiment shown, the expander sleeve 1150 is provided with one or two slots 1154 and 1156 that can be, for example, 180 degrees apart, to engage one or two protrusions 1158 and 1160 of the reservoir 1152. In doing so, a greater degree of alignment can be achieved than that otherwise provided. Further, as shown in FIG. 45, a hydrophobic membrane 1162 can be provided on the grasping diameter of the expander sleeve 1150. An exemplary hydrophobic membrane is comprised of a PTFE or ePTFE material, but is not limited thereto. Such a hydrophobic membrane is provided to allow air ingress and egress to equilibrate pressure internal to the infusion pump reservoir cavity and ambient pressure, while preventing contaminants, fluids and other undesired materials from entering the system.

Figure 46:
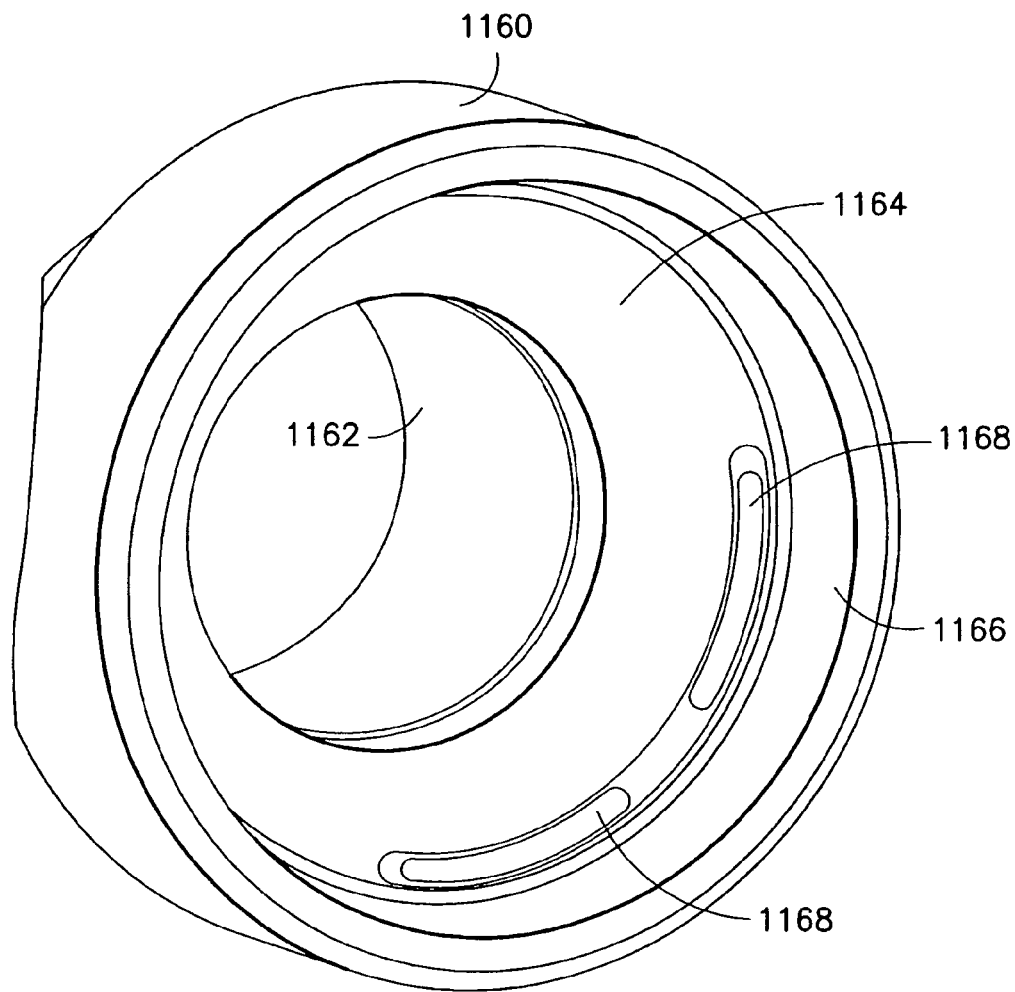
FIG. 46 is an enlarged perspective top view of an expander sleeve showing an exemplary hydrophobic membrane on a flange of the expander sleeve in accordance with an embodiment of the present invention.
Figure 47:
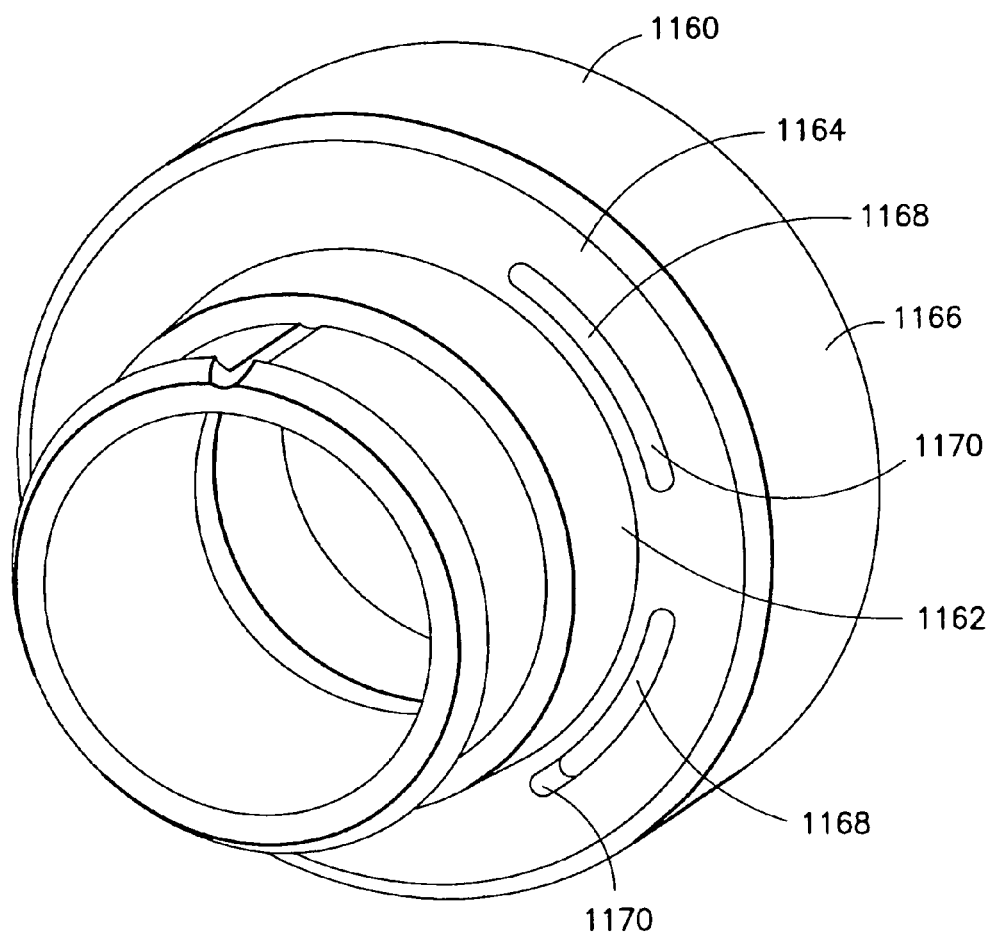
FIG. 47 is an enlarged perspective bottom view of an expander sleeve showing an exemplary hydrophobic membrane on a flange of the expander sleeve in accordance with an embodiment of the present invention.

As noted above, any of the expander sleeves can comprise a grasping diameter and flange, and where desirable to do so, one or more of the grasping diameter and flange can be provided with the hydrophobic membrane. As shown in FIGS. 46 and 47, an expander sleeve 1160 can comprise a first diameter 1162 and a second diameter 1166 thereby creating a flange 1164 therebetween. Further, an exemplary hydrophobic membrane 1168 can be provided over openings in such a flange as shown in the top view of FIG. 46, showing the applied membrane, and the bottom view of FIG. 47 showing the openings 1170. As noted above, the hydrophobic membrane can be heat staked or bonded with UV cured adhesive/epoxy for attachment to the expander sleeve. An exemplary hydrophobic membrane is comprised of a PTFE or ePTFE material, but is not limited thereto. Such a hydrophobic membrane is provided to allow air ingress and egress to equilibrate pressure internal to the infusion pump reservoir cavity and ambient pressure, while preventing contaminants, fluids and other undesired materials from entering the system.

Figure 48:
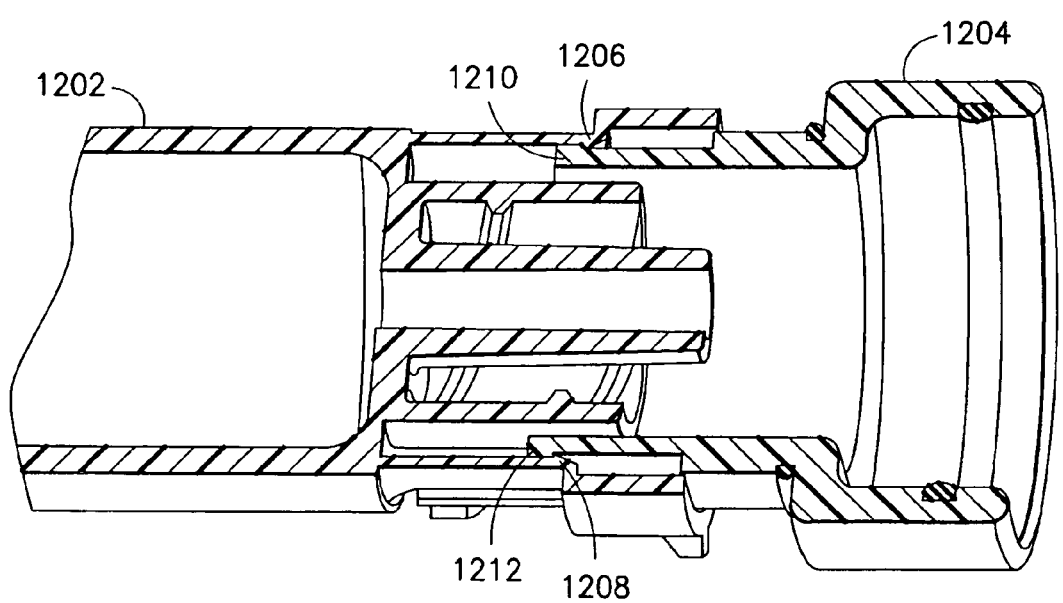
FIG. 48 is an enlarged sectional view of an expander sleeve and reservoir showing a retention ring engagement therebetween in accordance with an embodiment of the present invention.

As also noted above, the expander sleeve can be provided with an annular ring to engage the arms and expanding latches or locking features of the reservoir, and to also engage an annular ring provided in the reservoir to retain the expander sleeve with the reservoir. Such an exemplary embodiment is shown in greater detail in FIG. 48. In FIG. 48, the reservoir 1202 is shown having received the expander sleeve 1204 to a point where the annular ring of the reservoir 1202 shown at 1206, 1208, prevents further retraction of the expander sleeve 1204 through engagement with the annular ring of the expander sleeve shown at 1210, 1212. In doing so, the expander sleeve 1204 is retained by the reservoir 1202 by the mating annular rings on the engagement ends of each component. The retention feature prevents the expander sleeve 1204 from completely separating from the reservoir.

Figure 49:
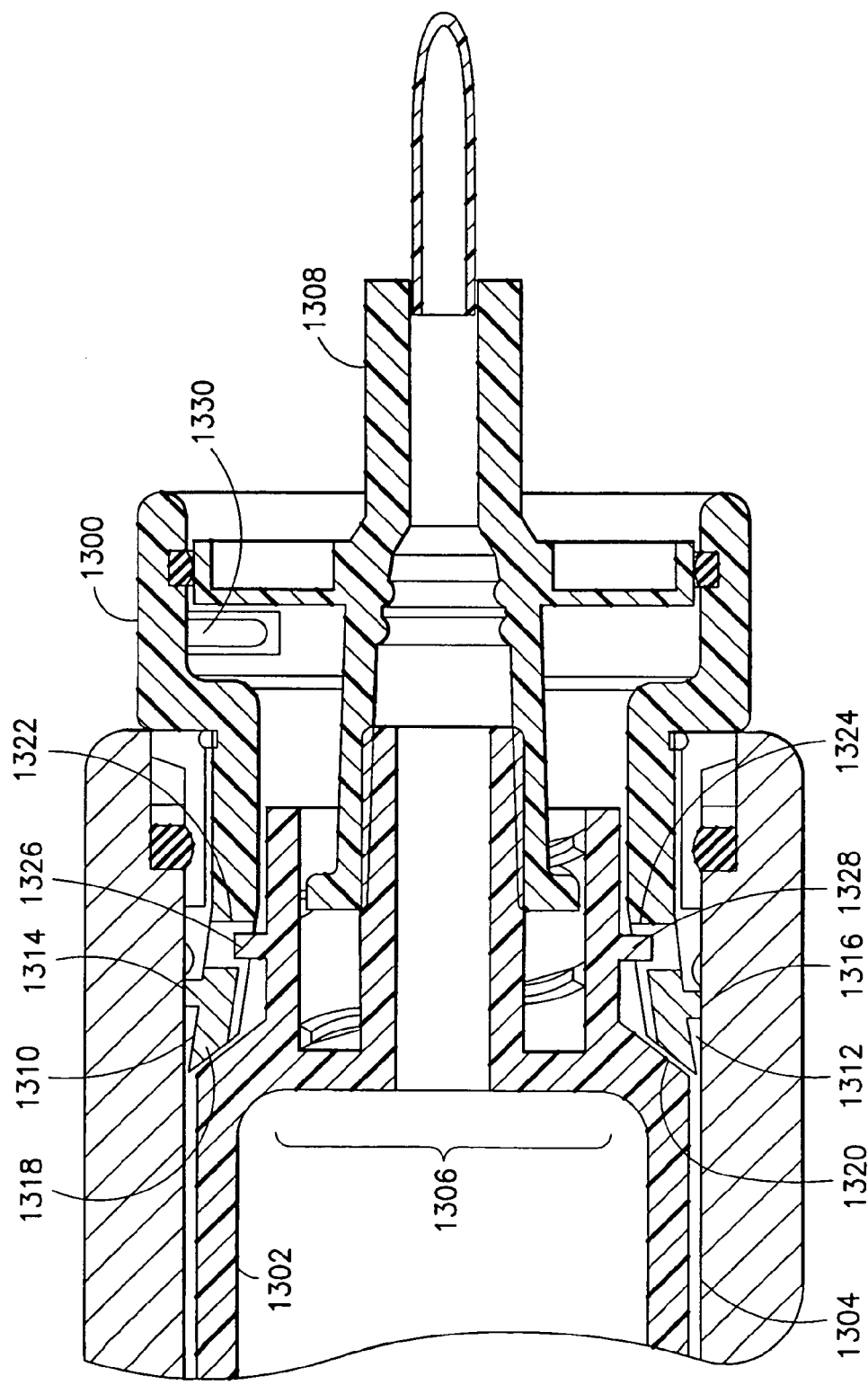
FIG. 49 is an enlarged sectional view of a fourteenth exemplary embodiment of a reservoir and straight-line, push-on connector assembly for interfacing a line set with an infusion pump having engagement features on the expander sleeve in accordance with an embodiment of the present invention.
Figure 50:
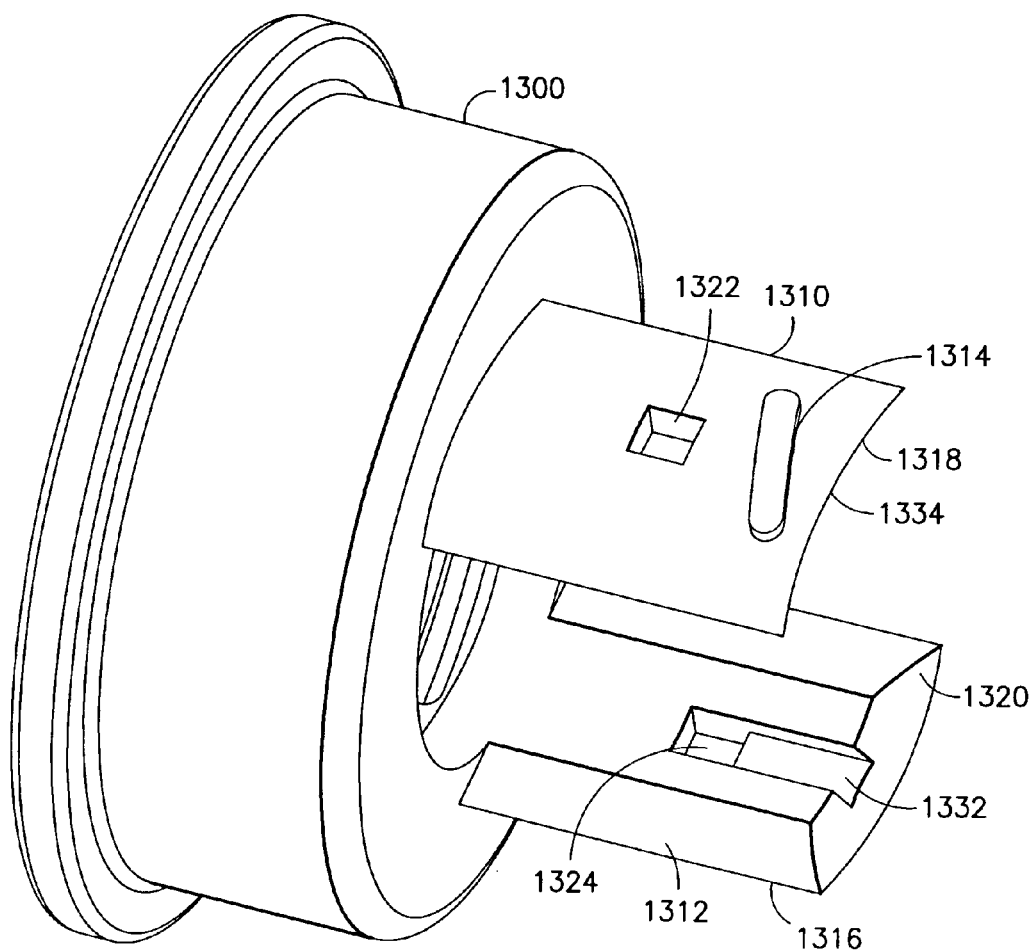
FIG. 50 is an enlarged sectional view of the expander sleeve of FIG. 49 in accordance with an embodiment of the present invention.
Figure 51:
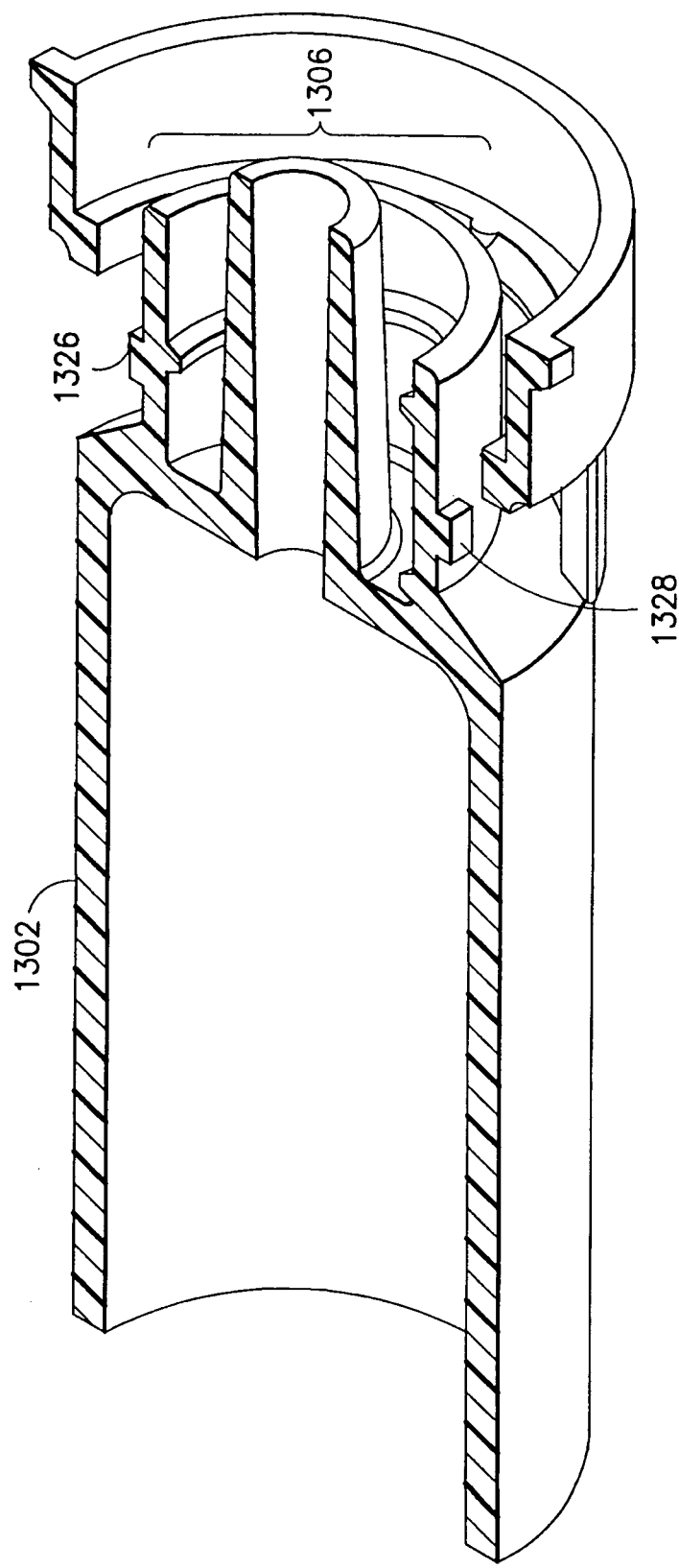
FIG. 51 is an enlarged sectional view of the reservoir of FIG. 49 in accordance with an embodiment of the present invention.

FIGS. 49-51 are views of a fourteenth exemplary embodiment of a reservoir and straight-line, push-on connector assembly for interfacing a line set with the infusion pump of FIG. 1, wherein the expander sleeve comprises the deflectable elements and construction materials. In the embodiment shown in FIG. 49, an expander sleeve 1300 is provided for use with a reservoir 1302 that has been inserted into an infusion pump opening 1304. The reservoir 1302 includes a line set connector assembly 1306 for coupling with an adapter or a custom Luer fitting 1308 as described above. However, in the fourteenth exemplary embodiment, the deflectable members are provided with the expander sleeve 1300, which permits material selection of the reservoir to be simplified.

Specifically, the distal end of the expander sleeve 1300 comprises one or more deflectable arms 1310 and 1312. At an end of each arm, an inclined surface 1318 and 1320 are provided to contact a shoulder of the reservoir 1302. The slidable movement of the expander sleeve 1300 when seating forces the arms 1310 and 1312 of the expander sleeve 1300 into contact with the inclined surfaces, and deflects the deflectable arms 1310 and 1312 outward, such that the features 1314 and 1316 are forced outward to engage any contacted surface, such as those provided by a male or female threaded surface within the opening 1304 of the infusion pump, and secure the reservoir 1302. Further, the exemplary embodiment shown in FIG. 49 illustrates an example of the positioning of a hydrophobic membrane on the grasping diameter of the expander sleeve 1300. In this case, the hydrophobic membrane covered openings 1330 provide a pathway for air ingress and egress for pressure equalization. Such exemplary features are easily moldable, and the hydrophobic membrane can be heat staked or bonded with UV cured adhesive/epoxy for attachment. An exemplary hydrophobic membrane is comprised of a PTFE or ePTFE material, but is not limited thereto.

The distal end of the expander sleeve 1300 further comprises one or more openings 1322 and 1324 in the deflectable arms 1310 and 1312 to secure the expander sleeve with the reservoir. The openings 1322 and 1324 are configured to capture the detents 1326 and 1328 of the reservoir 1302, but wherein the openings are wide enough to allow sufficient movement of the expander sleeve 1300 to engage the inclined surfaces and secure the reservoir without restriction.

FIG. 50 is an enlarged sectional view of the expander sleeve and FIG. 51 is an enlarged sectional view of the reservoir of FIG. 49. As illustrated in FIG. 50, the deflectable arms 1310 and 1312 further comprise slots 1332 and 1334 to receive the detents 1326 and 1328 of the reservoir 1302 to the point of capture within openings 1322 and 1324. As noted above, this permits the reservoir to be constructed entirely of CCP, COP or COC materials, and the expander sleeve 1300 to be constructed entirely of flexible polypropylene or other flexible polymer.

In these various embodiments, the straight-line, push-on connector engages to threads which, as a singular engagement feature in conventional systems, can tend to loosen over time from vibration, impact, or other external influence. However, by incorporating a second engagement feature into the straight-line, push-on connector, which connects with the same straight-line motion that expands the expanding latches or locking features of the reservoir into the male or female threads of the pump reservoir cavity, the engagement of the reservoir is locked, and cannot be disconnected with a turning motion that would typically unscrew threads. Only a reverse, straight-line, pull-off motion will disengage the expander sleeve and release the reservoir, and the disengagement force can be controlled by modifying the angular engagement of the cam surfaces on the expander sleeve and expanding latches or locking features of the reservoir.

A line set with either a standard Luer fitting or a custom Luer fitting can then be installed with the accessible reservoir end through the expander sleeve. In the case of a standard Luer fitting, an adapter is provided between the reservoir and the standard Luer fitting to provide the hydrophobic membrane required for pressure equilibrium. In the case of the custom Luer fitting, the hydrophobic membrane can provided in the custom Luer fitting or expander sleeve. As known to those skilled in the art, air ingress and egress is needed to equilibrate pressure internal to the infusion pump reservoir cavity and ambient pressure. In a conventional system and method, a hydrophobic membrane is incorporated into the line set connector, or incorporated into the one-piece reservoir. In the exemplary embodiments of the present invention described above, a hydrophobic membrane can be incorporated into one or more of the custom Luer connector, i.e., the line set connector, the expander sleeve or the adapter.

Further, as noted above, the conventional systems and methods are configured to engage the pump, i.e., lock the reservoir and connector assembly into the pump reservoir using a combination of a forward motion, i.e., pushing motion, and a turning motion of the reservoir and connector assembly. In the embodiments of the present invention, using a single straight-line, push-on motion, male detent features molded into reservoir or expander sleeve engage detent slots at the top lip of the pump reservoir cavity, and pieces on the expander sleeve engage and secure threads, annular grooves, or simply a side wall in the pump reservoir cavity. Since the reservoir is secured by movement of the expander sleeve, tension on the tube and tube set will not release the reservoir. The reservoir is released by a reverse straight-line, pull-off motion of the expander sleeve.

In doing so, the exemplary embodiments of the present invention described above perform engagement and locking of the reservoir into the infusion pump using only a straight-line, pushing and pulling motion, i.e., no turning motion is required to engage the locking features into the male or female threads of the pump, preferably using a single gripping position on the expander sleeve. The OD of the reservoir body does not interfere with any O-ring in the pump reservoir cavity, so there is no resistance as the reservoir body is advanced into the pump reservoir cavity.

The OD on the connection features at the top of the reservoir is preferably larger than the OD of the reservoir body and a slight degree of resistance occurs as the upper portion of the reservoir engages the opening in the pump. As the reservoir and the connector assembly are fully advanced into the pump reservoir cavity, any rotational alignment required by the pump is made by seating the detents on the reservoir into the openings located at the reservoir opening entrance. To properly seat the detents the user can visually align the detents and openings, and final alignment can provide a tactile feedback signal to the user as the detents advance and contact the bottom of the openings.

In yet other exemplary embodiments of the present invention the alignment of the reservoir can be facilitated by providing two or more opposing flat surfaces to the gripping feature of the expander sleeve. Such surfaces can be aligned with the outer flat surfaces of the infusion pump. Still further, a guide can be integrated into the expander sleeve, and can be configured to automatically align the reservoir to the correct orientation as the reservoir is advanced into the reservoir opening of the infusion pump.

One or more of the exemplary embodiments of the present invention described above utilize a Luer fitting to connect the line set to the reservoir. Further, one or more of the exemplary Luer fittings can require a partial turning to engage the Luer threads and the sealing taper that is part of the Luer connection. However, such turning is not required for the assembly of the reservoir and connector assembly with the infusion pump.

As known to those skilled in the art, the reservoir of such systems can be filled by the user and comprise a number of features configured to permit such filling at a time of use. The conventional systems and methods include reservoirs with septums requiring cannulas for filling, and cannulas in the line set. In contrast, one or more of the exemplary embodiments of the present invention described above utilize a reservoir with a Luer fitting such that the filing of the reservoir can be accomplished with a needle assembly and a plunger.

Figure 52:
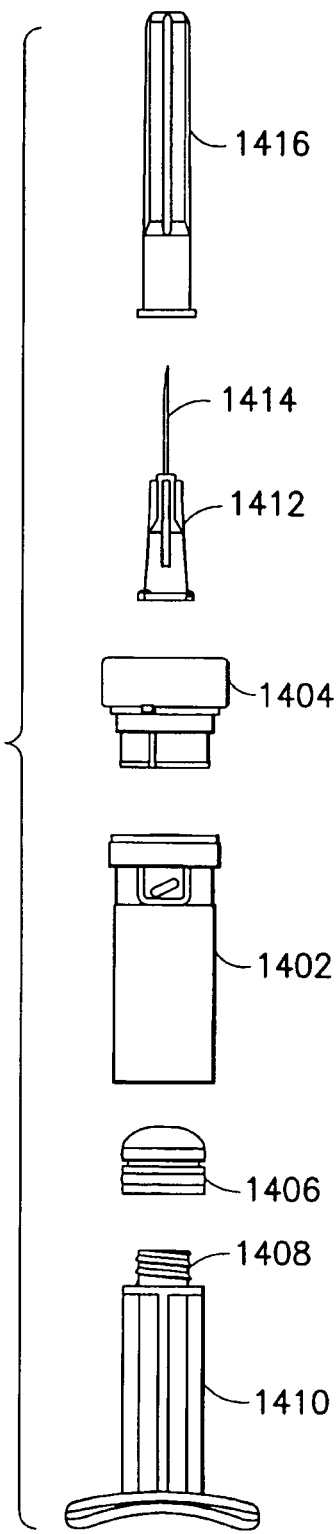
FIG. 52 is an exploded view of a reservoir and connector assembly being filled in accordance with an embodiment of the present invention.
Figure 53:
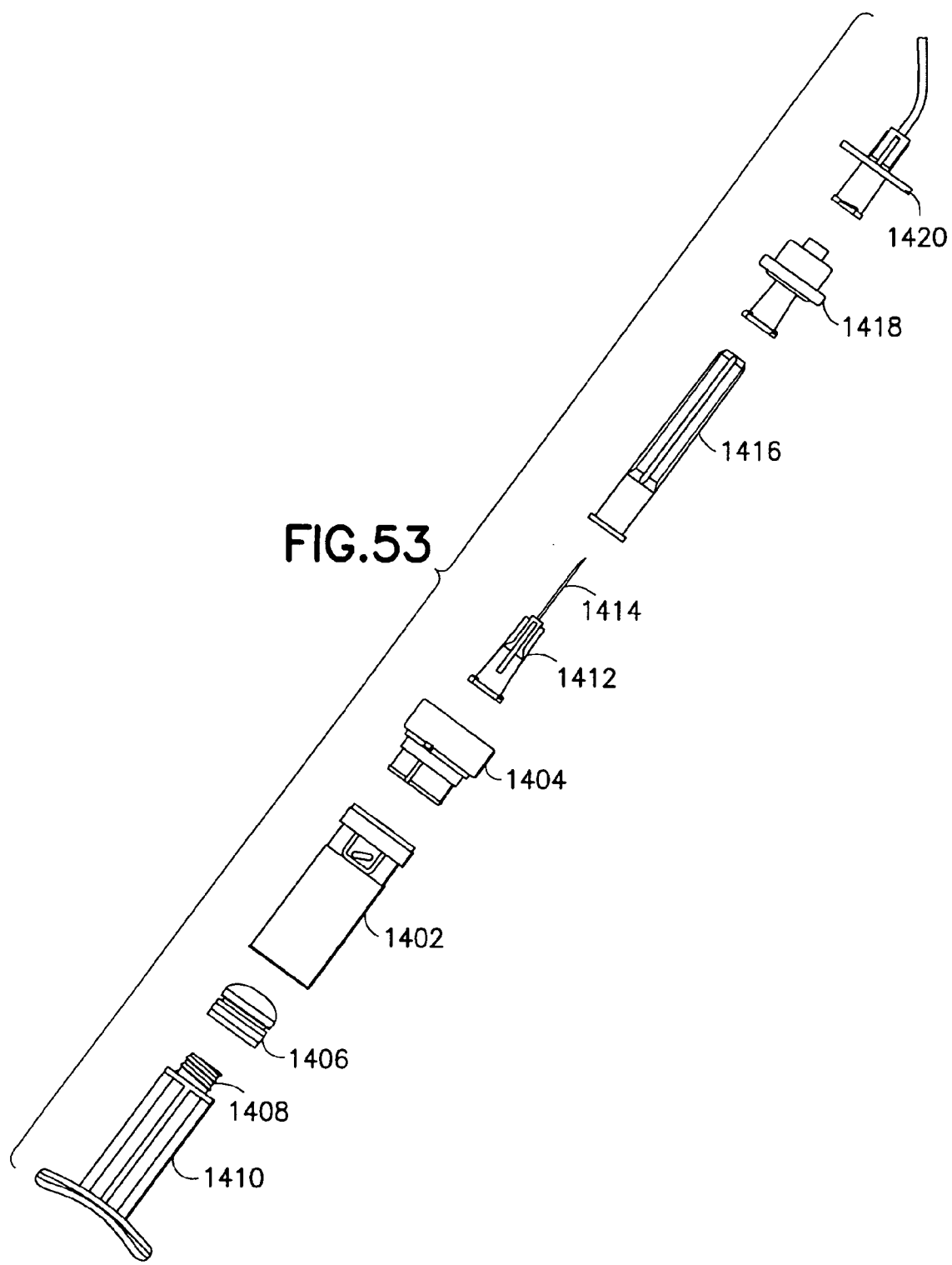
FIG. 53 is an exploded view of a filled reservoir and connector assembly prepared for use in accordance with an embodiment of the present invention.

An exemplary system and method for filling a reservoir is shown in FIGS. 52 and 53. FIGS. 52 and 53 show exploded views of a reservoir and connector assembly first being filled, then prepared for use with an infusion pump. In FIGS. 52 and 53 a reservoir 1402, expander sleeve 1404, and stopper 1406 are shown and perform substantially as described above. The stopper 1406 is threaded to removably receive a plunger 1410 via engagement with the threaded end 1408 of the plunger. At an opposite end, a fill cannula 1414 can be attached using the Luer connector 1412, and can be provided with a shipping shield 1416. Accordingly, the user can receive exemplary embodiments of the present invention wherein the reservoir 1402, expander sleeve 1404, stopper 1406, plunger 1410, fill cannula 1414 and shipping shield 1416 are assembled and packaged.

After removing the assembly from the package, the user can remove the shield 1416 and fill the reservoir 1402 from an insulin supply. In doing so, exemplary embodiments of the present invention do not require an integral reservoir septum as found in conventional systems and methods. After the user draws insulin into the reservoir 1402, the user can remove the fill cannula 1414 and the plunger 1410, and place the reservoir 1402 and expander sleeve 1404 into the pump reservoir cavity as described above using a simple, straight-line, push-on motion. As the reservoir is inserted into the pump reservoir cavity and the expander sleeve is pushed, the locking arms of the reservoir are forced outward, locking the reservoir to the threads of the infusion pump opening, such that the reservoir is inserted and locked in one simple motion. The user can then connect the adapter 1418 and line set Luer connector 1420 to the reservoir 1402, or connect a custom Luer connector to the reservoir, and prime the system to the end of the line set. The system is then ready for operation. When the infusion is complete or removal is otherwise desired, the tube set connector can be removed and the expander sleeve is pulled using a simple, straight-line, pull-off motion, such that the locking arms of the reservoir retract and the reservoir is unlocked and removed from the infusion pump in one simple motion. The reservoir can also be unlocked and removed in such a manner without the removal of the tube set connector if desirable to do so.

In yet other exemplary embodiments of the present invention, a septum can be incorporated into the reservoir and connector assembly to aid in preventing leakage from the reservoir during user setup procedures. In such exemplary embodiments, a septum such as a split septum can be used which also eliminates the need for a cannula in the mating components to pierce the septum. Such a split septum can be stretched open when the connector is attached to the reservoir. Unlike other conventional systems and methods, a reservoir and connector assembly in combination with such a septum can allow a user to place the filled reservoir into the infusion pump and then make the line set connection.

Still other improvements provided by the exemplary embodiments of the present invention described above include improvements in regard to human factors involved. For example, the conventional systems and methods require the user to attach the line set to the reservoir, insert the reservoir and connector into the infusion pump, and turn the reservoir and connector to engage threads therein to the point where detents latch into grooves of the infusion pump body, locking the reservoir in place.

However, the exemplary embodiments of the present invention described above allows the user, after filling the reservoir, to simply attach the line set connector to the mating connection on the reservoir, then using a single straight-line, push-on motion while gripping the expander sleeve, slide the reservoir and connector assembly into the pump reservoir cavity, engage any O-ring seal and expand and lock the engagement features into the mating pump reservoir cavity features. The cognitive element of alignment between the connector assembly and the infusion pump reservoir cavity can be eliminated by integrating a guide into the expander sleeve. In doing so, the guide can automatically align the reservoir and connector assembly to the correct orientation as the reservoir and connector assembly is advanced into the pump reservoir cavity.

Still further, the removal of the reservoir and connector assembly of the exemplary embodiments of the present invention described above is accomplished with a single straight-line, pull-off motion. Feedback is provided in the form of an audible or tactile "click" that occurs as the cam surface of the expander sleeve advances past the cam surface on the upper portion of the reservoir, thereby confirming the complete and proper engagement of the reservoir and connector assembly to the pump to the user.

In addition to the audible and tactile feedback provided by the exemplary embodiments of the present invention, the visible fault detection feature can be provided to identify a fault condition, such as the loosening of the engagement between the reservoir and pump reservoir cavity. To do so, a visible, pronounced (i.e., bright red, fluorescent or contrasting) ring or mark can be incorporated into the expander sleeve, and located on the expander sleeve such that the fault detection ring is exposed if the expander sleeve is not completely advanced. In contrast, conventional systems and methods provide no clear fault detection to determine if unscrewing has occurred, and users find themselves frequently checking alignment of features of the line set with the infusion pump to detect changes that may or may not indicate the connector has loosened or unscrewed to any extent.

As noted above, the removal of the reservoir and connector assembly from the infusion pump reservoir cavity is achieved in a straight-line motion. Specifically, the user can simply use a straight-line, pull-off motion to retract the expander sleeve and disengage the latch features in the reservoir from the mating or contacted pump cavity features, thereby allowing the reservoir to be removed from the pump cavity. In contrast, the conventional systems and methods require the user to grip and turn the line set connector with substantial force to overcome the detent engagement at the top of the opening, and turn still further to release the threaded engagement between the connector and infusion pump cavity. Only then can the user remove the reservoir. As stated previously, users often turn the Luer connection instead of the reservoir connection causing disengagement of the line set and potential leakage into the pump reservoir opening Finally, one or more of the exemplary embodiments of the present invention described above utilize a reservoir seal to avoid leakage during deployment and use. For example, one or more of the exemplary embodiments of the present invention described above utilize a custom Luer connector or a standard Luer connector for the line set connection. In doing so, at least the tapered sleeve of the Luer connector provides a watertight seal between the reservoir and the line set. In contrast, several conventional systems and methods use a septum and cannula in the reservoir assembly to allow fluid flow through the line set. As such, leaks can occur for a number of reasons.

The foregoing embodiments and advantages are merely exemplary and are not to be construed as limiting the scope of the present invention. Various modifications, alternatives and variations will be apparent to those of ordinary skill in the art, and are intended to fall within the scope of the invention.

What is claimed is:

1. A reservoir and straight-line push connector assembly for use with an infusion pump, comprising:
    a reservoir configured to be slidably received within a threaded infusion pump opening, comprising a proximal end and a distal end, wherein said proximal end comprises a deflectable element and at least one detent to rotationally orient said reservoir with at least one groove in said infusion pump opening to prevent rotation of the reservoir with respect to the infusion pump; and
    an expander sleeve slidably engaged with said proximal end of said reservoir, configured to slidably move between a first position to deflect said deflectable element of said reservoir against said threaded opening of said infusion pump to thereby secure said reservoir in said infusion pump opening, and a second position to release said deflection of said deflectable element of said reservoir from said infusion pump opening to thereby release said reservoir from said infusion pump opening;
    wherein said distal end of said reservoir is received within said infusion pump opening when said expander sleeve is slidably engaged with said proximal end of said reservoir.

2. The reservoir and straight-line push connector assembly as recited in claim 1, wherein said reservoir further comprises a fitting to receive a tube set connector, wherein said tube set connector comprises a hydrophobic membrane.

3. The reservoir and straight-line push connector assembly as recited in claim 1, wherein said reservoir further comprises:
    a fitting to receive an adapter, wherein said adapter is configured to receive a tube set connector, and
    wherein at least one of said adapter and said expander sleeve comprises a hydrophobic membrane.

4. The reservoir and straight-line push connector assembly as recited in claim 3, wherein said adapter further comprises a septum, wherein said septum is configured to be opened when coupled with said tube set connector.

5. The reservoir and straight-line push connector assembly as recited in claim 1, wherein said deflectable element comprises:
    an arm secured at one end to said reservoir, said arm comprising an inclined contact surface on a first surface, said inclined surface configured to slidably contact said expander sleeve, and
    said arm comprising an engagement surface on a second surface, said engagement surface configured to contact a surface of said infusion pump opening to thereby secure said reservoir in said infusion pump opening.

6. The reservoir and straight-line push connector assembly as recited in claim 1, wherein said deflectable element comprises:
    a piece, captured within an opening in said reservoir and between said reservoir and said expansion sleeve, said piece comprising an inclined contact surface on a first surface, said inclined surface configured to slidably contact said expander sleeve; and
    said piece comprising an engagement surface on a second surface, said engagement surface configured to contact a surface of said infusion pump opening to thereby secure said reservoir in said infusion pump opening.

7. The reservoir and straight-line push connector assembly as recited in claim 5, wherein said engagement surface comprises at least one of a bar shaped member, a post shaped member, a dual-post shaped member, and a ramp shaped member.

8. The reservoir and straight-line push connector assembly as recited in claim 6, wherein said engagement surface comprises at least one of a bar shaped member, a post shaped member, a dual-post shaped member, and a ramp shaped member.

9. The reservoir and straight-line push connector assembly as recited in claim 1, wherein said expander sleeve further comprises a guide, wherein said guide comprises at least one side configured to extend along an outer surface of said infusion pump.

10. The reservoir and straight-line push connector assembly as recited in claim 1, wherein said expander sleeve comprises an indicator disposed on an outer diameter, wherein said indicator is concealed when said expander sleeve is in said first position, and said indicator is exposed when said expander sleeve is in said second position.

11. The reservoir and straight-line push connector assembly as recited in claim 1, wherein:
    said reservoir comprises a rigid material; and
    an upper sleeve, coupled with said reservoir for receiving said expander sleeve, comprises a flexible material.

12. The reservoir and straight-line push connector assembly as recited in claim 1, wherein said expander sleeve comprises a seal.

13. A method for releasably securing a reservoir in an infusion pump using a straight-line motion, the method comprising:
    slidably inserting a reservoir within an infusion pump opening having a thread element to rotationally receive a reservoir, comprising a proximal end and a distal end, wherein said proximal end comprises a deflectable element; and
    slidably engaging an expander sleeve with said proximal end of said reservoir, between a first position to deflect said deflectable element of said reservoir against said thread element of said infusion pump opening to thereby secure said reservoir in said infusion pump opening, and a second position to release said deflection of said deflectable element of said reservoir from said infusion pump opening to thereby release said reservoir from said infusion pump opening;
    wherein said distal end of said reservoir is received within said infusion pump opening when said expander sleeve is slidably engaged with said proximal end of said reservoir.

14. The method for releasably securing a reservoir in an infusion pump using a straight-line motion as recited in claim 13, further comprising coupling at least one of:
    a tube set connector with said reservoir, wherein said tube set connector comprises a hydrophobic membrane; and
    an adapter with said reservoir, wherein said adapter is configured to receive a tube set connector, and wherein at least one of said adapter and said expander sleeve comprises a hydrophobic membrane.

15. A reservoir for use with an infusion pump, comprising:
    a reservoir body configured to be slidably received within an infusion pump opening, comprising a proximal end and a distal end; and
    an expander sleeve slidably engaged with said proximal end of said reservoir, configured to slidably move between a first position to secure said reservoir in said infusion pump opening, and a second position to release said reservoir from said infusion pump opening, wherein said expander sleeve comprises a seal to seal said infusion pump opening; and wherein said distal end of said reservoir is received within said infusion pump opening when said expander sleeve is slidably engaged with said proximal end of said reservoir; said reservoir further comprising:

a deflectable element, and said expander sleeve is configured to slidably move between the first position to deflect said deflectable element of said reservoir against said infusion pump opening to thereby secure said reservoir in said infusion pump opening, and the second position to release said deflection of said deflectable element of said reservoir from said infusion pump opening to thereby release said reservoir from said infusion pump opening.

16. The reservoir as recited in claim 15, wherein said reservoir and expander sleeve are configured to be coupled with a filling cannula at said proximal end and with a plunger at said distal end for filling of said reservoir.

17. The reservoir as recited in claim 15, wherein said reservoir further comprises:

a fitting to receive a tube set connector, wherein said tube set connector comprises a hydrophobic membrane.

18. The reservoir as recited in claim 15, wherein said reservoir further comprises:

a fitting to receive an adapter, wherein said adapter is configured to receive a tube set connector, and wherein at least one of said adapter and said expander sleeve comprises a hydrophobic membrane.

19. The reservoir as recited in claim 18, further comprising an engagement surface configured to secure at least one of a thread surface and an annular O-ring groove in said infusion pump opening.

20. The reservoir as recited in claim 15, wherein said deflectable element comprises:

an arm secured at one end to said reservoir, said arm comprising an inclined contact surface on a first surface, said inclined surface configured to slidably contact said expander sleeve in said first position, and said arm comprising an engagement surface on a second surface, said engagement surface configured to contact a surface of said infusion pump opening to thereby secure said reservoir in said infusion pump opening.

21. The reservoir as recited in claim 15, wherein said deflectable element comprises:

a piece, captured within an opening in said reservoir and between said reservoir and said expansion sleeve, said piece comprising an inclined contact surface on a first surface, said inclined surface configured to slidably contact said expander sleeve; and said piece comprising an engagement surface on a second surface, said engagement surface configured to contact a surface of said infusion pump opening to thereby secure said reservoir in said infusion pump opening.

22. The reservoir as recited in claim 15, wherein said expander sleeve comprises an indicator disposed on an outer diameter, wherein said indicator is concealed when said expander sleeve is in said first position, and said indicator is exposed when said expander sleeve is in said second position.

23. The reservoir as recited in claim 15, wherein said expander sleeve comprises a contoured outer diameter.

24. The reservoir as recited in claim 15, wherein:

said reservoir comprises one or more of a cyclic olefin polymer (COP), cyclic olefin copolymer (COC) material, and CCP (Crystal Clear Polymer) material; and an upper sleeve, coupled with said reservoir for receiving said expander sleeve, comprises a flexible polypropylene material.

25. The reservoir as recited in claim 15, wherein said reservoir comprises at least one detent at said proximal end to rotationally orient said reservoir with at least one groove in said infusion pump opening.

26. The reservoir as recited in claim 15, wherein said expander sleeve further comprises:

a deflectable element, and said expander sleeve is configured to slidably move between the first position to deflect said deflectable element of said expander sleeve against said infusion pump opening to thereby secure said reservoir in said infusion pump opening, and the second position to release said deflection of said deflectable element of said expander sleeve from said infusion pump opening to thereby release said reservoir from said infusion pump opening.

27. The reservoir as recited in claim 26, wherein said deflectable element comprises:

an arm secured at one end to said reservoir, said arm comprising an inclined contact surface on a first surface, said inclined surface configured to slidably contact said expander sleeve in said first position, and said arm comprising an engagement surface on a second surface, said engagement surface configured to contact a surface of said infusion pump opening to thereby secure said reservoir in said infusion pump opening.

28. The reservoir as recited in claim 26, wherein said deflectable element comprises:

a piece, captured within an opening in said reservoir and between said reservoir and said expansion sleeve, said piece comprising an inclined contact surface on a first surface, said inclined surface configured to slidably contact said expander sleeve; and said piece comprising an engagement surface on a second surface, said engagement surface configured to contact a surface of said infusion pump opening to thereby secure said reservoir in said infusion pump opening.

29. A method for releasably securing a reservoir in an infusion pump using a straight-line motion, the method comprising:

slidably inserting a reservoir within an infusion pump opening using a straight line motion along a primary axis of the reservoir, the infusion pump opening having a thread element adapted to rotationally receive a threaded device, the reservoir comprising a proximal end and a distal end; and slidably engaging an expander sleeve with said proximal end of said reservoir, between a first position to secure said reservoir against said thread element of said infusion pump opening, and a second position to release said reservoir from said infusion pump opening;

wherein said distal end of said reservoir is received within said infusion pump opening when said expander sleeve is slidably engaged with said proximal end of said reservoir; said expander sleeve permitting full insertion of said reservoir without rotation of said reservoir around the primary axis.

30. A method for releasably securing a reservoir in an infusion pump using a straight-line motion, the method comprising:

gripping an expander sleeve of a reservoir and slidably inserting said reservoir in a pump reservoir cavity in a straight-line motion using said expander sleeve until said reservoir is fully within said pump reservoir cavity;

further slidably inserting said expander sleeve into said reservoir in said straight-line motion to secure said reservoir within said pump reservoir cavity by expanding a deflectable element of said reservoir against a thread element of an opening of said pump reservoir cavity; and completing said insertion of said expander sleeve into said reservoir in said straight-line motion when an indicator denotes complete insertion;

wherein said expander sleeve is positioned at a proximal end of said reservoir and a distal end of said reservoir is received in said pump reservoir cavity when said expander sleeve is slidably inserted into said reservoir.

31. A method for releasably securing a reservoir in an infusion pump using a straight-line motion as recited in claim 30, wherein said indicator comprises at least one of a tactile, visual and audible response.

\* \* \* \* \*